United States Patent [19]
Gyorkos et al.

[11] Patent Number: 5,869,455
[45] Date of Patent: Feb. 9, 1999

[54] SERINE PROTEASE INHIBITORS-N-SUBSTITUTED DERIVATIVES

[75] Inventors: Albert Gyorkos, Westminster; Lyle W. Spruce, Arvada, both of Colo.

[73] Assignee: Cortech, Inc., Denver, Colo.

[21] Appl. No.: 761,313

[22] Filed: Dec. 6, 1996

Related U.S. Application Data

[63] Continuation-in-part of Ser. No. 345,820, Nov. 21, 1994, Pat. No. 5,618,792.
[51] Int. Cl.⁶ .............. A61K 38/05; A61K 38/06; C07K 5/06; C07K 5/08
[52] U.S. Cl. .............. 514/18; 514/19; 530/331; 548/128; 548/131; 548/136; 548/143; 548/266.8
[58] Field of Search .............. 514/18, 19, 361, 514/362, 363, 364, 383; 530/330, 331, 332; 548/128, 131, 136, 173, 266.8

[56] References Cited

U.S. PATENT DOCUMENTS

| | | | |
|---|---|---|---|
| 4,338,453 | 7/1982 | Gall | 548/263 |
| 5,055,450 | 10/1991 | Edwards et al. | 514/19 |
| 5,164,371 | 11/1992 | Edwards et al. | 514/18 |
| 5,550,139 | 8/1996 | Groutas | 514/362 |
| 5,618,792 | 4/1997 | Gyorkos et al. | 514/18 |

FOREIGN PATENT DOCUMENTS

| | | | |
|---|---|---|---|
| 0 291 234 | 11/1988 | European Pat. Off. | C07K 5/06 |
| 0 480 044 | 4/1992 | European Pat. Off. | C07D 413/12 |
| 0 528 633 A1 | 2/1993 | European Pat. Off. | C07D 239/46 |
| 0 529 568 A1 | 3/1993 | European Pat. Off. | C07D 5/08 |
| 2 694 295 | 2/1994 | France | C07K 5/12 |
| 2224338 | 11/1972 | Germany | C07D 85/52 |
| 1397073 | 6/1975 | United Kingdom | C07D 271/06 |
| WO 93/21212 | 10/1993 | WIPO | C07K 5/06 |
| WO 95 33762 A | 12/1995 | WIPO | C07K 5/06 |
| WO96/16080 | 5/1996 | WIPO | C07K 5/062 |

OTHER PUBLICATIONS

Skiles, J.W., et al. "Elastase Inhibitors Containing Conformationally Restricted Lactams as $P_3–P_2$ Dipeptide Replacements," Bio. & Med. Chem. Ltrs. 3, 773–778 (1993).

Edwards, P. D., et al. "Peptidyl Alpha–Ketoheterocyclic Inhibitors of Human Neutrophil Elastase. 3. In Vitro and in Vivo Potency of a Series of Peptidyl Alpha–Ketobenzoxazoles," J. Med. Chem. 38, 3972–3982 (1995).

Edwards, P. D., et al. "Nonpeptic Inhibitors of Human Neutrophil Elastase. 7. Design, Synthesis, and in Vitro Activity of a Series of Pyridopyrimidine Trifluoromethyl Ketones," J. Med. Chem. 39, 1112–1124 (1996).

Edwards, P. D., et al. "Peptidyl Alpha–Ketoheterocyclic Inhibitors of Human Neutrophil Elastase. 2. Effect of Varying the Heterocyclic Ring on in Vitro Potency," J. Med Chem. 38, 76–85 (1995).

Veale, C. A., et al. "Non–peptidic Inhibitors of Human Leukocyte Elastase. 4. Design, Synthesis, and in Vitro and in Vivo Activity of a Series of Beta–Carbolinone–Containing Trifluoromethyl Ketones," J. Med. Chem. 38, 86–97 (1995).

(List continued on next page.)

*Primary Examiner*—Jeffrey E. Russel
*Attorney, Agent, or Firm*—Cushman Darby & Cushman IP Group of Pillsbury Madison & Sutro LLP

[57] ABSTRACT

The present invention relates to certain substituted oxadiazole, thiadiazole and triazole peptoids which are useful as inhibitors of human neutrophil elastase (HNE) for the treatment of HNE-mediated processes implicated in conditions such as adult respiratory distress syndrome, septic shock and multiple organ failure. A series of studies also have indicated the involvement HNE in myocardial ischemia-reperfusion injury, emphysema. HNE-mediated processes are implicated in other conditions such as arthritis, periodontal disease, glomerulonephritis, dermatitis, psoriasis, cystic fibrosis, chronic bronchitis, atherosclerosis, Alzheimer's disease, organ transplantation, corneal ulcers, and invasion behavior of malignant tumors.

19 Claims, 38 Drawing Sheets

OTHER PUBLICATIONS

Veale, C. A., et al. "Nonpeptidic Inhibitors of Human Leukocyte Elastase. 5. Design, Synthesis, and X-ray Crystallography ofa Series of Orally Active 5-Aminopyrimidin-6-one-Containing Trifluoromethyl Ketones," J. Med. Chem. 38, 98-108 (1995).

Goddard, C. J., "Antiinflammatory 1-Phenylpyrazole-4-Heteroarylalkanoic Acids," J. Heterocyclic Chem., 28, 1607-1612 (1991).

LaMattina, J. L., et al. "Utility of 24 p-Nitrophenyl 3-Bromo-2,2-diethoxypropionate (NPBDP) in Heterocyclic Synthesis," J. Org. Chem. 49, 4800-4805 (1984).

Unangst, P. C., et al. "Novel 1,2,4-Oxadiazoles and 1,2,4-Thiadiazoles as Dual 5-Lipoxygenase and Cyclooxygenase Inhibitors," J. Med. Chem. 35, 3691-3698 (1992).

Kitatani, K., et al. "A Novel Oxazole Synthesis Utilizing Tungsten(VI) Catalyzed Decomposition of Alpha-Diazo Carbonyl Compounds in Nitriles," Tet. Lett. 16, 1531-1532 (1974).

Wiley, R. H., "Chemistry of the Oxazoles," Chem. Rev. 37, 401-442 (1945).

Davidson, D., et al. "The Action of Ammonia on Benzoin," J. Org. Chem. 2, 328-334 (1937).

Wiegand, Edwin E., et al. "Polyphosphoric Acid Cyclization of Acetamidoketones to 2,5-Dimethyl-1,3-oxazoles," Synthesis 12, 648-649 (1970).

Wasserman, H.H., et al. "The Oxazole-Triamide Rearrangement. Application To Peptide Synthesis," Tet. Lett. Vol. 23, No. 37, 3831-3834 (1982).

Comforth, J. W., et al. "A New Synthesis of Oxazoles and Iminazoles including its Application to the Preparation of Oxazole." J. Chem Soc. 96-102 (1947).

Comforth, J. W., et al. "Synthesis of Oxazoles from Ethyl Acetoacetate. Ring-fission of Some Oxazole-5 carboxylic Acids." J. Chem. Soc. 93-98 (1953).

Bernstein, P. R., et al. "Nonpeptidic Inhibitors of Human Leukocyte Elastase. 3. Design, Synthesis, X-Ray Crystallographic Analysis, and Structure-Activity Relationships for a Series of Orally Active 3-Amino-6-phenylpyridin-2-one Trifluoromethyl Ketones," J. Med. Chem. 37, 3313-3326 (1994).

Brown, F. J., et al. "Design of Orally Active, Non-Peptidic Inhibitors of Human Leukocyte Elastase," J. Med. Chem. 37, 1259-1261 (1994).

Damewood, J. R., Jr. et al. "Nonpeptidic Inhibitors of Human Leukocyte Elastase. 2. Design, Synthesis, and in vitro Activity of a Series of 3-Amino-6-arylopyridin-2-one Trifluoromethyl Ketones," J. Med. Chem. 37, 3303-3312 (1994).

Warner, P., et al. "Non-peptidic Inhibitors of Human Leukocyte Elastase. 1. The Design and Synthesis of Pyridone-Containing Inhibitors," J. Med. Chem. 37, 3090-3099 (1994).

Budavari, Susan (Editor), "The Merck Index" An Encylopedia of Chemicals, Drugs, and Biologicals; Merck & Co., Inc., p. 294 (1989).

| CE# | R | $K_I$ (nM) | CE# | R | $K_I$ (nM) |
|---|---|---|---|---|---|
| 2039 | phenyl | 2.0 | 2054 | 3,5-bis(CF₃)phenyl | 0.29 |
| 2042 | 2-OMe phenyl | 2.5 | 2055 | 3-Me phenyl | 0.49 |
| 2045 | 4-OMe phenyl | 1.0 | 2058 | 4-phenylphenyl | 0.56 |
| 2048 | 3-CF₃ phenyl | 0.36 | 2062 | 3-phenylphenyl | 0.30 |
| 2049 | 3-OMe phenyl | 0.5 | 2066 | 3-phenoxyphenyl | 0.98 |
| 2052 | 3,5-diMe phenyl | 0.37 | 2096 | 3,5-diPh phenyl | 0.8 |
| 2053 | 3,5-diOMe phenyl | 0.41 | 2115 | 4-NMe₂ phenyl | 1.0 |

| CE# | R | $K_I$ (nM) | CE# | R | $K_I$ (nM) |
|---|---|---|---|---|---|
| 2046 | phenyl | 9.9 | 2077 | naphthyl | 0.15 |
| 2047 | propylphenyl | 3.8 | 2078 | pyridyl | 1.05 |
| 2050 | butylphenyl | 1.84 | 2092 | morpholinoethyl | 6.3 |
| 2057 | diphenylethyl | 0.38 | 2103 | dimethylaminopropyl | 12.4 |
| 2069 | cyclohexyl | 4.4 | 2119 | methyl butanoate | 7.7 |
| 2073 | tBu-CF3-phenyl | 0.24 | 2152 | naphthyl | 0.24 |
| 2076 | adamantyl | 1.46 | | | |

| CE# | R | $K_i$ (nM) |
|---|---|---|
| 2072 | 3-methyl-5-benzyl (CH₃ on phenyl) | 0.025 |
| 2074 | —CH₃ | 0.99 |
| 2075 | 3-CF₃-benzyl | 0.11 |
| 2100 | 4-(dimethylamino)benzyl | 0.069 |
| 2123 | —N(CH₃)₂ | 15.1 |
| 2124 | 1-naphthylmethyl | 0.033 |

| CE# | R₁ | R₂ | R₃ | HET | $K_I$(nM) |
|---|---|---|---|---|---|
| 2083 | Cbz- | CH₃ | CH₃ | (methyl-oxadiazole-CH₂-phenyl-CH₃) | 73.0 |
| 2098 | morpholine-C(O)- | i-Propyl | H | (methyl-oxadiazole-CH₂CH₂-morpholine) | 85.0 |
| 2104 | morpholine-C(O)- | i-Propyl | H | (methyl-oxadiazole-CH₂-phenyl-CH₃) | 0.33 |
| 2109 | morpholine-C(O)- | i-Propyl | H | (methyl-oxadiazole-CH₂CH₂-NMe₂) | 126 |
| 2110 | MeO-phenyl-C(O)- | i-Propyl | H | (methyl-oxadiazole-CH₂-phenyl-CF₃) | 0.13 |

| CE# | R | $K_I$ (nM) |
|---|---|---|
| 2072 | 3-methylphenyl-CH₂- | 0.025 |
| 2074 | —CH₃ | 0.99 |
| 2075 | 3-CF₃-phenyl-CH₂- | 0.11 |
| 2100 | 4-(N,N-dimethylamino)phenyl-CH₂- | 0.069 |
| 2123 | —N(CH₃)₂ | 15.1 |
| 2124 | 1-naphthyl-CH₂- | 0.033 |

| CE# | R | HET | $K_i$ (nM) |
|---|---|---|---|
| 2130 | | B | 10.0 |
| 2132 | | A | 24.0 |
| 2134 | | B | 2.0 |
| 2135 | | A | 17 |
| 2126 | | B | 5.05 |
| 2127 | | A | 33.9 |

Heterocycles:

| CE# | R | HET | $K_I$ (nM) |
|---|---|---|---|
| 2125 | Cbz-HN-... (indoline-acetyl-valyl) | A | 0.40 |
| 2145 | Cbz-HN-... (indoline-acetyl-valyl) | B | 0.038 |
| 2143 | H₃C-CO-... (indoline-acetyl) | A | 25.0 |
| 2056 | Cbz-HN-valyl-N(Bn)-CH₂C(O)CH₃ | A | 0.98 |
| 2097 | pyrrole-C(O)-N(Bn)-CH₂C(O)CH₃ | A | 60.0 |
| 2156 | H₂N-... (benzazepinone-CH₂C(O)CH₃) | A | 512.0 |

Heterocycles:

A

B

| CE# | R | HET | $K_i$ (nM) |
| --- | --- | --- | --- |
| 2089 | Cbz-NH- | A | 1.5 |
| 2090 | NH$_2$- | A | 2.7 |
| 2095 | Cbz-NH- | B | 0.21 |
| 2101 | NH$_2$- | B | 0.64 |

Heterocycles:

| CE# | R$_1$ | R$_2$ | K$_i$(nM) |
|---|---|---|---|
| 2107 | Cbz-NH- | (N-methylpiperidinyl) | 17.0 |
| 2108 | Cbz-NH- | H | 10.5 |
| 2113 | H$_2$N- | H | 38.8 |
| 2116 | morpholino-CH$_2$-C(O)-NH- | H | 76.3 |
| 2117 | MeO-C(O)-CH$_2$- | F | 587.0 |

CE-2088
K$_i$ = 66.0 nM

I

II

| CE# | R | Structure | HET | $K_I$ (nM) |
|---|---|---|---|---|
| 2138 | acetylphenyl | I | B | 294.0 |
| 2147 | phenyl | I | B | 1590 |
| 2148 | phenyl | I | A | >6000 |
| 2140 | acetylphenyl | II | B | 204.4 |

Heterocycles:

A

B

| CE# | R₁ | R₂ | $K_i$ (nM) |
|---|---|---|---|
| 2079 | Cbz-NH- | H | 35.5 |
| 2080 | H₂N- | H | 62.0 |
| 2087 | H | —C₆H₄—F (4-F) | 19.8 |
| 2091 | morpholine-CO-CH₂CH₂-CO-NH-Me | H | 270.0 |

| CE# | n | X | HET | R | $K_i$ (nM) |
|---|---|---|---|---|---|
| 2118 | 2 | S | 5-methyl-1,3,4-oxadiazol-2-yl-CH₂-(3-methylphenyl) | phenyl | 13.2 |
| 2121 | 1 | S | 5-methyl-1,3,4-oxadiazol-2-yl-CH₂-(3-methylphenyl) | phenyl | 28.0 |
| 2122 | 1 | S | 5-methyl-1,3,4-oxadiazol-2-yl-CH₂-(3-methylphenyl) | benzyl | 62.7 |
| 2136 | 1 | SO | 5-methyl-1,3,4-oxadiazol-2-yl-CH₂-(3-methylphenyl) | benzyl | 104.0 |
| 2137 | 1 | SO | 3-methyl-1,2,4-oxadiazol-5-yl-CH₂-(3-CF₃-phenyl) | benzyl | 557.0 |

| CE# | R | $K_i$ (nM) |
|---|---|---|
| 2099 | phenyl | 1.9 |
| 2105 | 4-F-phenyl | 0.72 |
| 2111 | 4-N(CH3)2-phenyl | 20.1 |
| 2112 | 4-CO2Me-phenyl | 1.17 |
| 2114 | 4-pyridyl | 25.1 |

| CE# | R₁ | R₂ | R₃ | HET | $K_I$ (nM) |
|---|---|---|---|---|---|
| 2084 | CH₃ | phenyl | H | A | 133.0 |
| 2106 | CH₃ | phenyl | H | B | 40.7 |
| 2120 | CH₃CO- | benzyl | H | B | 50.9 |
| 2128 | benzyl | —H | benzyl | B | 64.0 |
| 2129 | benzyl | —H | benzyl | A | 300.3 |
| 2133 | benzyl | —H | benzyl | C | 33200 |
| 2139 | H— | benzyl | H | B | 41.0 |
| 2144 | benzyl | benzyl | —H | B | 9.3 |
| 2146 | benzyl | benzyl | —H | A | 67.3 |

Heterocycles:

| CE# | R₁ | R₂ | HET | $K_i$ (nM) |
|---|---|---|---|---|
| 2141 | benzyl | H | A | 64.0 |
| 2142 | benzyl | H | B | 8.7 |
| 2149** | phenyl | H | B | 0.28 |
| 2154 | H | benzyl | B | 10.0 |
| 2155 | H | benzyl | A | 57.0 |

** Stereochemistry is not definitive

Heterocycles:

| CE# | HET | $K_l$ (nM) |
|---|---|---|
| 2150 | (3-methyl-1,2,4-oxadiazol-5-yl)-CH2-C6H4-CF3 | >1000 |
| 2151 | (5-methyl-1,3,4-oxadiazol-2-yl)-CH2-C6H4-CH3 | 60 |

SERINE PROTEASE INHIBITORS-N-SUBSTITUTED DERIVATIVES

This application is a continuation-in-part of U.S. Ser. No. 08/345,820 filed Nov. 21, 1994 now U.S. Pat. No. 5,618,792.

The present invention relates to certain substituted oxadiazole, thiadiazole and triazole peptoids which are useful as inhibitors of serine proteases.

BACKGROUND OF THE INVENTION

The serine proteases are a class of enzymes which includes elastase, chymotrypsin, cathepsin G, trypsin and thrombin. These proteases have in common a catalytic triad consisting of Serine-195, Histidine-57 and Aspartic acid-102 (chymotrypsin numbering system). Human neutrophil elastase (HNE) is a proteolytic enzyme secreted by polymorphonuclear leukocytes (PMNs) in response to a variety of inflammatory stimuli. This release of HNE and its extracellular proteolytic activity are highly regulated and are normal, beneficial functions of PMNs. The degradative capacity of HNE, under normal circumstances, is modulated by relatively high plasma concentrations of $\alpha_1$-proteinase inhibitor ($\alpha_1$-PI). However, stimulated PMNs produce a burst of active oxygen metabolites, some of which (hypochlorous acid for example) are capable of oxidizing a critical methionine residue in $\alpha_1$-PI. Oxidized $\alpha_1$-PI has been shown to have limited potency as an HNE inhibitor and it has been proposed that alteration of this protease/antiprotease balance permits HNE to perform its degradative functions in localized and controlled environments.

Despite this balance of protease/antiprotease activity, there are several human disease states in which a breakdown of this control mechanism is implicated in the pathogenesis of the condition. Improper modulation of HNE activity has been suggested as a contributing factor in adult respiratory distress syndrome, septic shock and multiple organ failure. A series of studies also have indicated the involvement of PMNs and neutrophil elastase in myocardial ischemia-reperfusion injury. Humans with below-normal levels of $\alpha_1$-PI have an increased probability of developing emphysema. HNE-mediated processes are implicated in other conditions such as arthritis, periodontal disease, glomerulonephritis, dermatitis, psoriasis, cystic fibrosis, chronic bronchitis, atherosclerosis, Alzheimer's disease, organ transplantation, corneal ulcers, and invasion behavior of malignant tumors.

There is a need for effective inhibitors of HNE as therapeutic and as prophylactic agents for the treatment and/or prevention of elastase-mediated problems.

SUMMARY OF THE INVENTION

The present invention provides compounds which are useful as serine protease inhibitors, including human neutrophil elastase. These compounds are characterized by their relatively low molecular weight, high potency and selectivity with respect to HNE. They can be used effectively to prevent, alleviate or otherwise treat disease states characterized by the degradation of connective tissue by proteases in humans.

The present invention provides compounds comprising oxadiazole, thiadiazole or triazole ring structures, and can be generically described by the formula:

where X and Y are N, O or S; Z is an α-amino carbonyl containing group; and $R_1$ is a variable, both Z and $R_1$ being more fully described in parent application U.S. Ser. No. 08/345,820 (WO 96/16080), now U.S. Pat. No. 5,618,792 the contents of which are incorporated in their entirety.

The present invention provides compounds preferably comprising 1,2,4-oxadiazole (i.e., X is O; Y is N) or 1,3,4 oxadiazole rings (i.e., X is N; Y is O). It has been found that compounds comprising 1,3,4 oxadiazole ring structures possess improved inhibitory activity. The present invention further provides compounds comprising various $R_1$ and Z substituents. The compounds of the present invention may be conveniently categorized as Groups I through VI.

In one preferred embodiment, the invention provides compounds of the formula (Group I):

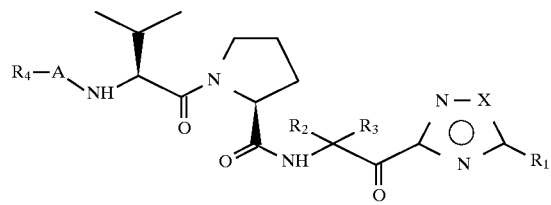

wherein

X and Y are O, N, or S where at least one of X or Y is N;

$R_1$ is alkyl or alkenyl, optionally substituted with halo or hydroxy; alkynyl, alkyl-C(O)OCH$_3$, dialkylamino, alkyldialkylamino; or cycloalkyl, alkylcycloalkyl, alkenylcycloalkyl, ($C_5$–$C_{12}$)aryl, ($C_5$–$C_{12}$)arylalkyl or ($C_5$–$C_{12}$)arylalkenyl optionally comprising one or more heteroatoms selected from N, S, or non-peroxide O, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamido, ($C_5$–$C_6$)aryl, —O—($C_5$–$C_6$)aryl, arylcarboxamido, alkylthio or haloalkylthio;

$R_2$ and $R_3$ are independently or together H, alkyl, alkylthio, alkylthioalkyl or cycloalkyl, alkylcycloalkyl, phenyl or phenyl alkyl optionally substituted with guanidine, carboalkoxy, hydroxy, haloalkyl, alkylthio, alkylguanidine, dialkylguanidine or amidine;

A is a direct bond, —C(O)—, —NH—C(O)—, —S(O)$_2$—, —OC(O)—, —C—, or an amino acid selected from proline, isoleucine, cyclohexylalanine, cysteine optionally substituted at the sulfur with alkyl, alkenyl or phenyl optionally substituted with halogen, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio, haloalkylthio; phenylalanine, indoline-2-carboxylic acid; tetrahydrosioquinoline-2-carboxylic acid optionally substituted with alkyl, alkenyl, haloalkenyl, alkynyl, halogen, cyano, nitro, haloalkyl, amino, aminoalkyl, dialkylamino, alkoxyl, haloalkoxy, carbonyl, carboalkoxy, alkylcarboxamide, arylcarboxamide, alkylthio or haloalkythio; tryptophan, valine, norvaline, norleucine, octahydroindole-2-carboxylic acid, lysine optionally substituted at the nitrogen with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused aryl-cycloalkyl alkyl optionally comprising 1 or more heteroatoms selected from N, O and S; and $R_4$ is H, alkyl, alkenyl, or cycloalkyl, aryl, arylalkyl or fused aryl-cycloalkyl optionally comprising one or more heteroatoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamido, aryl, arylcarboxamido, alkylthio or haloalkylthio.

In a preferred embodiment, X is N and Y is O. In another preferred embodiment, X is O and Y is N. Preferably, $R_4$-A is benzyloxycarbonyl.

Preferably, $R_2$ is isopropyl and $R_3$ is H.

In a preferred embodiment of the invention, $R_1$ is optionally substituted benzyl, preferably selected from methylbenzyl, 3,4-methylenedioxybenzyl or trifluoromethylbenzyl. Alternatively, benzyl is substituted with dialkylamino, preferably dimethylamino. In yet another embodiment, $R_1$ is methylenenaphthyl or an alkyl group, preferably methyl.

The present invention further provides compounds of the formula (Group II):

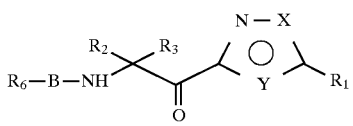

wherein

X, Y, $R_1$, $R_2$ and $R_3$ are as described above;

B is $-S(O)_2-$ or $-C(O)-$;

$R_6$ is

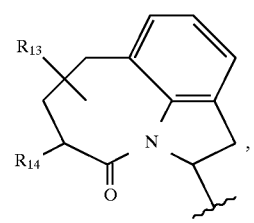

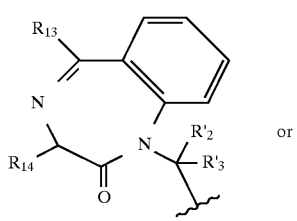

-continued

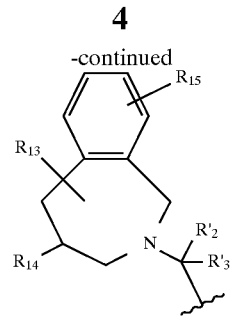

wherein $R'_2$ and $R'_3$ are independently or together H, alkyl, alkylthio, alkylthioalkyl, or cycloalkyl, alkylcycloalkyl, phenyl or phenyl alkyl optionally substituted with guanidine, carboalkoxy, hydroxy, haloalkyl, alkylthio, alkylguanidine, dialkylguanidine, or amidine;

$R_{13}$ is H, alkyl, halo, alkoxy, carboalkoxy, cycloalkoxy, carboxyl, alkylthio, amino, alkylamino, dialkylamino, or aryl, fused aryl or cycloalkyl optionally comprising 1 or more heteroatoms selected from O, N and S, and optionally substituted with halo or alkyl;

$R_{14}$ is H, aminoalkyl, alkenyl, or cycloalkyl, aryl, arylalkyl, or fused aryl-cycloalkyl optionally comprising 1 or more heteroatoms selected from O, N, and S and optionally substituted with alkyl, halo, alkoxy, amino, alkylamino, dialkylamino, carboxy, alkenyl, alkynyl, haloalkoxy, carboalkoxy, alkylcarboxamido, aryl, arylcarboxamido, alkylthio or haloalkylthio; and $R_{15}$ is H, alkyl, halo, alkoxy, carboalkoxy, cycloakloxy, carboxyl, alkylthio, amino, alkylamino, dialkylamino, or aryl, fused aryl or cycloalkyl optionally comprising 1 or more heteroatoms selected from O, N, or S.

In a preferred embodiment, X is N and Y is O. In another preferred embodiment, X is O and Y is N. In a particular embodiment of the invention, $R_{13}$ is phenyl, benzyl or H; $R_{14}$ is $-NH_2$; and $R_{15}$ is H.

Preferably, $R_2$ is isopropyl and $R_3$ is H.

In a preferred embodiment of the invention, $R_1$ is optionally substituted benzyl, preferably selected from methylbenzyl, 3,4-methylenedioxybenzyl or trifluoromethylbenzyl. Alternatively, benzyl is substituted with dialkylamino, preferably dimethylamino. In yet another embodiment, $R_1$ is methylenenaphthyl or an alkyl group, preferably methyl.

The present invention also provides compounds of the formula (Group III):

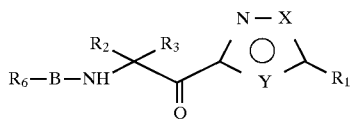

wherein X, Y, $R_1$, $R_2$, $R_3$ and B are as described above; and $R_6$ is

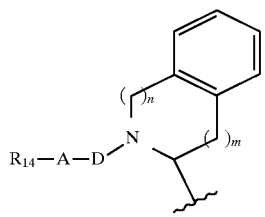

where m is 0 or 1; n is 0 or 1;

D is a direct bond or an amino acid selected from proline, isoleucine, cyclohexylalanine, cysteine optionally substituted at the sulfur with alkyl, alkenyl or phenyl optionally substituted with halogen, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio, haloalkyl thio; phenylalanine, indoline-2-carboxylic acid tetrahydrosioquinoline-2-carboxylic acid optionally substituted with alkyl, alkenyl, haloalkenyl, alkynyl, halogen, cyano, nitro, haloalkyl, amino, aminoalkyl, dialkylamino, alkoxyl, haloalkoxy, carbonyl, carboalkoxy, alkylcarboxamide, arylcarboxamide, alkylthio or haloalkythio; tryptophan, valine, norvaline, norleucine, octahydroindole-2-carboxylic acid, lysine optionally substituted at the nitrogen with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused arylcycloalkyl alkyl optionally comprising 1 or more heteroatoms selected from N, O and S;

A is a direct bond, —C(O)—, —NH—C(O)—, —S(O)$_2$—, —OC(O)— or —C—; and $R_{14}$ is H, alkyl, alkenyl or cycloalkyl, aryl, arylalkyl or fused aryl-cycloalkyl optionally comprising 1 or more heteroatoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamido, aryl, arylcarboxamido, alkylthio or haloalkylthio.

Alternatively, $R_6$ is

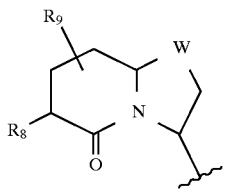

where

W is S or O;
$R_8$ is alkylamino, dialkylamino or amino;
$R_9$ is H, alkyl or halo.

In a preferred embodiment, X is N and Y is O. In another preferred embodiment, X is O and Y is N. According to one embodiment, m is 1, n is 0, and preferably, $R_{14}$ is benzyl, A is —OC(O)— and D is Val.

Preferably, $R_2$ is isopropyl and $R_3$ is H.

In a preferred embodiment of the invention, $R_1$ is optionally substituted benzyl, preferably selected from methylbenzyl, 3,4-methylenedioxybenzyl or trifluoromethylbenzyl. Alternatively, benzyl is substituted with dialkylamino, preferably dimethylamino. In yet another embodiment, $R_1$ is methylenenaphthyl or an alkyl group, preferably methyl.

The present invention further provides compounds of the formula (Group IV):

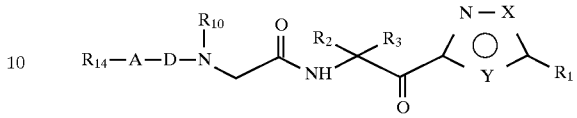

wherein

X, Y, $R_2$ and $R_3$ are as described above;

$R_{10}$ is $(C_5-C_6)$aryl, $(C_5-C_6)$arylalkyl, $(C_5-C_6)$arylalkenyl, cycloalkyl, arylcycloalkyl optionally comprising one or more heteroatoms selected from N, S, or non-peroxide O, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamido, alkylthio or haloalkylthio;

D is a direct bond, —C(O), or an amino acid selected from proline, isoleucine, cyclohexylalanine, cysteine optionally substituted at the sulfur with alkyl, alkenyl or phenyl optionally substituted with halogen, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio, haloalkyl thio; phenylalanine, indoline-2-carboxylic acid, tetrahydroisoquinoline-2-carboxylic acid optionally substituted with alkyl, alkenyl, haloalkenyl, alkynyl, halogen, cyano, nitro, haloalkyl, amino, aminoalkyl, dialkylamino, alkoxyl, haloalkoxy, carbonyl, carboalkoxy, alkylcarboxamide, arylcarboxamide, alkylthio or haloalkylthio; tryptophan, valine, norvaline, norleucine, octahydroindole-2-carboxylic acid or lysine optionally substituted at the nitrogen with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused aryl-cycloalkyl alkyl optionally comprising 1 or more heteroatoms selected from N, O and S;

A is a direct bond, —C(O)—, —NH—C(O)—, —S(O)$_2$—, —OC(O)NH—, —OC(O)— or —C—; and $R_{14}$ is as described above.

In a preferred embodiment, X is N and Y is O. In another preferred embodiment, X is O and Y is N. Preferably, D is Val, A is —OC(O)— and $R_{14}$ is benzyl. In a preferred embodiment, $R_{10}$ is $(C_5-C_6)$aryl or $(C_5-C_6)$arylalkyl, preferably benzyl. According to another preferred embodiment, D is —C(O), and $R_{14}$—A is pyrrole.

Preferably, $R_2$ is isopropyl and $R_3$ is H.

In a preferred embodiment of the invention, $R_1$ is optionally substituted benzyl, preferably selected from methylbenzyl, 3,4-methylenedioxybenzyl or trifluoromethylbenzyl. Alternatively, benzyl is substituted with dialkylamino, preferably dimethylamino. In yet another embodiment, $R_1$ is methylenenaphthyl or an alkyl group, preferably methyl.

The present invention additionally provides compounds of the formula (Group V):

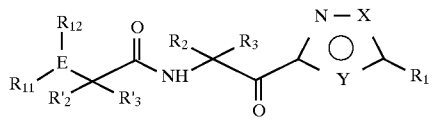

wherein

X, Y, $R_1$, $R_2$, $R_3$, $R'_2$ and $R'_3$ are as described above; and $R_{11}$, $R_{12}$ and E together form a monocyclic or bicyclic ring comprising 5–10 atoms selected from C, N, S and O; said ring containing 1 or more keto groups; and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamido, alkylthio, haloalkylthio; cycloalkyl, alkylcycloalkyl, alkenylcycloalkyl, ($C_5$-$C_{12}$)aryl, ($C_5$-$C_{12}$)arylalkyl, (($C_5$-$C_{12}$)arylalkyl)OC(O)NH— or ($C_5$-$C_{12}$)arylalkenyl optionally comprising one or more heteroatoms selected from N, S, or non-peroxide O, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, —C(O)O(alkyl), —C(O)(alkyl), alkylcarboxamido, alkylthio or haloalkylthio.

In a preferred embodiment, X is N and Y is O. In another preferred embodiment, X is O and Y is N.

Preferably, $R_2$ is isopropyl and $R_3$ is H.

In a preferred embodiment of the invention, $R_1$ is optionally substituted benzyl, preferably selected from methylbenzyl, 3,4-methylenedioxybenzyl or trifluoromethylbenzyl. Alternatively, benzyl is substituted with dialkylamino, preferably dimethylamino. In yet another embodiment, $R_1$ is methylenenaphthyl or an alkyl group, preferably methyl.

According to one embodiment of the invention, R11, R12, and E together form a ring structure of formula (I):

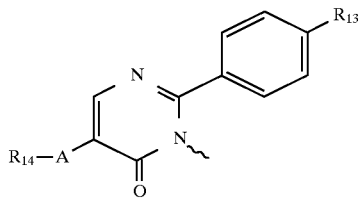

wherein A is as described above;

$R_{13}$ is H, alkyl, halo, alkoxy, carboalkoxy, cycloakloxy, carboxyl, alkylthio, amino, alkylamino, dialkylamino, or aryl, fused aryl or cycloalkyl optionally comprising 1 or more heteroatoms selected from O, N and S, and optionally substituted with halo or alkyl; and $R_{14}$ is H, alkyl, alkenyl or cycloalkyl, aryl, arylalkyl or fused aryl-cycloalkyl optionally comprising 1 or more heteroatoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamido, aryl, arylcarboxamido, alkylthio or haloalkylthio.

Preferably, $R_{13}$ is halo; $R_{14}$—A is CbzNH or $H_2N$; and $R'_2$ and $R'_3$ are H.

In another embodiment, $R_{11}$, $R_{12}$ and E together form a ring of formula (II)

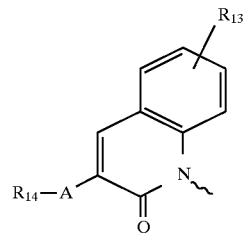

wherein A, $R_{13}$ and $R_{14}$ are as described above;

Preferably, $R'_2$ and $R'_3$ are H. According to one embodiment, $R_{13}$ is piperidinyl; and $R_{14}$—A is CbzNH. Alternatively, $R_{13}$ is H; and $R_{14}$—A is amino, alkylamino or dialkylamino. In another preferred embodiment, $R_{13}$ is halo; and $R_{14}$—A is $CH_3$—O—C(O)—. In yet another embodiment, $R_{13}$ is H; and $R_{14}$—A is CbzNH.

According to another embodiment of the invention, $R_{11}$, $R_{12}$ and E form a ring of formula (III) or (IV):

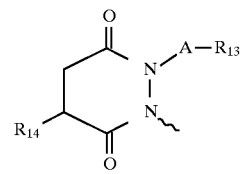

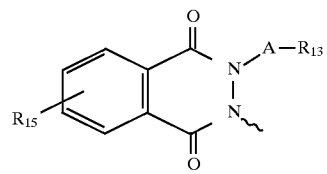

wherein

A is a direct bond, —C— or —C(O)—;

$R_{13}$, $R_{14}$ and $R_{15}$ are as defined above.

According to a particular embodiment, $R_{11}$, $R_{12}$ and E form a ring of formula (III); and —A—$R_{13}$ is —C(O) phenyl; $R_{14}$ is H; and $R'_2$ and $R'_3$ are H.

In another embodiment, $R_{11}$, $R_{12}$ and E form a ring of formula (IV); and —A—$R_{13}$ is —C(O)phenyl; $R_{15}$ is H; and $R'_2$ and $R'_3$ are H.

In another embodiment of the invention, R11, R12 and E form a ring of formula (V):

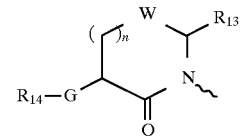

wherein

W is S, SO or C;

n is 0, 1 or 2;

$R_{13}$ and $R_{14}$ are defined above; and

G is —NHC(O)—, —OC(O)NH—, —C(O)—, —NHS$(O)_2$— or a direct bond.

According to one embodiment, n is O and W is S, where preferably $R_{14}$—G is H. Preferably, $R_{13}$ is phenyl.

In another embodiment, n is 1 and W is C. Preferably, $R_{14}$—G is CbzNH—. In a preferred embodiment, $R_{13}$ is phenyl substituted with halo. Preferably, $R'_2$ and $R'_3$ are H.

The invention further provides compounds wherein $R_{11}$, $R_{12}$ and E form a ring of formulas (VI), (VII) or (VIII):

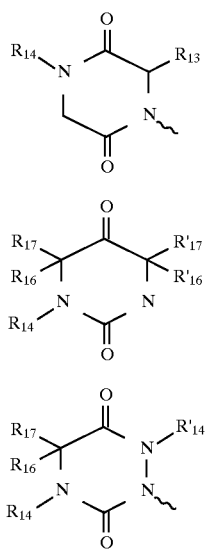

wherein
- R$_{13}$ is as defined above, or is =CHR$_{15}$ or R$_{15}$ where R$_{15}$ is pyridinyl, phenyl or benzyl optionally substituted with halo, dialkylamino or —C(O)OCH$_3$;
- R$_{14}$ and R'$_{14}$ are independently or together H, alkyl, alkenyl, CH$_3$C(O)— or cycloalkyl, aryl, arylalkyl or fused aryl-cycloalkyl optionally comprising 1 or more heteroatoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamido, aryl, arylcarboxamido, alkylthio or haloalkylthio; and
- R$_{16}$, R$_{17}$, R'$_{16}$ and R'$_{17}$ are independently or together H, alkyl, alkylthio, alkylthioalkyl or cycloalkyl, alkylcycloalkyl, phenyl or phenyl alkyl optionally substituted with guanidine, carboalkoxy, hydroxy, haloalkyl, alkylthio, alkylguanidine, dialkylguanidine or amidine.

Preferred compounds are of formula (VI) where R$_{13}$ is =CHR$_{15}$ or R$_{15}$; and R$_{14}$ is H, alkyl, CH$_3$C(O)— or benzyl optionally substituted with alkyl, halo or alkylamino; and R'$_2$ and R'$_3$ are H. Preferably, R$_{13}$ is =CHR$_{15}$ where R$_{15}$ is phenyl optionally substituted with halo or —C(O)OCH$_3$.

In a further embodiment, R$_{11}$, R$_{12}$ and E form a ring of formula (IX):

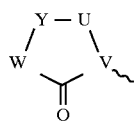

wherein
U, V, W and Y are independently or together N, C, C(O), N(R$_{13}$) where R$_{13}$ is H, alkyl, halo, alkoxy, carboalkoxy, cycloakloxy, carboxyl, alkylthio, amino, alkylamino, dialkylamino, or aryl, fused aryl or cycloalkyl optionally comprising 1 or more heteroatoms selected from O, N and S, and optionally substituted with halo or alkyl; N(R$_{14}$) where R$_{14}$ is H, alkyl, alkenyl, or cycloalkyl, aryl, arylalkyl or fused aryl-cycloalkyl optionally comprising 1 or more heteroatoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamido, aryl, arylcarboxamido, alkylthio or haloalkylthio; or C(R$_{16}$)(R$_{17}$) where R$_{16}$ and R$_{17}$ are independently or together H, alkyl, alkylthio, alkylthioalkyl or cycloalkyl, alkylcycloalkyl, phenyl or phenyl alkyl optionally substituted with guanidine, carboalkoxy, hydroxy, haloalkyl, alkylthio, alkylguanidine, dialkylguanidine or amidine.

In one preferred embodiment, U is C(R$_{16}$)(R$_{17}$), V is N, W is N(R$_{14}$) and Y is C(O), where preferably R'$_2$ and R'$_3$ are H; R$_{16}$ is phenyl or benzyl; R$_{17}$ is H; and R$_{14}$ is H or benzyl optionally substituted with alkyl, halo, or alkylamine.

In another preferred embodiment, U is C(O), V is N, W is N(R$_{14}$) and Y is C(R$_{16}$)(R$_{17}$), where preferably R'$_2$ and R'$_3$ are H; R$_{14}$ is H; R$_{16}$ is phenyl; and R$_{17}$ is H.

In yet another preferred embodiment, U is C(O), V is N, W is N(R$_{14}$) and Y is N(R$_{13}$), where preferably R'$_2$ and R'$_3$ are H; R$_{13}$ is phenyl; and R$_{14}$ is H.

The invention further provides compounds of the formula (Group VI):

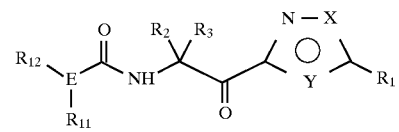

wherein X, Y, R$_1$, R$_2$, R$_3$, R$_{11}$, R$_{12}$ and E are as defined above.

Preferably, R$_{11}$, R$_{12}$ and E together form a ring of formula (X):

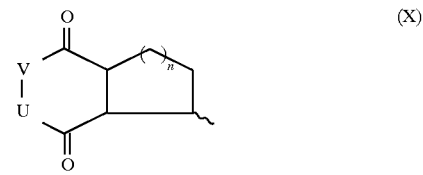

where U and V are independently or together N, C, N(R$_{13}$) where R$_{13}$ is H, alkyl, alkoxy, carboalkoxy, cycloakloxy, carboxyl, alkylthio, amino, alkylamino, dialkylamino, or aryl, fused aryl or cycloalkyl optionally comprising 1 or more heteroatoms selected from O, N and S; or C(R$_{16}$)(R$_{17}$) where R$_{16}$ and R$_{17}$ are as defined above.

As used herein, the term "optionally substituted" means, when substituted, mono to fully substituted.

As used herein, the term "alkyl" means C$_1$–C$_{15}$, however, preferably C$_1$–C$_7$.

As used herein, the term "alkenyl" means C$_1$–C$_{15}$, however, preferably C$_1$–C$_7$.

As used herein, the term "alkynyl" means C$_1$–C$_{15}$, however, preferably C$_1$–C$_7$.

It will be understood that alkyl, alkenyl and alkynyl groups, whether substituted or unsubstituted, may be linear or branched.

As used herein, the term "aryl," unless otherwise stated, means aryl groups preferably comprising 5 to 12 carbons, and more preferably 5 to 6 carbons. As used herein, the term "arylalkyl" includes mono-substituted alkyl groups (e.g., benzyl), as well as di-substituted alkyl groups such as -alkyl(phenyl)$_2$ (e.g., —CH(phenyl)$_2$). As used herein, where the term "arylalkyl" is defined by the general formula (C$_x$–C$_y$)arylalkyl, x and y refer to the number of carbons making up the aryl group. The alkyl group is as defined above.

As used herein, the term "Cbz" means benzyloxycarbonyl.

Pharmaceutically acceptable salts of the compounds described above are within the scope of the invention.

DETAILED DESCRIPTION

Figure 1:
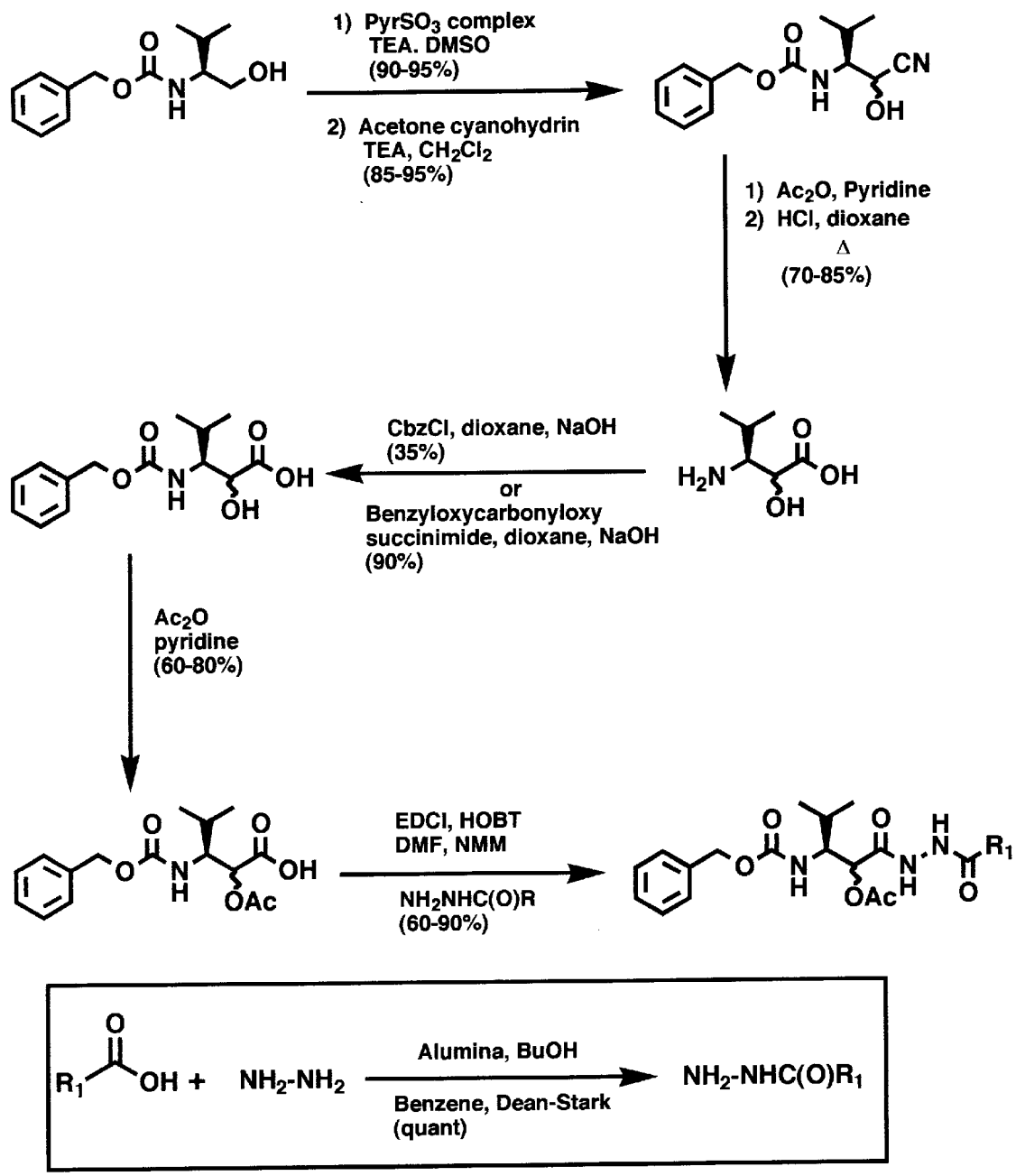
FIG. 1 is a schematic representation of the synthesis of compounds of Group I.

The compounds of the present invention have been found to be potent inhibitors of the serine protease human neutrophil elastase (HNE). They are reversible inhibitors that presumably form a transition state intermediate with the active site serine residue. The compounds are characterized by their low molecular weights, high selectivity with respect to HNE and stability regarding physiological conditions. Therefore, the compounds can be implemented to prevent, alleviate and/or otherwise treat diseases which are mediated by the degradative effects associated with the presence of HNE. Their usage is of particular importance as they relate to various human treatment in vivo but may also be used as a diagnostic tool in vitro.

The compounds of the present invention are not limited to use for inhibition of human elastase. Elastase is a member of the class of enzymes known as serine proteases. This class also includes, for example, the enzymes chymotrypsin, cathepsin G, trypsin and thrombin. These proteases have in common a catalytic triad consisting of Serine-195, Histidine-57 and Aspartic acid-102 (chymotrypsin numbering system). The precise hydrogen bond network that exists between these amino acid residues allows the Serine-195 hydroxyl to form a tetrahedral intermediate with the carbonyl of an amide substrate. The decomposition of this intermediate results in the release of a free amine and the acylated enzyme. In a subsequent step, this newly formed ester is hydrolyzed to give the native enzyme and the carboxylic acid. It is this carboxyl component that helps characterize the specificity for the enzyme. In the example in which the carboxyl component is a peptide, the alpha-substituent of the amino acid is predominately responsible for the specificity toward the enzyme. Utilizing the well accepted subset nomenclature by Schechter and Berger (*Biochem. Biophy. Res. Commun.*, 27, 157 (1967) and *Biochem Biophys. Res. Commun.*, 32, 898 (1968)), the amino acid residues in the substrate that undergo the cleavage are defined as $P_1 \ldots P_n$ toward the N-terminus and $P_1' \ldots P_n'$ toward the C-terminus. Therefore, the scissile bond is between the $P_1$ and the $P_1'$ residue of the peptide subunits. A similar nomenclature is utilized for the amino acid residues of the enzyme that make up the binding pockets accommodating the subunits of the substrate. The difference is that the binding pocket for the enzyme is designated by $S_1 \ldots S_n$ instead of $P_1 \ldots P_n$ as for the substrate.

The characteristics for the $P_1$ residue defining serine proteinase specificity is well established. The proteinases may be segregated into three subclasses: elastases, chymases and tryptases based on these differences in the $P_1$ residues. The elastases prefer small aliphatic moieties such as valine whereas the chymases and tryptases prefer large aromatic hydrophobic and positively charged residues respectively.

One additional proteinase that does not fall into one of these categories is prolyl endopeptidase. The $P_1$ residue defining the specificity is a proline. This enzyme has been implicated in the progression of memory loss in Alzheimer's patients. Inhibitors consisting of α-keto heterocycles have recently been shown to inhibit prolyl endopeptidase; Tsutsumi et al., *J. Med. Chem.*, 37, 3492–3502 (1994). By way of extension, α-keto heterocycles as defined by Formula I allow for an increased binding in P' region of the enzyme.

TABLE 1

$P_1$ Characteristics for Proteinase Specificity

| PROTEINASE | REPRESENTATWE | $P_1$ |
|---|---|---|
| Elastases | Human Neutrophil Elastase | small aliphatic residues |
| Chymases | alpha-Chymotrypsin, Cathepsin G | aromatic or large hydrophobic residues |
| Tryptases | Thrombin, Tryptin, Urokinase, Plasma Killikrein, Plasminogen Activator, Plasmin | positively charged residues |
| Other | Prolyl, Endopeptidase | proline |

Since the $P_1$ residue predominately defines the specificity of the substrate, the present invention relates to $P_1$–$P_n'$ modifications, specifically, certain alpha-substituted ketoheterocycles composed of 1,3,4 oxadiazoles, 1,2,4-oxadiazoles, 1,3,4-thiadiazoles, 1,2,4-thiadiazoles, 1-substituted, and 4-substituted 1,2,4-triazoles. By altering the alpha-substituent and the substituent on the heterocycle, the specificity of these compounds can be directed toward the desired proteinase (e.g., small aliphatic groups for elastase).

The efficacy of the compounds for the treatment of various diseases can be determined by scientific methods which are known in the art. The following are noted as examples for HNE mediated conditions:

for acute respiratory distress syndrome, the method according to Human neutrophil elastase (HNE) model (*AARD*, 141, 227–677 (1990)), or the Endotoxin induced acute lung injury model in minipigs (*AARD*, 142, 782–788 (1990)) may be used;

in ischemia/reperfusion, the method according to the canine model of reperfusion injury (*J. Clin. Invest.*, 81, 624–629 (1988)) may be used.

Figure 2:
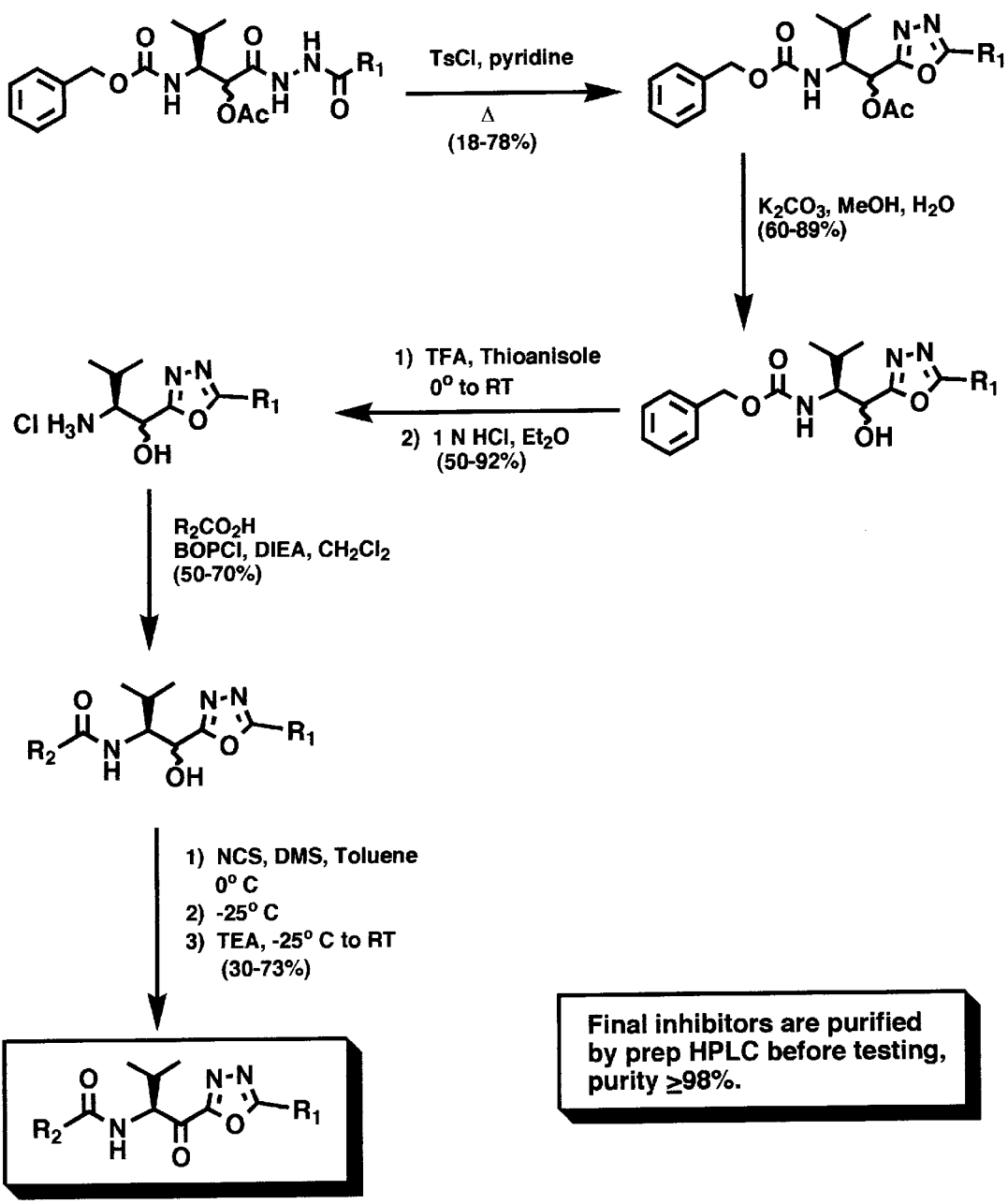
FIG. 2 is a schematic representation of the synthesis of compounds of Group I.
Figure 3:
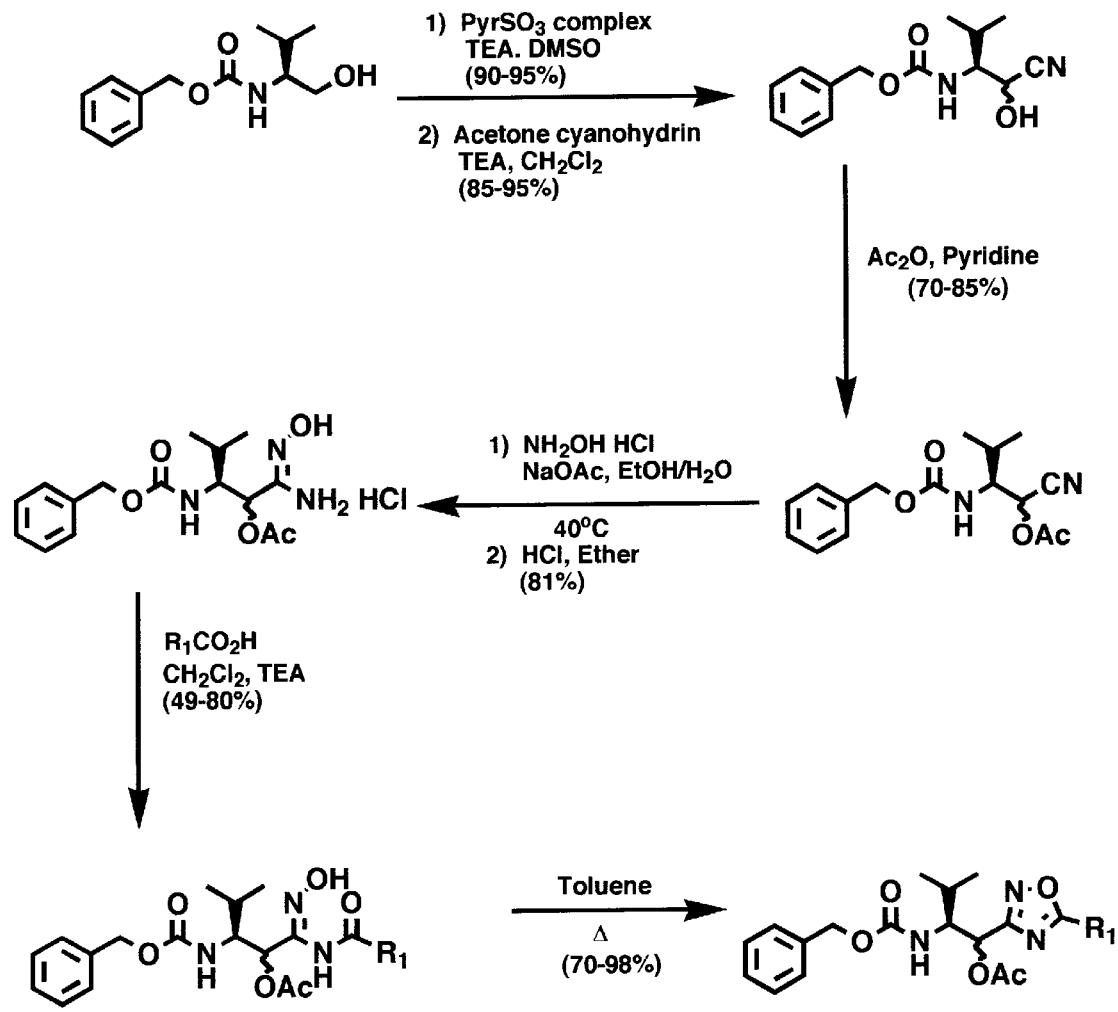
FIG. 3 is a schematic representation of the synthesis of compounds of Group I.
Figure 4:
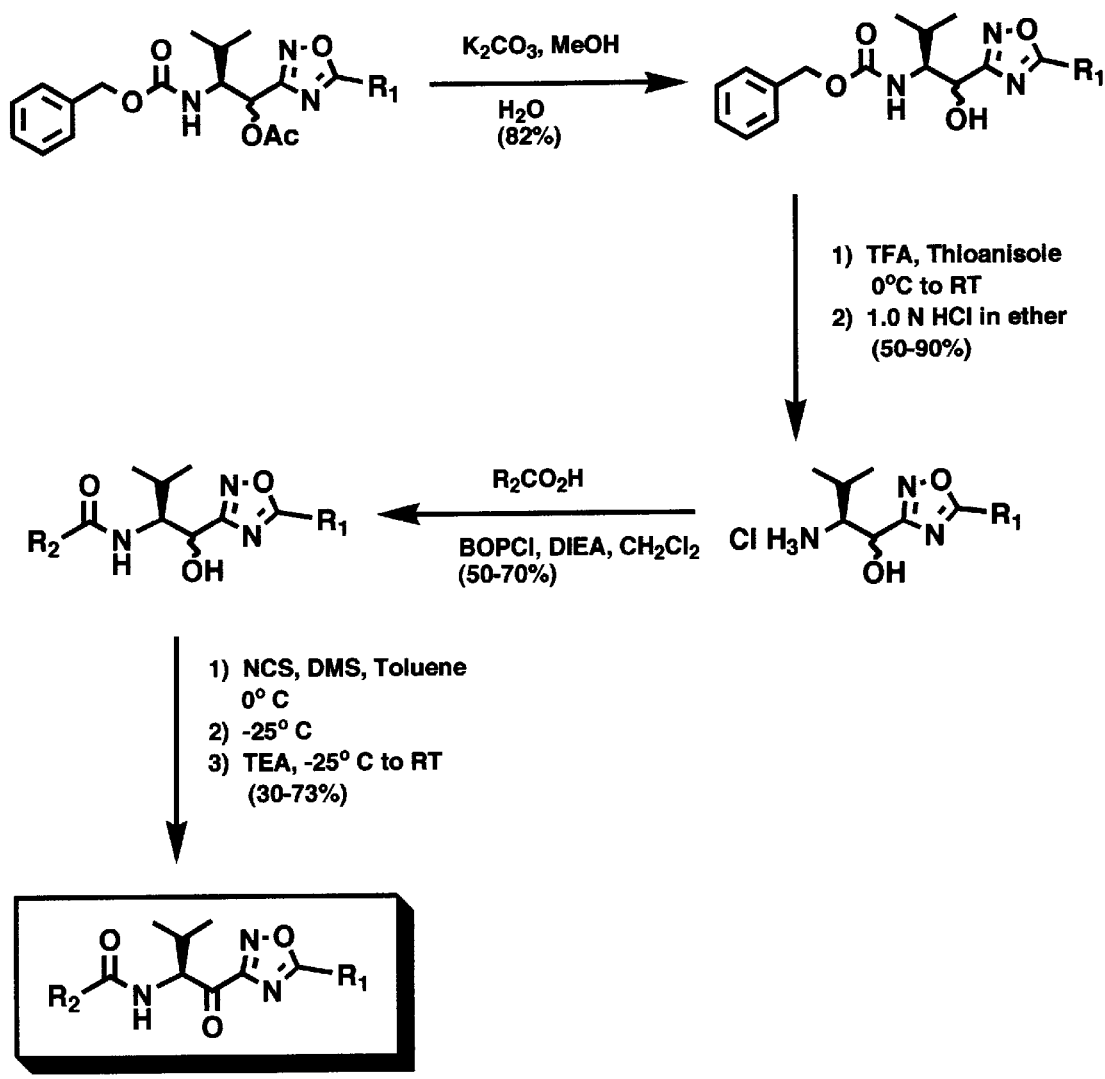
FIG. 4 is a schematic representation of the synthesis of compounds of Group I.
Figure 5:
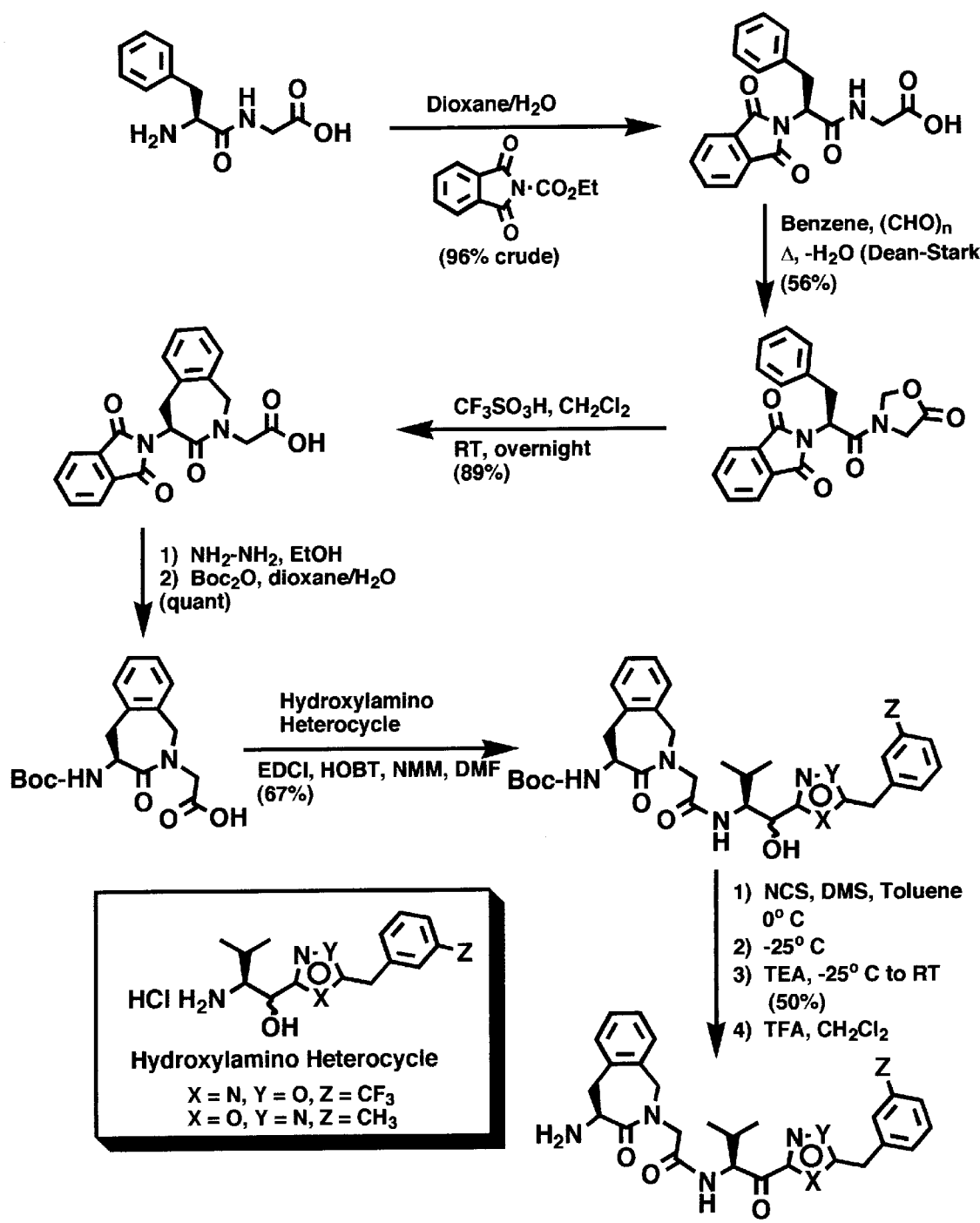
FIG. 5 is a schematic representation of the synthesis of compounds of Group II.
Figure 6:
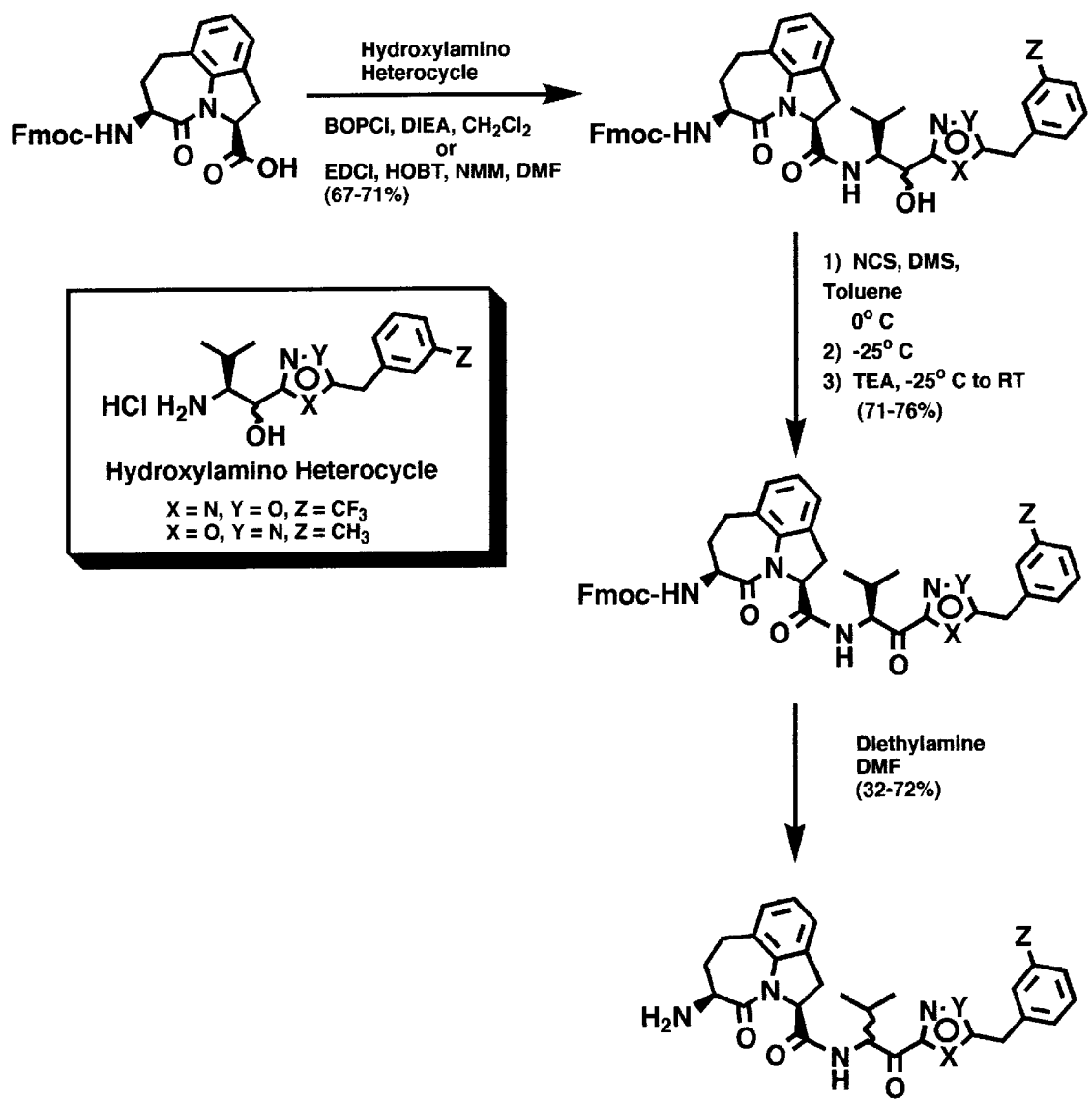
FIG. 6 is a schematic representation of the synthesis of compounds of Group II.
Figure 7:
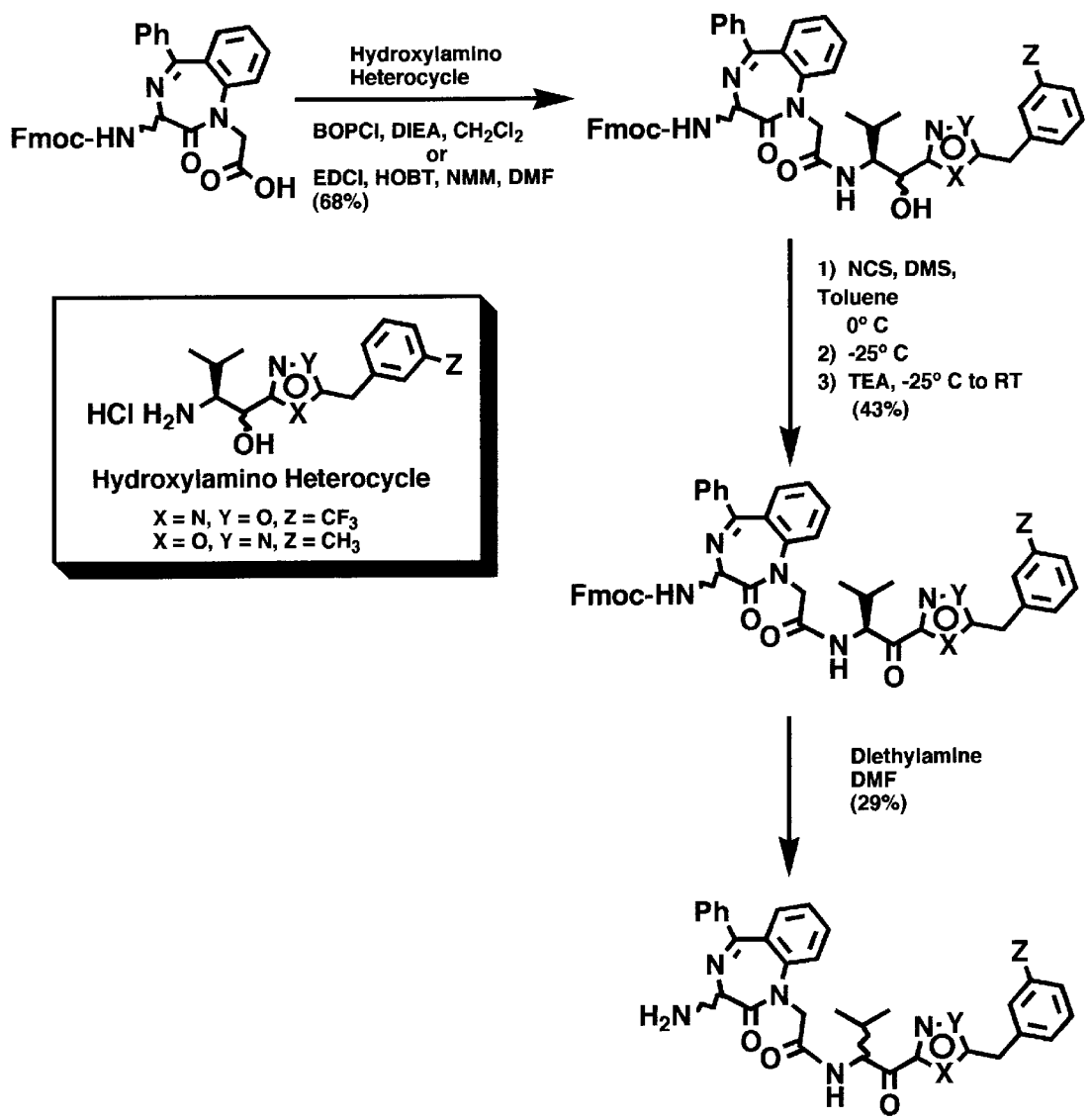
FIG. 7 is a schematic representation of the synthesis of compounds of Group II.
Figure 8:
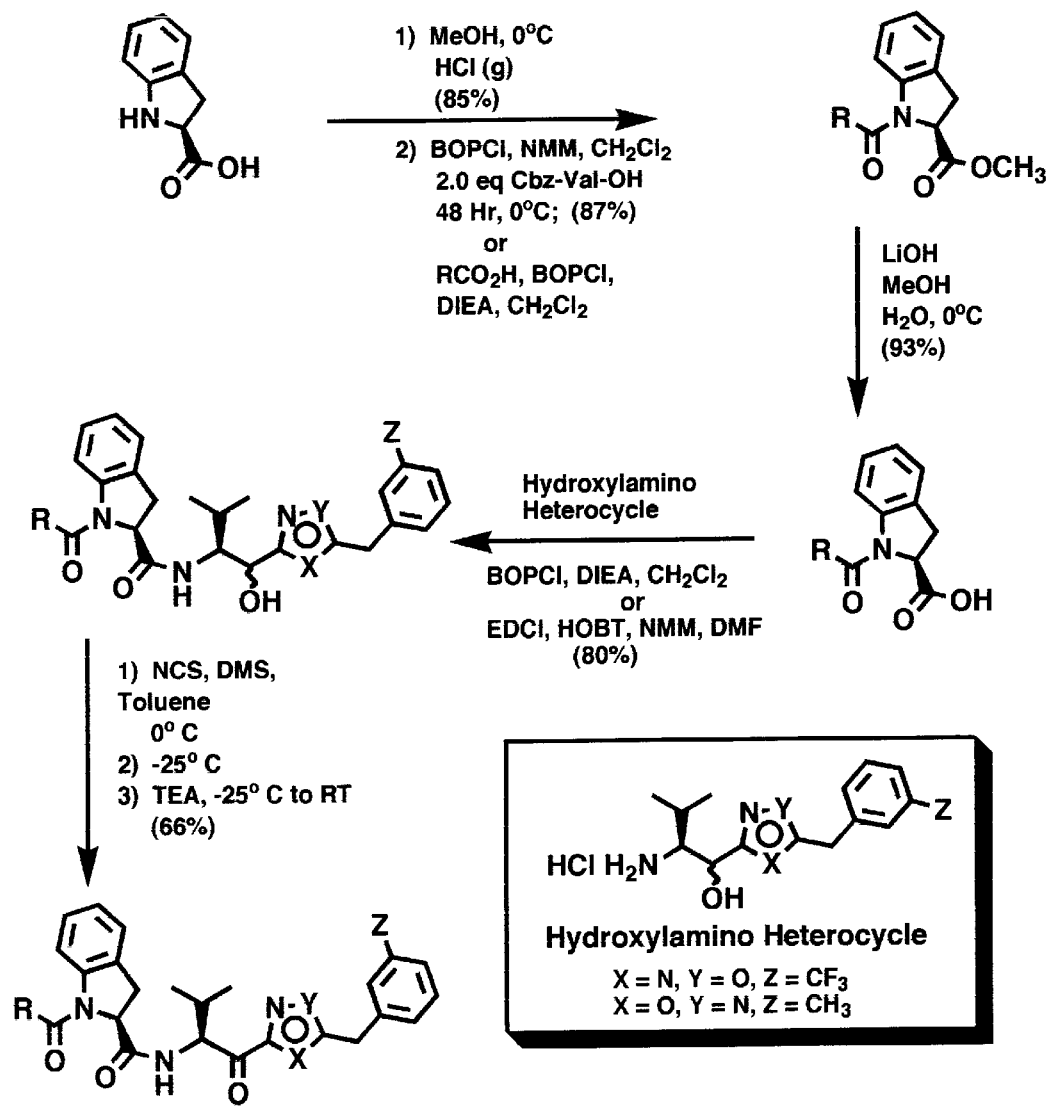
FIG. 8 is a schematic representation of the synthesis of compounds of Group III.
Figure 9:
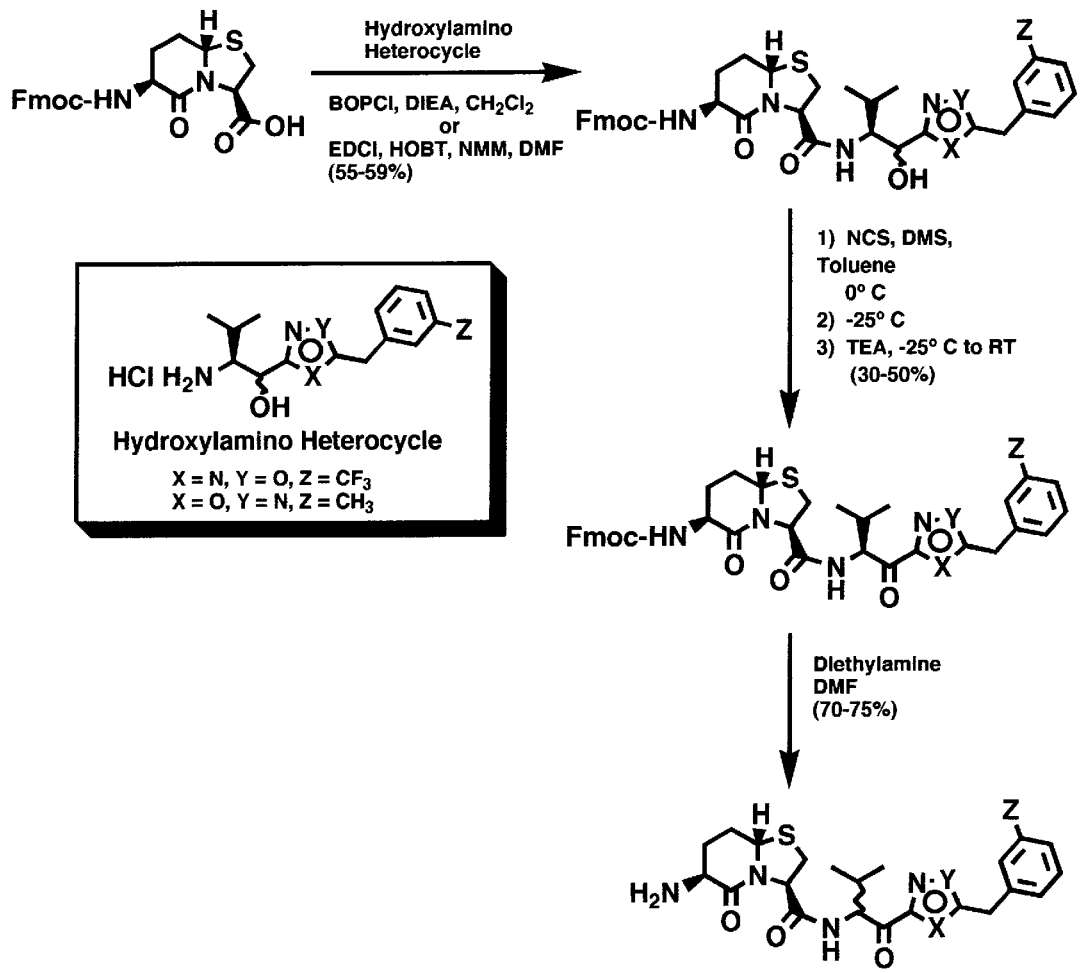
FIG. 9 is a schematic representation of the synthesis of compounds of Group III.
Figure 10:
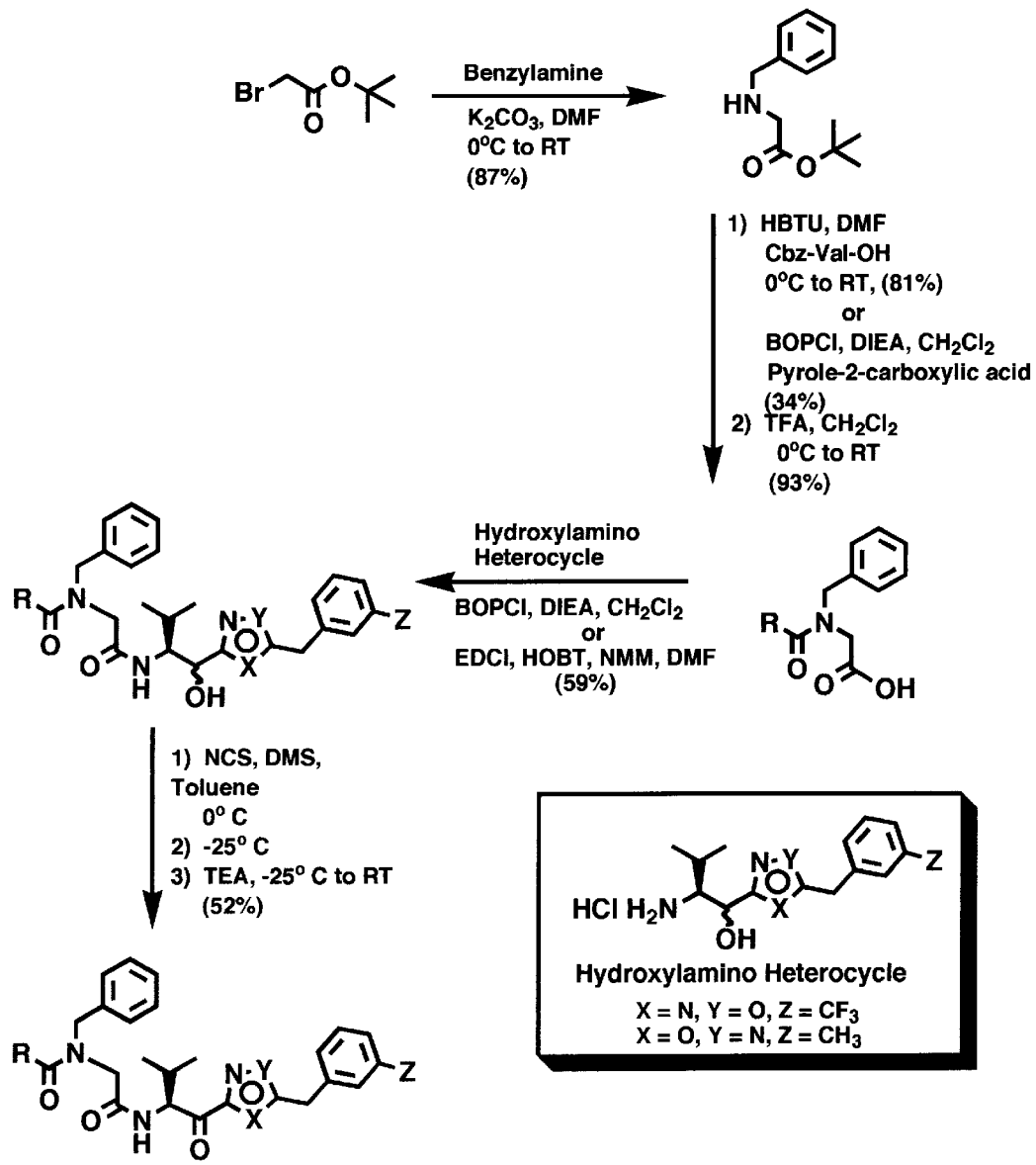
FIG. 10 is a schematic representation of the synthesis of compounds of Group IV.
Figure 11:
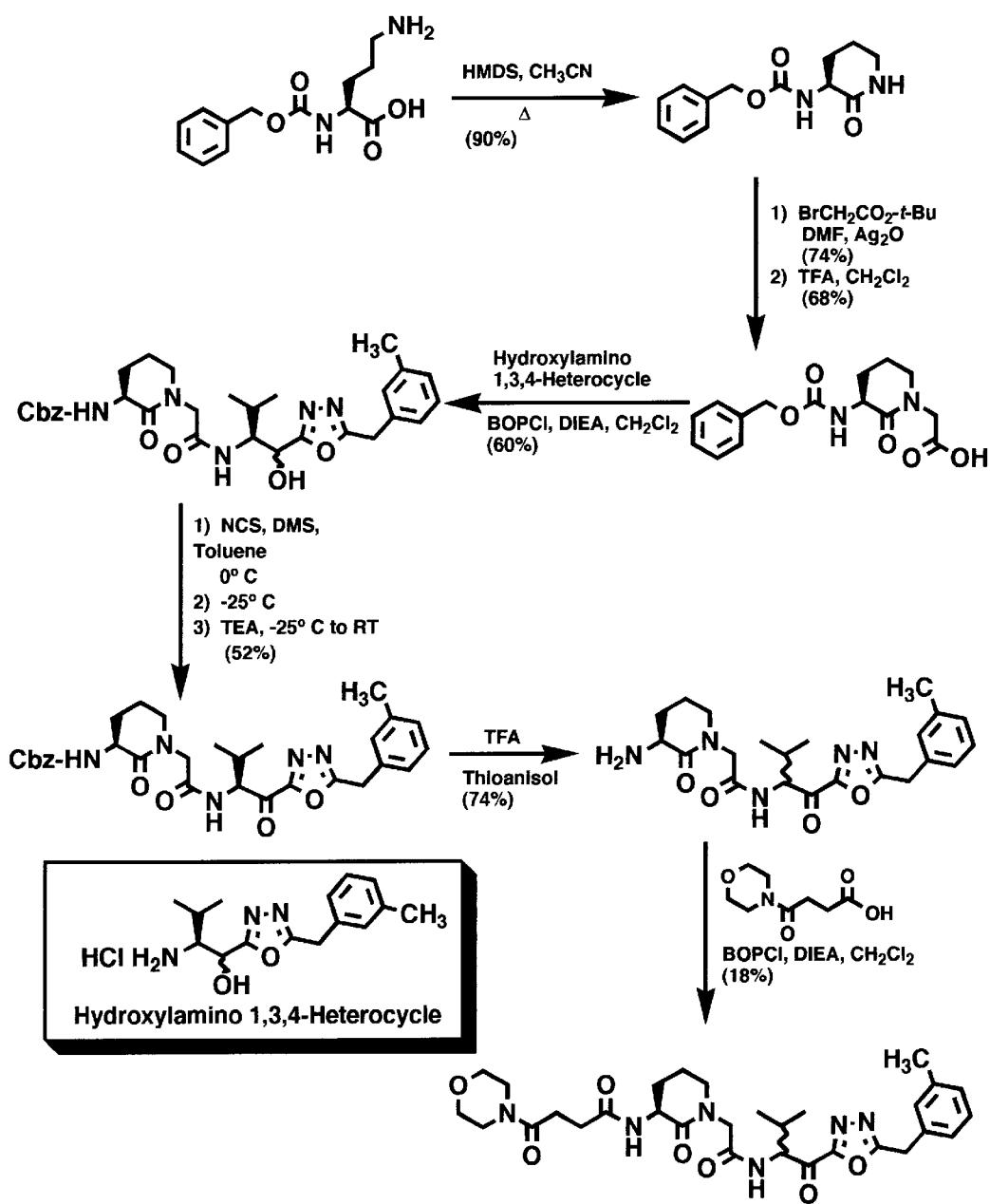
FIG. 11 is a schematic representation of the synthesis of compounds of Group V.
Figure 12:
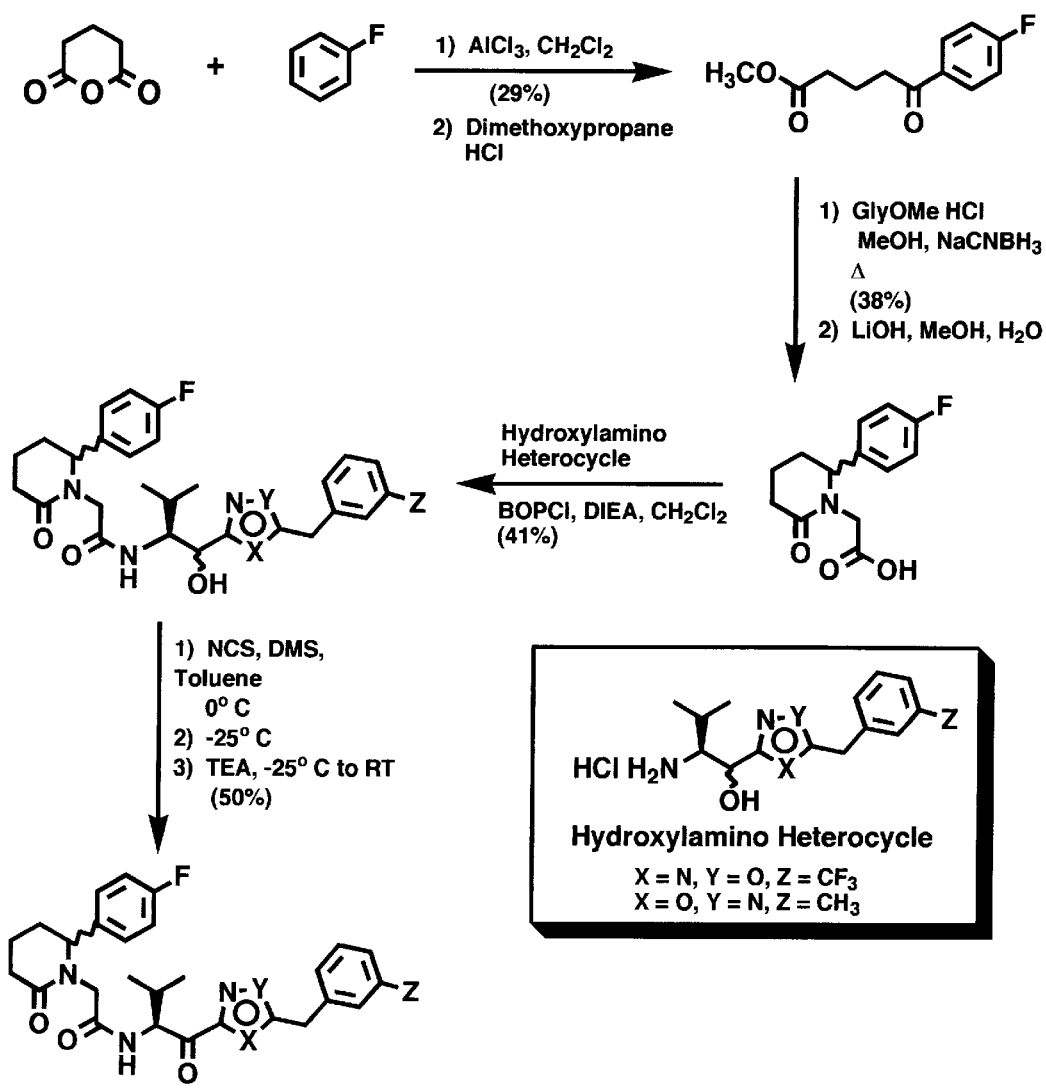
FIG. 12 is a schematic representation of the synthesis of compounds of Group V.
Figure 13:
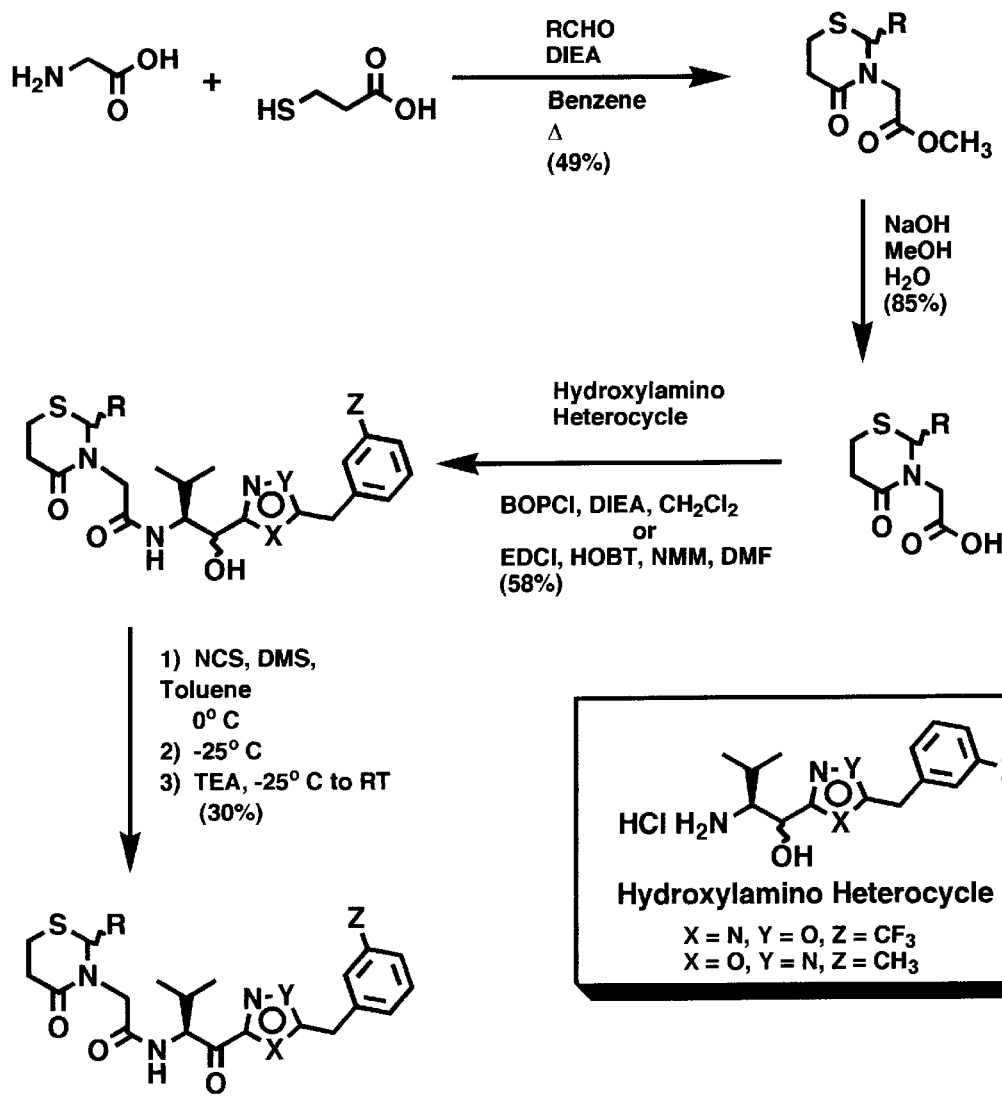
FIG. 13 is a schematic representation of the synthesis of compounds of Group V.
Figure 14:
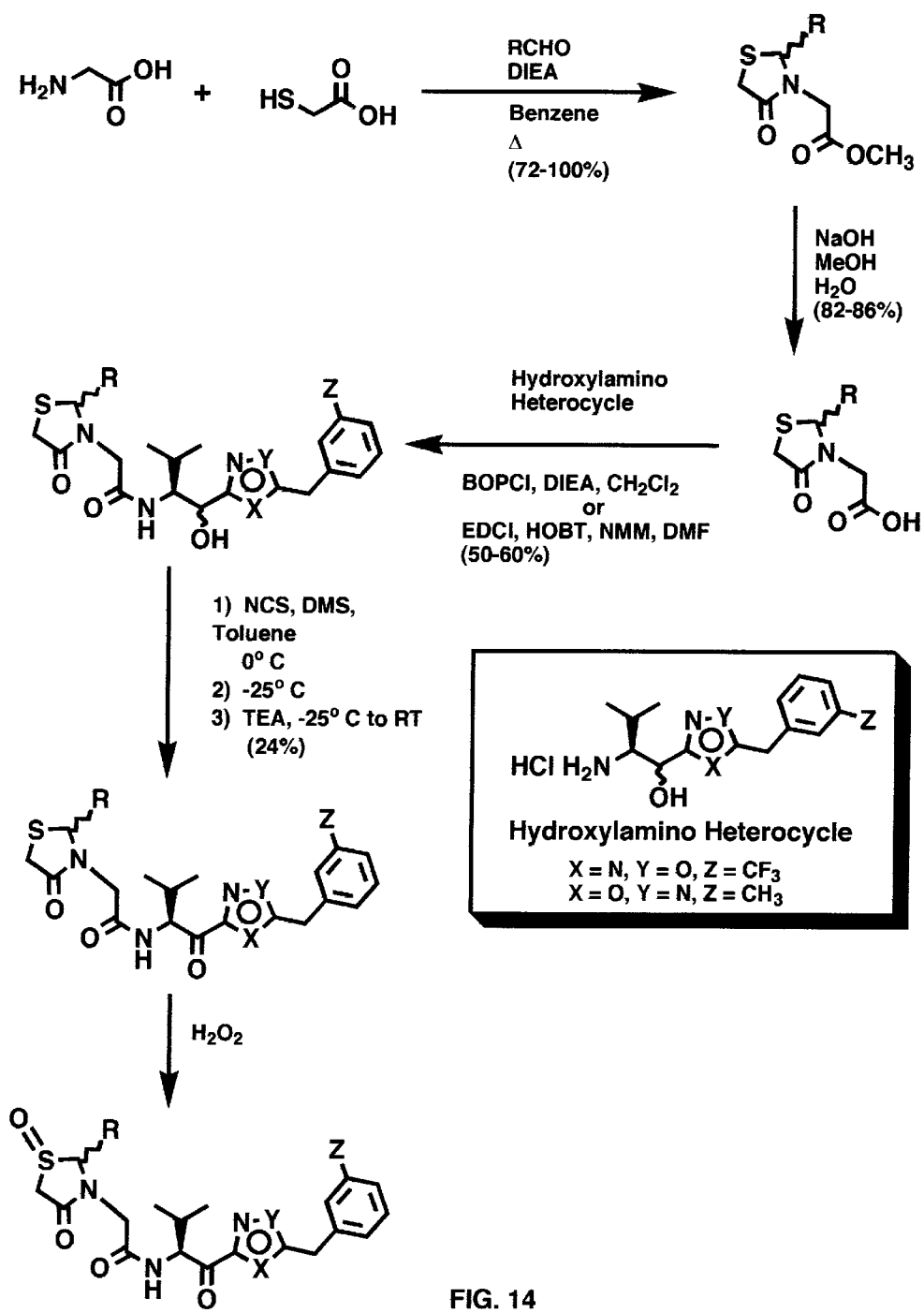
FIG. 14 is a schematic representation of the synthesis of compounds of Group V.
Figure 15:
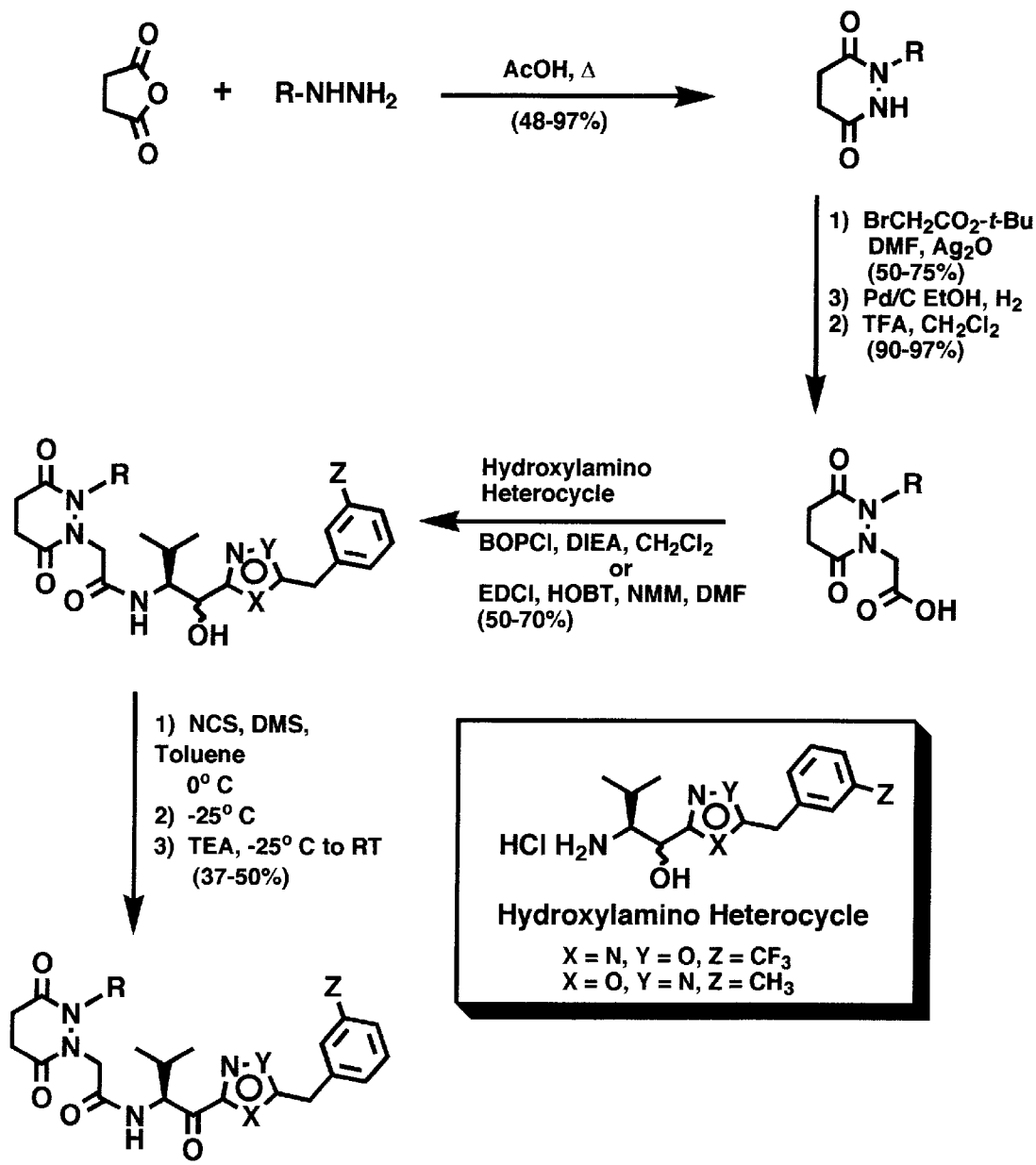
FIG. 15 is a schematic representation of the synthesis of compounds of Group V.
Figure 16:
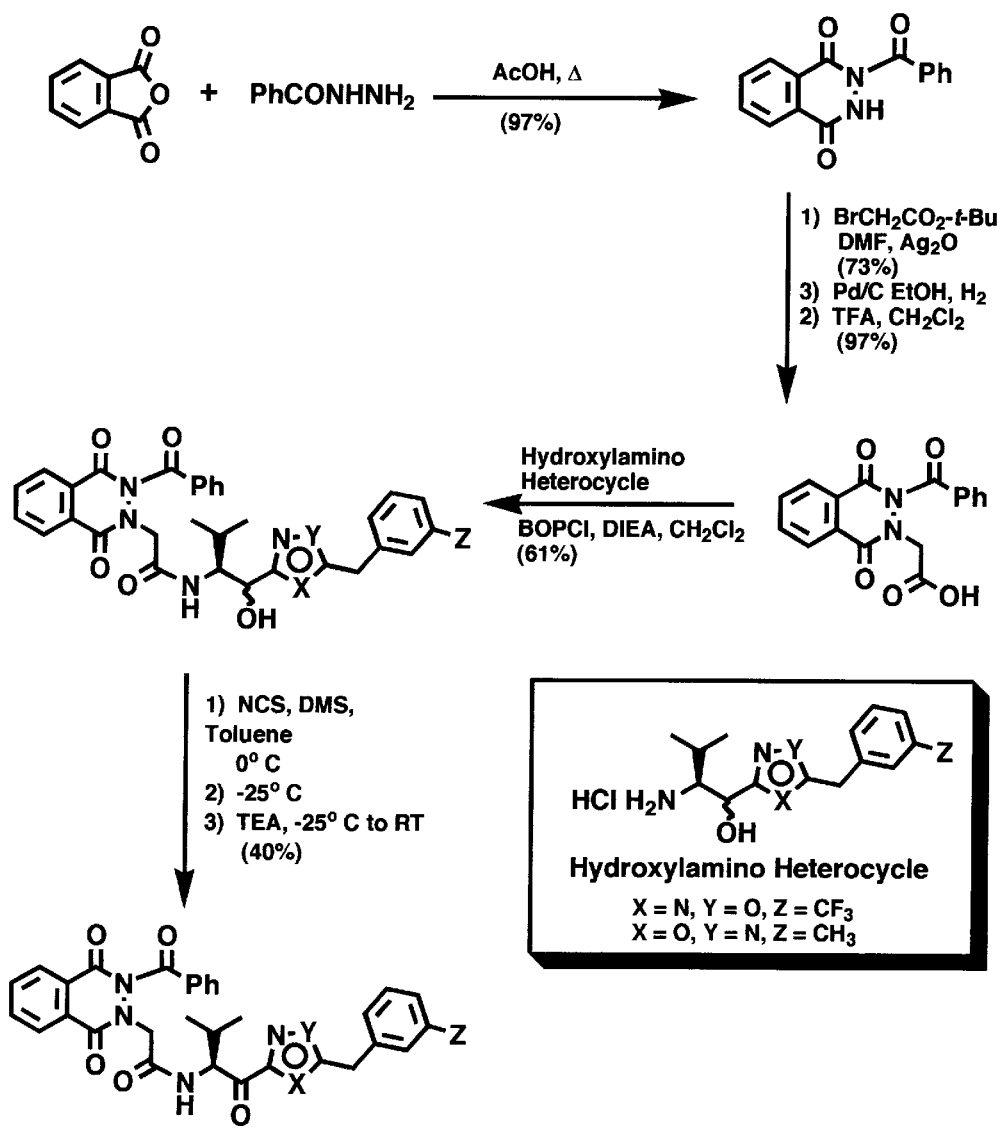
FIG. 16 is a schematic representation of the synthesis of compounds of Group V.
Figure 17:
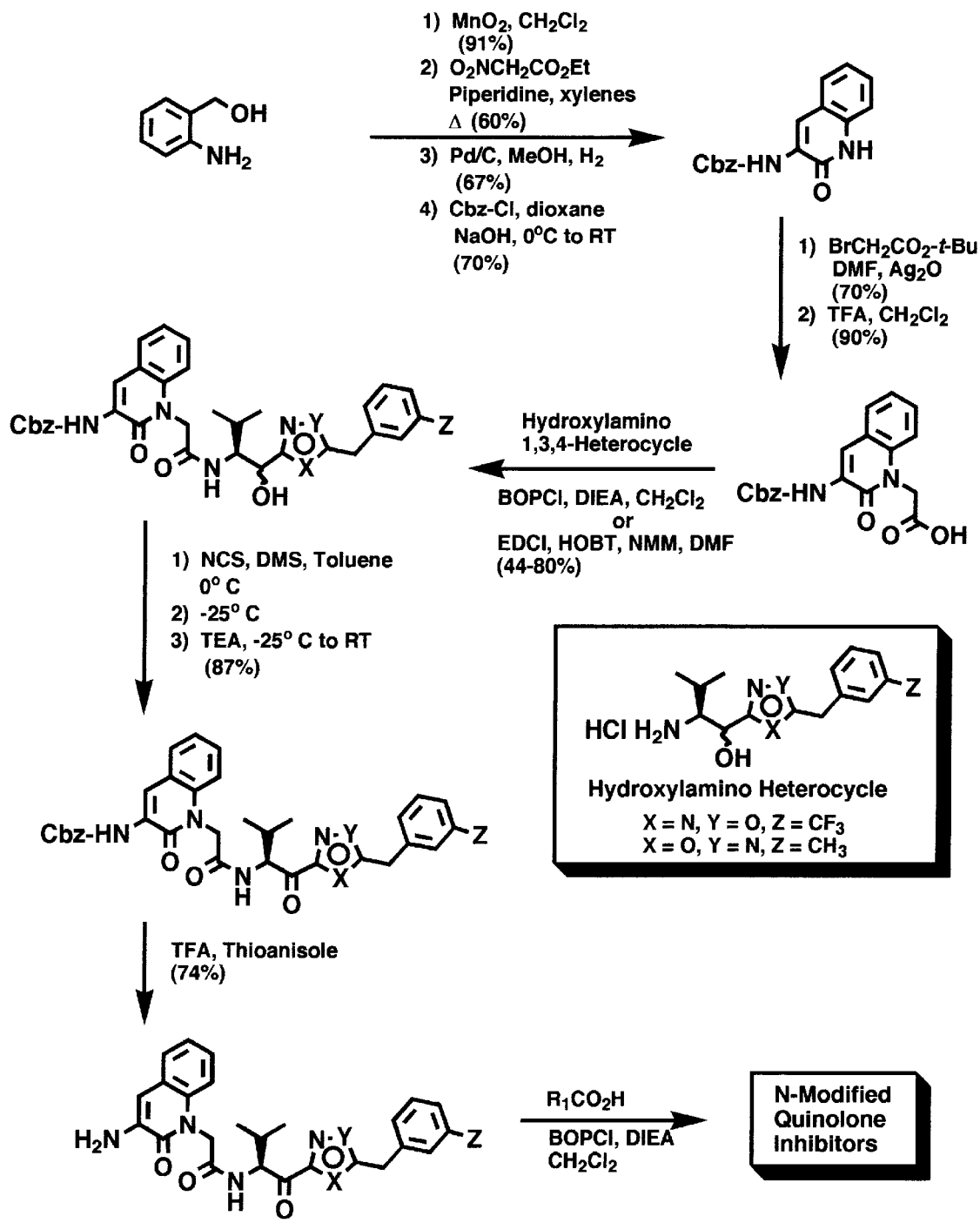
FIG. 17 is a schematic representation of the synthesis of compounds of Group V.
Figure 18:
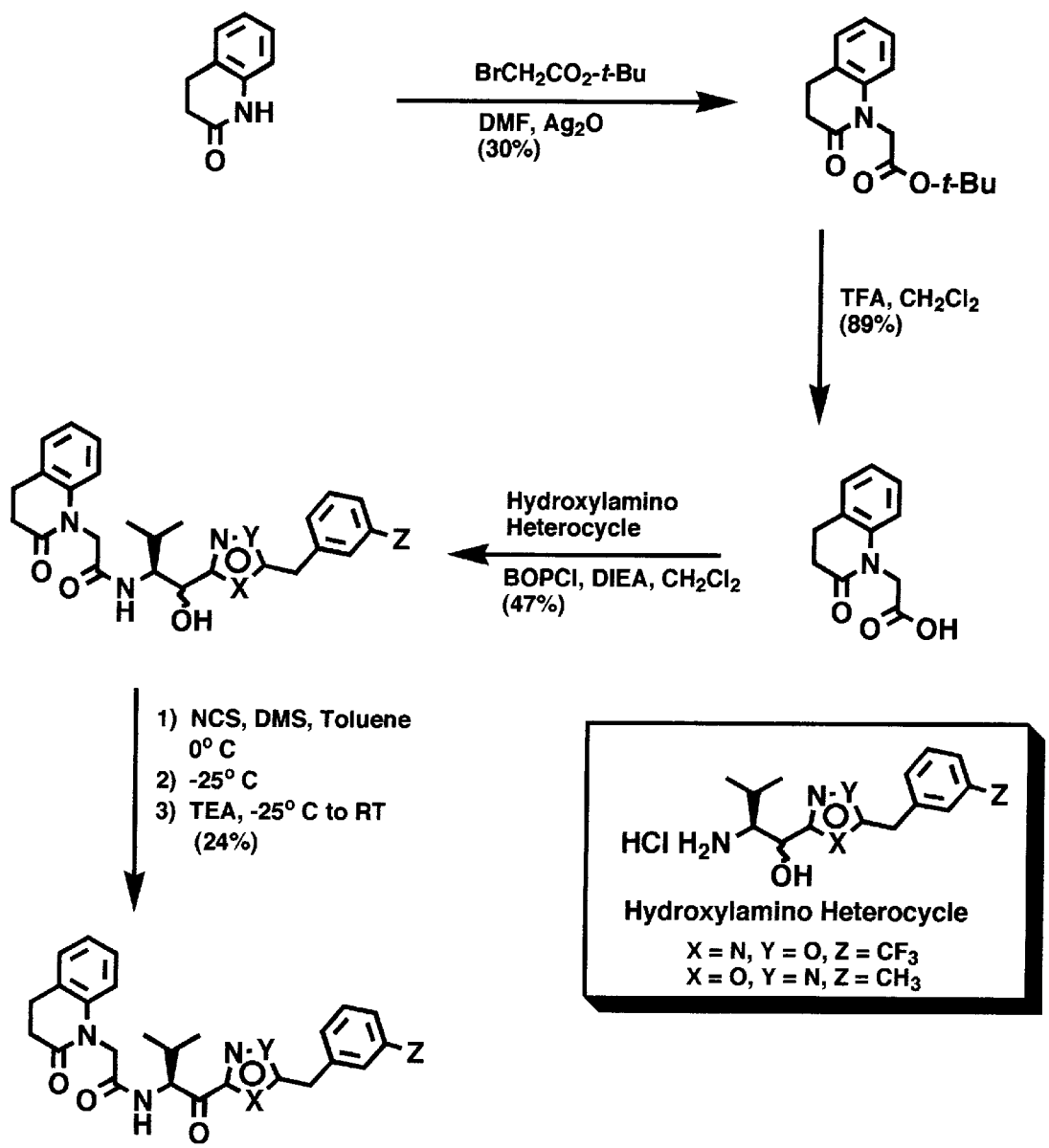
FIG. 18 is a schematic representation of the synthesis of compounds of Group V.
Figure 19:
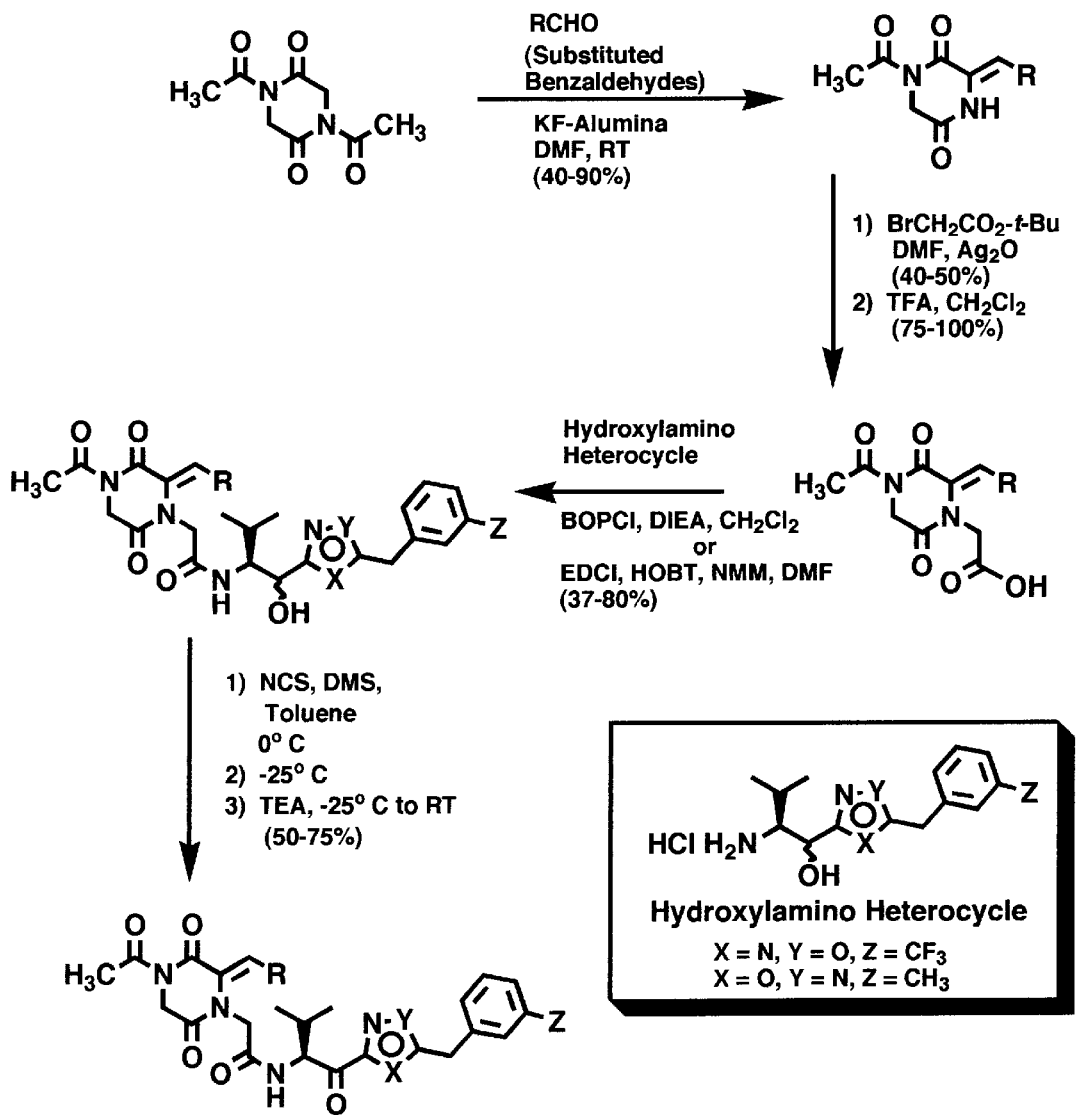
FIG. 19 is a schematic representation of the synthesis of compounds of Group V.
Figure 20:
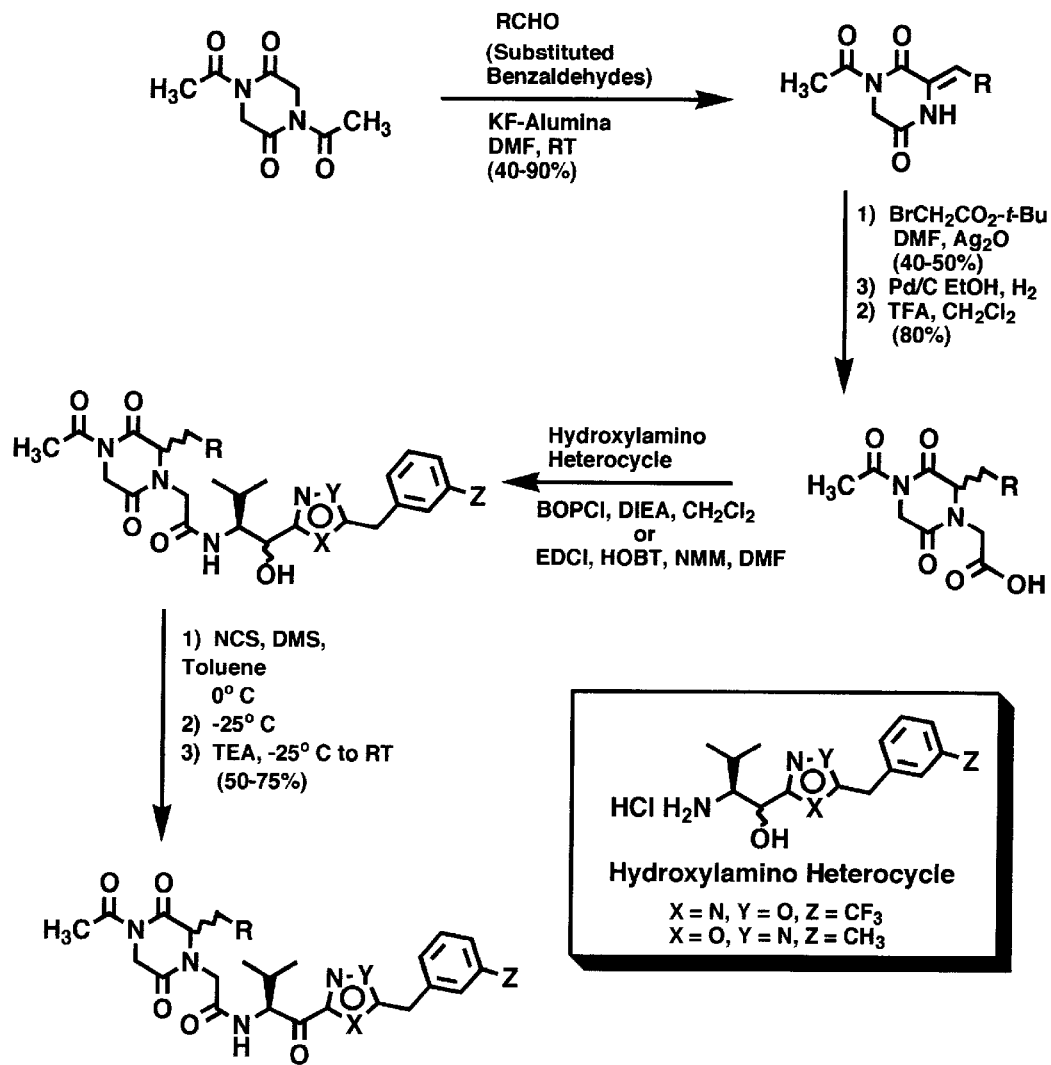
FIG. 20 is a schematic representation of the synthesis of compounds of Group V.
Figure 21:
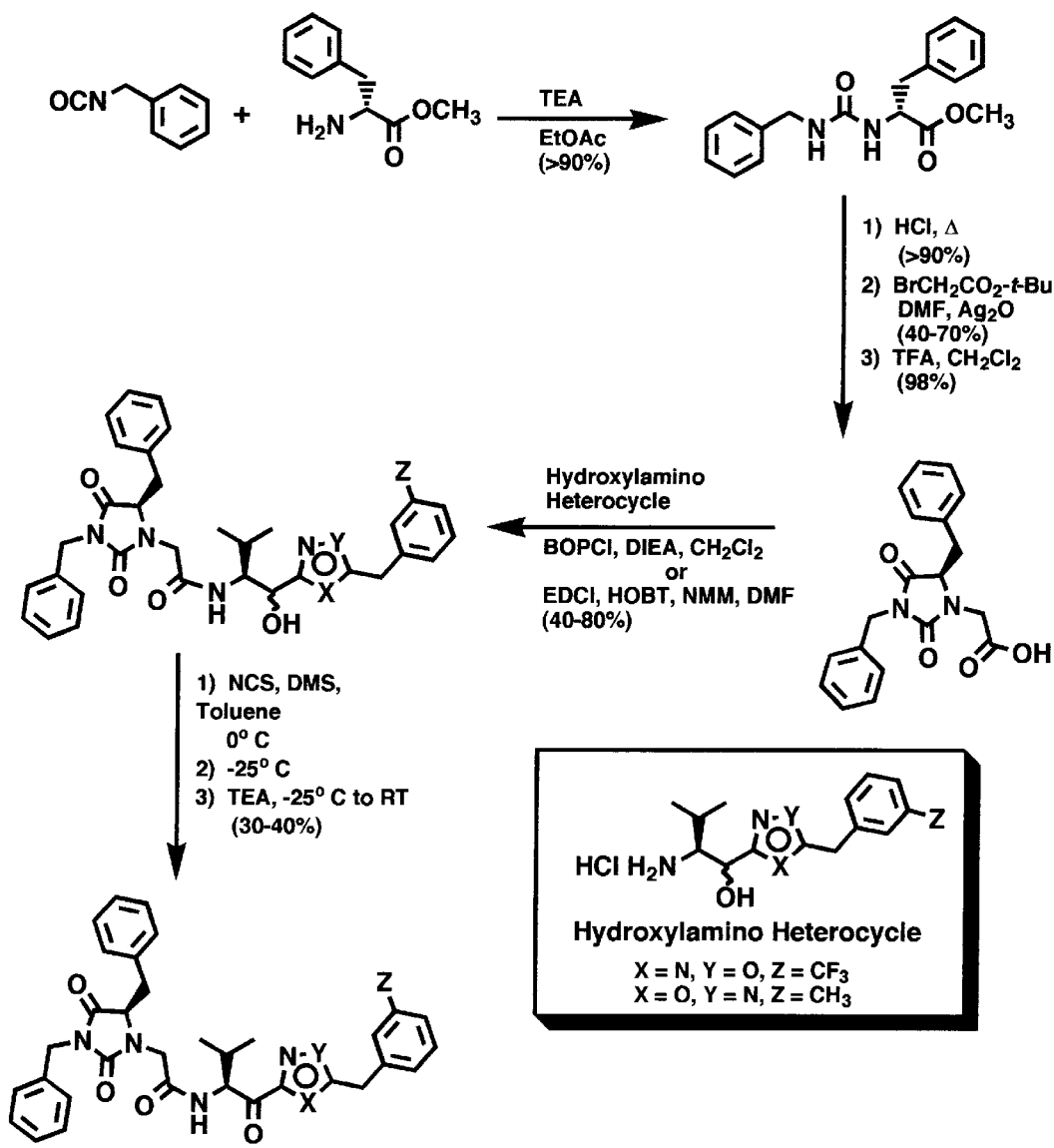
FIG. 21 is a schematic representation of the synthesis of compounds of Group V.
Figure 22:
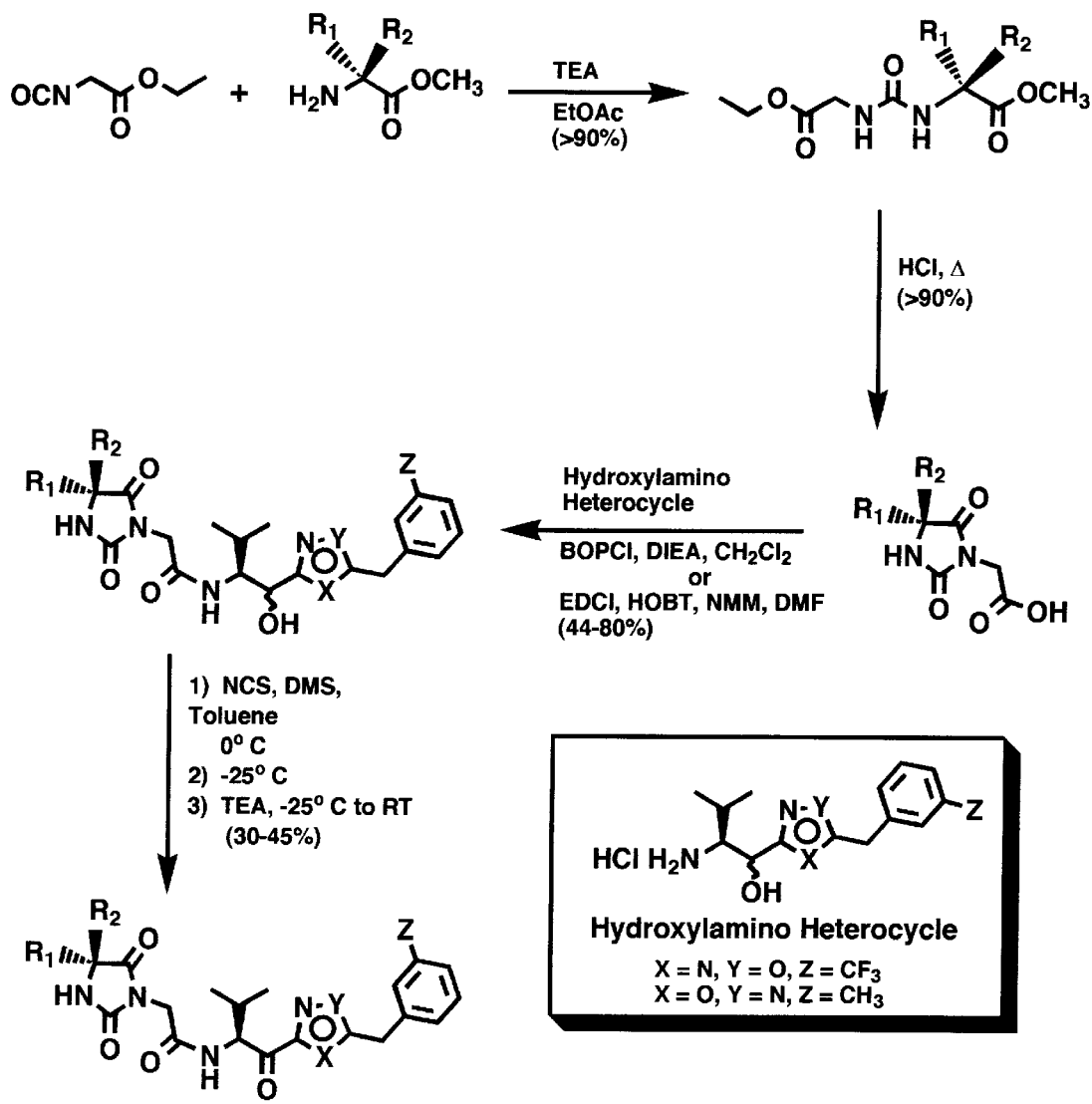
FIG. 22 is a schematic representation of the synthesis of compounds of Group V.
Figure 23:
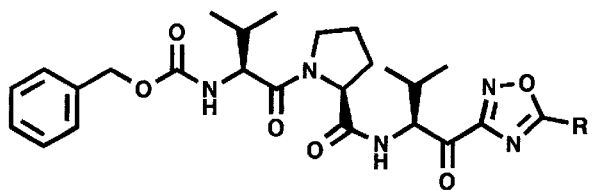
FIG. 23 shows the activity of certain compounds of Group I.
Figure 24:
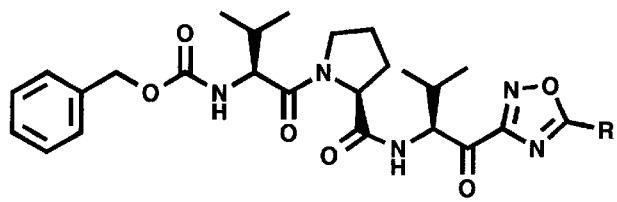
FIG. 24 shows the activity of certain compounds of Group I.
Figure 25:
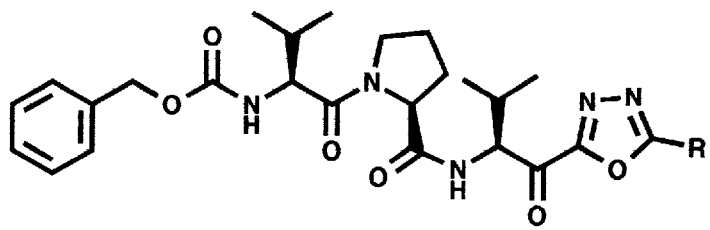
FIG. 25 shows the activity of certain compounds of Group I.
Figure 26:
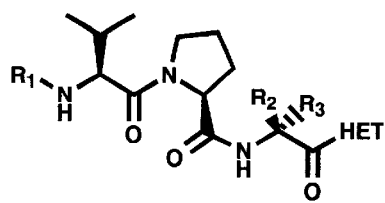
FIG. 26 shows the activity of certain compounds of Group I.
Figure 27:
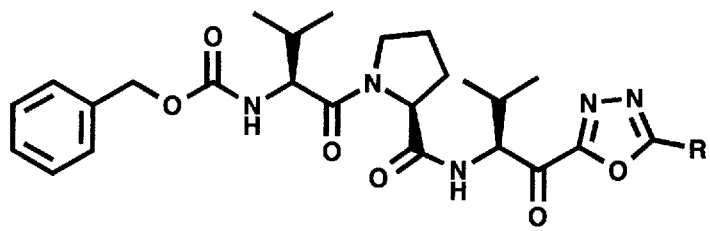
FIG. 27 shows the activity of certain compounds of Group I.
Figure 28:
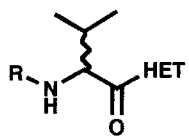
FIG. 28 shows the activity of certain compounds of Groups II and III.
Figure 28:
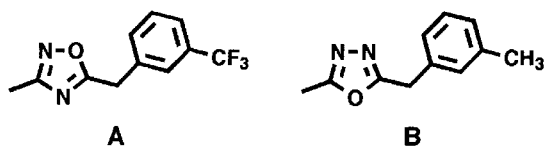
Figure 29:
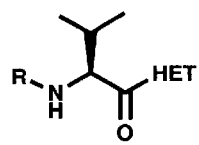
FIG. 29 shows the activity of certain compounds of Groups II, III and IV.
Figure 29:
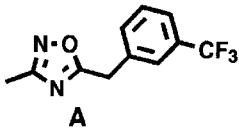
Figure 29:
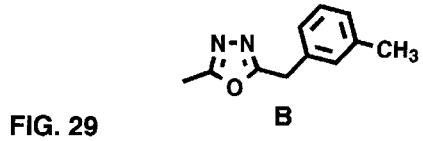
Figure 30:
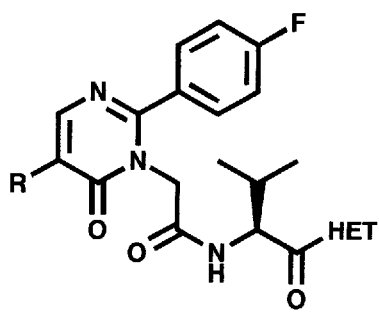
FIG. 30 shows the activity of certain compounds of Group V.
Figure 30:
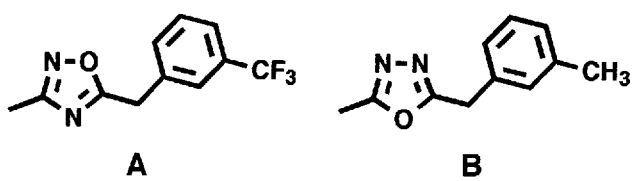
Figure 31:
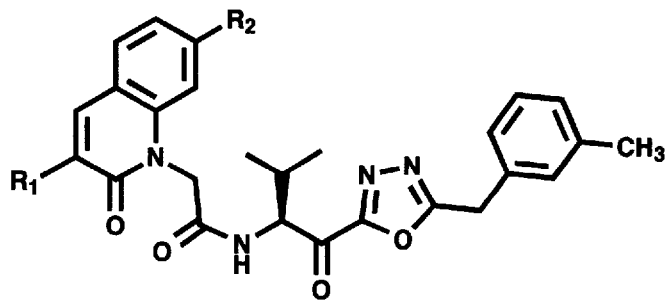
FIG. 31 shows the activity of certain compounds of Group V.
Figure 31:
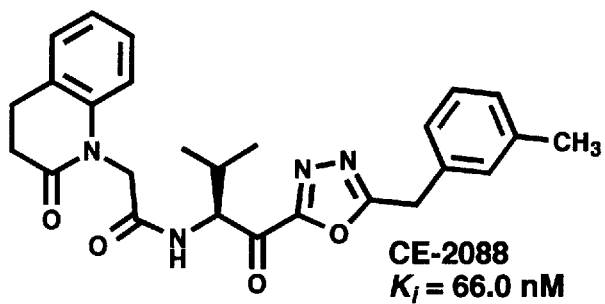
Figure 32:
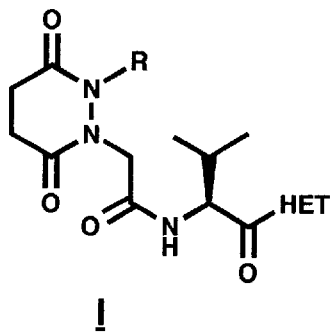
FIG. 32 shows the activity of certain compounds of Group V.
Figure 32:
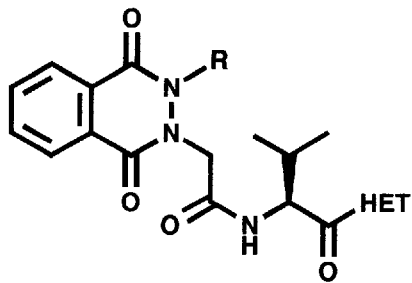
Figure 32:
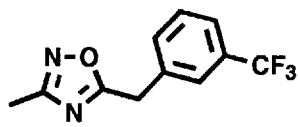
Figure 32:
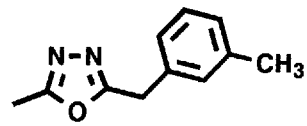
Figure 33:
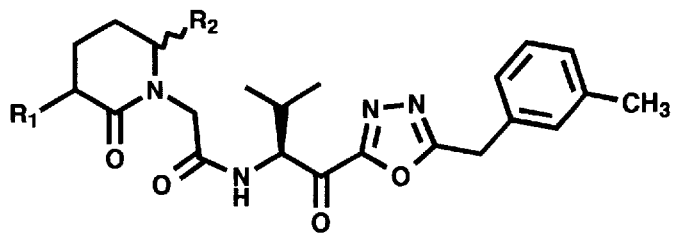
FIG. 33 shows the activity of certain compounds of Group V.
Figure 34:
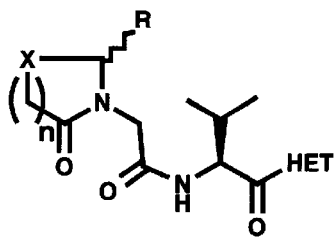
FIG. 34 shows the activity of certain compounds of Group V.
Figure 35:
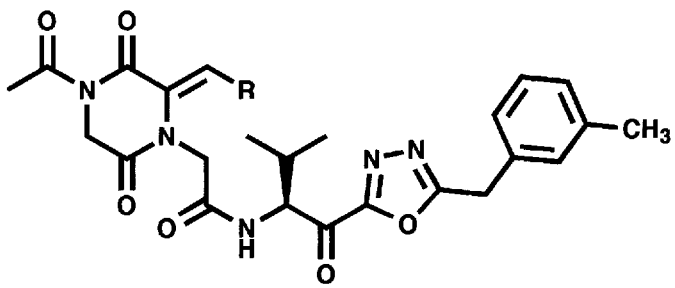
FIG. 35 shows the activity of certain compounds of Group V.
Figure 36:
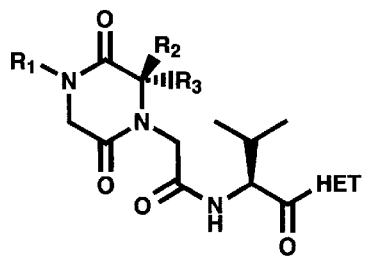
FIG. 36 shows the activity of certain compounds of Group V.
Figure 36:
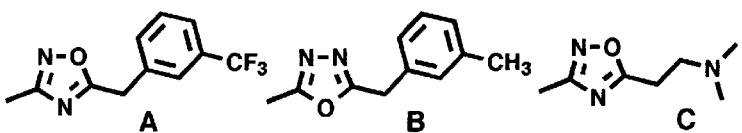
Figure 37:
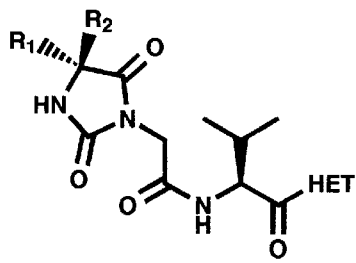
FIG. 37 shows the activity of certain compounds of Group V.
Figure 37:
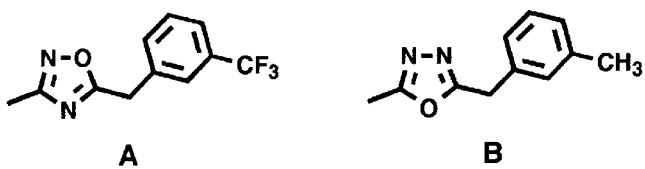
Figure 38:
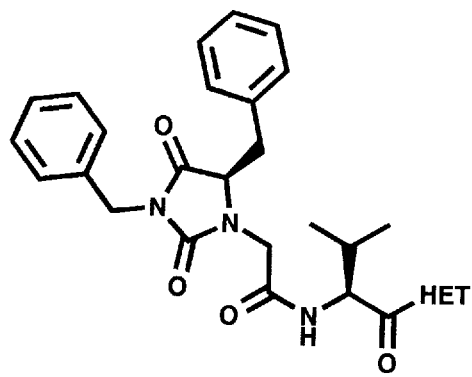
FIG. 38 shows the activity of certain compounds of Group V.

The compounds of the present invention, salts thereof, and their intermediates can be prepared or manufactured as described herein or by various process known to be present in the chemical art (see also, WO 96/16080). For example, compounds of Group I may be synthesized according to FIGS. 1–2 (1,3,4 oxadiazoles) and FIGS. 3–4 (1,2,4 oxadiazoles). FIGS. 5–7 describe the synthesis of compounds of Group II. FIGS. 8–9 describe the synthesis of compounds of Group III; FIG. 10 describes synthesis of Group IV compounds. The several classes of Group V compounds are described in FIGS. 11–22.

The activity of the compounds is presented in FIGS. 23–38 as $K_i$ values (nm). $K_i$ values were determined essentially as described in WO 96/16080.

Although the compounds described herein and/or their its salts may be administered as the pure chemicals, it is preferable to present the active ingredient as a pharmaceutical composition. The invention thus further provides the use of a pharmaceutical composition comprising one or more compounds and/or a pharmaceutically acceptable salt thereof, together with one or more pharmaceutically acceptable carriers therefor and, optionally, other therapeutic and/or prophylactic ingredients. The carrier(s) must be 'acceptable' in the sense of being compatible with the other ingredients of the composition and not deleterious to the recipient thereof.

Pharmaceutical compositions include those suitable for oral or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservative.

The compounds may also be formulated for parenteral administration (e.g., by injection, for example, bolus injection or continuous infusion) and may be presented in unit dose form in ampules, pre-filled syringes, small bolus infusion containers or in multi-does containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. Nos. 4,931,279, 4,668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4383,529, or 4,051,842.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The following examples are given to illustrate the invention and are not intended to be inclusive in any manner:

EXAMPLES

Example 1

(CE-2072)

(Benzyloxycarbonyl)-L-valyl-N-[1-(2-[5-(3-methylbenzyl)-1,3,4-oxadiazolyl]carbonyl)-2-(S)-methylpropyl]-L-prolinamide To a mixture containing 0.79 g (5.94 mmol) of N-chlorosuccinimide in 40 mL of anhydrous toluene at 0° C. under a nitrogen atmosphere was added 0.65 mL (8.85 nmol) of dimethyl sulfide. The reaction was cooled to −25° C. using a carbon tetrachloride/dry ice bath, followed by the dropwise addition of a solution containing (benzyloxycarbonyl)-L-valyl-N-[1-(2-[5-(3-methylbenzyl)-1,3,4 oxadiazolyl]hydroxymethyl)-2-(S)-methylpropyl]-L-prolinamide (0.90 g, 1.49 mmol) in 17 mL of anhydrous toluene. The reaction was allowed to stir for 2 hours at −25° C. followed by the addition of 1.0 mL (7.17 mmol) of triethylamine. The cold bath was removed and the mixture allowed to warm to room temperature and maintained for 20 minutes. The reaction mixture was diluted with ethyl acetate and washed with water. The organic phase was dried over magnesium sulfate, filtered and the solvent removed under reduced pressure. The residue was purified by column chromatography on silica gel with 70% ethyl acetate/hexane to give 0.90 g of material which was further purified via preparative HPLC to afford 665 mg (73.9%) of the title compound as a white solid. FAB MS [M+H] m/z; Calcd: 604, Found 604.

The intermediate (benzyloxycarbonyl)-L-valyl-N-[1-(2-[5-(3-methylbenzyl)-1,3,4-oxadiazolyl]hydroxymethyl)-2-(S)-methylpropyl]-L-prolinamide was prepared as follows:

a. 3-(S)-Amino-2-(R,S)-hydroxy-4-methyl pentanoic acid

To a solution containing 3-(S)-[(benzyloxycarbonyl) amino]-2-acetoxy-4-methylpentanenitrile (see example 1 of WO 96/16080) (15.2 g, 50.0 mmol) in 183 mL of dioxane was added 183 mL of concentrated hydrochloric acid and 7.45 mL of anisole. The reaction mixture was heated to reflux overnight. The hydrolysis reaction was allowed to cool to room temperature and then concentrated in vacuo. The resulting aqueous solution was extracted with ether (2×). The aqueous phase was placed on a Dowex 50X8-100 column (H+ form, preeluted with deionized water to pH=7). The column was eluted with 2.0N ammonium hydroxide and the pure fractions concentrated to afford 5.53 g (75%) of 3-(S)-amino-2-(R,S)-hydroxy-4-methylpentanoic acid as a pale yellow solid. FAB MS [M+H] m/z; Calcd: 148, Found: 148.

b. 3-(S)-[(Benzyloxycarbonyl)amino]-2-(R,S)-hydroxy-4-methylpentanoic acid

To a solution under an atmosphere of nitrogen containing 1.0 g (6.8 mmol) of 3-(S)-amino-2-(R,S)-hydroxy-4-methylpentanoic acid in 9.5 mL of 1N NaOH and 10 mL of dioxane was added 1.43 g (8.4 mmol) of benzyl chloroformate. The pH was maintained above pH 8 with 1N NaOH as needed. The reaction mixture was allowed to stir at room temperature overnight. The reaction was diluted with water and washed with ether. The aqueous layer was acidified with 1N HCl to pH=2 and extracted with ether (2×). The combined organic layers were dried over magnesium sulfate, filtered and evaporated in vacuo to afford 1.75 g (92%) of 3-(S)-[(benzyloxycarbonyl)amino]-2-(R,S)-hydroxy-4-methylpentanoic acid as a light yellow viscous oil. FAB MS [M+H] m/z; Calcd: 282, Found: 282.

c. 3-(S)-[(Benzyloxylcarbonyl)amino-2-(R,S)-acetoxy-4-methyl pentanoic acid

To a solution of 3-(S)-[(benzyloxycarbonyl)amino]-2-(R, S)-hydroxy-4-methylpentanoic acid (1.70 g, 6.04 mmol) and pyridine (4.9 mL) was added acetic anhydride (5.7 mL, 6.17 g, 60.4 mmol) dropwise at room temperature. The reaction was allowed to stir overnight and was diluted with ethyl acetate and washed with water (2×). The organic layer was dried over magnesium sulfate, filtered and evaporated in vacuo to give a thick oil. The residue was purified by column chromatography on silica gel with 15% methanol/dichloromethane to afford 1.56 g (80%) of 3-(S)-[

(benzyloxycarbonyl)amino]-2-(R,S)-acetoxy-4-methyl pentanoic acid as a light yellow viscous oil. FAB MS [M+H] m/z; Calcd: 324, Found: 324.

d. 1-[(3-Methylphenylacetyl)-2-(2-(R,S)-acetoxy)-3-(S)-[(benzyloxycarbonyl)amino]-4-methylpentanoyl]hydrazine To a solution containing 3-(S)-[(benzyloxycarbonyl)amino]-2-(R,S)-acetoxy-4-methylpentanoic acid (2.3 g, 7.11 mmol) in 40 mL of DMF under a nitrogen atmosphere at 0° C. was added 1.31 g (9.69 mmol) of HOBT and 1.36 g (7.09 mmol) of EDCI. After stirring for 30 minutes, 1.20 g (7.31 mmol) of 3-methylphenyl acetic hydrazide (prepared analogously to the monoacid hydrazides cited by Rabins et. al. (*J. Org. Chem*, 1965, 30, 2486) and 1.0 mL (9.10 mmol) of NMM were added. The reaction was allowed to warm to room temperature and stir overnight. The reaction was diluted with ethyl acetate and washed with 5% potassium hydrogen sulfate, saturated sodium bicarbonate, brine and water. The organic phase was dried over magnesium sulfate, filtered and evaporated under reduced pressure. The residue was purified by column chromotography on silica gel with 10% methanol/ dichloromethane to afford 2.31 g (89.0%) of the title compound as a white solid. FAB MS [M+H] m/z; Calcd: 470, Found: 470.

e. 1-[2-(5-[3-Methylbenzyl]-1,3,4-oxadiazolyl]-1-acetoxy-2-(S)-[(benzyloxycarbonyl)amino]-methylbutane A solution containing 2.31 g (4.92 mmol) of 1-[(3-methylphenylacetyl)-2-(2-(R,S)-acetoxy)-3-(S)-[(benzyloxycarbonyl)amino]-4-methyl pentanoyl]hydrazine in 25 mL of pyridine and 1.88 g (9.86 mmol) of toluene sulfonyl chloride was heated at reflux under a nitrogen atmosphere for 72 hours. The solvent was removed under reduced pressure and the residue dissolved in ethyl acetate and washed with water. The organic phase was dried over magnesium sulfate, filtered and evaporated under reduced pressure. The residue was purified by column chromatography on silica gel with 5% ethyl acetate/hexane to afford 1.41 g (63.5%) of the title compound. FAB MS [M+H] m/z; Calcd: 452, Found: 452.

f. 1-[2-(5-[3-Methylbenzyl]-1,3,4-oxadiazolyl)]-2-(S)-[(benzyloxycarbonyl)amino]-3-methylbutan-1-ol A solution containing 1.80 g (3.99 mmol) of 1-[2-(5-[3-methylbenzyl]-1,3,4-oxadiazolyl)]-1-acetoxy-2-(S)-[(benzyloxycarbonyl)amino]-3-methylbutane and 0.72 g (5.21 mmol) of potassium carbonate in 30 mL of methanol and 8 mL of water was allowed to stir at room temperature for 30 minutes. The solvent was removed under reduced pressure and the residue dissolved in ethyl acetate and washed with water. The organic phase was dried over magnesium sulfate, filtered and evaporated under reduced pressure. The residue was purified by column chromatography on silica gel with 60% ethyl acetate/hexane to afford 1.46 (89.3%) of the title compound. FAB MS [M+H] m/z; Calcd: 410, Found: 410.

g. 1-[2-(5-[3-Methylbenzyl])-1,3,4-oxadiazolyl]-2-(S)-Amino-3-methylbutan-1-ol hydrochloride To a solution containing 1.31 g (3.20 mmol) of 1-[2-(5-[3-methylbenzyl])-1,3,4-oxadiazolyl]-2-(S)-[(benzyloxycarbonyl)amino]-3-methylbutan-1-ol in 25 mL of trifuoroacetic acid under a nitrogen atmosphere at 0° C. was added 0.43 mL (3.94 mmol) of thioanisole. The reaction was allowed to warm to room temperature overnight. The solvent was removed under reduced pressure and the residue dissolved in ether and cooled to –78° C. under a nitrogen atmosphere. To this solution was added 3 mL (3 mmol) of 1N hydrochloric acid in ether. The resulting white solid was allowed to settle and the ether decanted. Additional ether was added and decanted (3x). The solid was dried under vacuum to afford 0.92 g (92.2%) of the title compound. FAB MS [M+H) m/z; Calcd: 276, Found: 276.

h. (Benzyloxycarbonyl)-L-valyl-N-[1]-(1-(2-[5-(3-methylbenzyl)-1,3,4-oxadiazolyl]hydroxylmethyl)-2-(S)-methylpropyl]-L-prolinamide To a solution containing 1.30 g (3.38 mmol) of Cbz-Val-Pro-OH in 25 mL of anhydrous dichloromethane under a nitrogen atmosphere at 0° C. was added 0.90 g (3.54 mmol) of BOPCl and 0.60 g (3.44 mmol) of DIEA. After stirring for 30 minutes, 0.90 g (2.89 mmol) of 1-[2-(5-[3-methylbenzyl])-1,3,4-oxadiazolyl]-2-(S)-amino-3-methyl butan-1-ol hydrochloride in 15 mL of dichloromethane and 0.6 mL (3.94 mmol) of DIEA was added. The reaction was allowed to stir at 0° C. overnight. The reaction was diluted with dichloromethane and washed with a saturated sodium bicarbonate solution. The organic phase was dried over magnesium sulfate, filtered and evaporated. The residue was purified by column chromatography on silica gel with 6% methanol/dichloromethane to afford 1.0 g (57.3%) of the title compound as a tan solid. FAB MS [M+H] m/z; Calcd: 606, Found: 606.

Example 2

(CE-2074)

(Benzyloxycarbonyl)-L-valyl-N-[1-(2-[5-(methyl)-1,3,4-oxadiazoly]carbony)-2-(S)-methylpropyl]-L-prolinamide Prepared similar to Example 1. FAB MS [M+H] m/z; Calcd: 514, Found: 514.

Example 3

(CE-2075)

(Benzyloxycarbonyl)-L-valyl-N-[1-(2-[5-(3-trifluoromethylbenzyl)-1,3,4-oxadiazolyl]carbonyl)-2-(S)-methylpropyl]-L-prolinamide Prepared similar to Example 1. FAB MS [M+H] m/z; Calcd: 658, Found: 658.

Example 4

(CE-2100)

(Benzyloxycarbonyl)-L-valyl-N-[1-(2-[5-(4-Dimethylamino benzyl)-1,3,4-oxadiazolyl]carbonyl)-2-(S)-methylpropyl]-L-prolinamide Prepared similar to Example 1. FAB MS [M+H] m/z; Calcd: 633, Found: 633.

Example 5

(CE-2124)

(Benzyloxycarbonyl)-L-valyl-N-[1-(2-[5-(1-napthylenyl)-1,3,4-oxadiazolyl]carbonyl)-2-(S)-methylpropyl]-L-prolinamide Prepared similar to Example 1. FAB MS [M+H] m/z; Calcd: 640, Found: 640.

Example 6

(Benzyloxycarbonyl)-L-valyl-N-[1-(3-[5-(3,4-methylenedioxybenzyl)-1,2,4-oxadiazolyl]carbonyl)-2-(S)-methylpropyl]-L-prolinamide Prepared similar to Example 1 of WO 96/16080. FAB MS [M+H] m/z; Calcd: 634, Found 634.

Example 7

(CE-2052)

(Benzyloxycarbonyl)-L-valyl-N-[1-(3-[5-(3,5-dimethylbenzyl)-1,2,4-oxadiazolyl]carbonyl)-2-(S)-methylpropyl]-L-prolinamide Prepared similar to Example 1 of WO 96/16080. FAB MS [M+H] m/z; Calcd: 618, Found 618.

Example 8

(CE-2053)

(Benzyloxycarbonyl)-L-valyl-N-[1-(3-[5-(3,5-dimethoxybenzyl)-1,2,4-oxadiazolyl]carbonyl)-2-(S)-methylpropyl]-L-prolinamide Prepared similar to Example 1 of WO 96/16080. FAB MS [M+H] m/z; Calcd: 650, Found 650.

Example 9

(CE-2054)

(Benzyloxycarbonyl)-L-valyl-N-[1-(3-[5-(3,5-ditrifluoromethylbenzyl)-1,2,4-oxadiazolyl]carbonyl)-2-(S)-methylpropyl]-L-prolinamide Prepared similar to Example 1 of WO 96/16080. FAB MS [M+H] m/z; Calcd: 726, Found 726.

Example 10

(CE-2055)

(Benzyloxycarbonyl)-L-valyl-N-[1-(3-[5-(3-methylbenzyl)-1,2,4-oxadiazolyl]carbonyl)-2-(S)-methylpropyl]-L-prolinamide Prepared similar to Example 1 of WO 96/16080. FAB MS [M+H] m/z; Calcd: 604, Found 604.

Example 11

(CE-2057)

(Benzyloxycarbonyl)-L-valyl-N-[1-(3-[5-(biphenylmethine)-1,2,4-oxadiazolyl]carbonyl)-2-(S)-methylpropyl]-L-prolinamide Prepared similar to Example 1 of WO 96/16080. FAB MS [M+H] m/z; Calcd: 666, Found 666.

Example 12

(CE-2058)

(Benzyloxycarbonyl)-L-valyl-N-[1-(3-[5-(4-phenylbenzyl)-1,2,4-oxadiazolyl]carbonyl)-2-(S)-methylpropyl]-L-prolinamide Prepared similar to Example 1 of WO 96/16080. FAB MS [M+H] m/z; Calcd: 666, Found 666

Example 13

(CE-2062)

(Benzyloxycarbonyl)-L-valyl-N-[1-(3-[5-(3-phenylbenzyl)-1,2,4-oxadiazolyl]carbonyl)-2-(S)-methylpropyl]-L-prolinamide Prepared similar to Example 1 of WO 96/16080. FAB MS [M+H] m/z; Calcd: 666, Found 666.

Example 14

(CE-2066)

(Benzyloxycarbonyl)-L-valyl-N-[1-(3-[5-(3-phenoxybenzyl)-1,2,4-oxadiazolyl]carbonyl)-2-(S)-methylpropyl]-L-prolinamide Prepared similar to Example 1 of WO 96/16080. FAB MS [M+H] m/z; Calcd: 682, Found 682.

Example 15

(CE-2069)

(Benzyloxycarbonyl)-L-valyl-N-[1-(3-[5-(cyclohexylmethylene)-1,2,4-oxadiazolyl]carbonyl)-2-(S)-methylpropyl]-L-prolinamide Prepared similar to Example 1 of WO 96/16080. FAB MS [M+H] m/z; Calcd: 596, Found 596.

Example 16

(CE-2073)

(Benzyloxycarbonyl)-L-valyl-N-[1-(3-[5-(3-trifluoromethyldimethylmethylene)-1,2,4-oxadiazolyl]carbonyl)-2-(S)-methylpropyl]-L-prolinamide Prepared similar to Example 1 of WO 96/16080. FAB MS [M+H] m/z; Calcd: 686, Found 686.

Example 17

(CE-2077)

(Benzyloxycarbonyl)-L-valyl-N-[1-(3-[5-(1-napthylmethylene)-1,2,4-oxadiazolyl]carbonyl)-2-(S)-methylpropyl]-L-prolinamide Prepared similar to Example 1 of WO 96/16080. FAB MS [M+H] m/z; Calcd: 640, Found 640.

Example 18

(CE-2078)

(Benzyloxycarbonyl)-L-valyl-N-[1-(3-[5-(3-pyridylmethyl)-1,2,4-oxadiazolyl]carbonyl)-2-(S)-methylpropyl]-L-prolinamide Prepared similar to Example 1 of WO 96/16080. FAB MS [M+H] m/z; Calcd: 591, Found 591.

Example 19

(CE-2096)

(Benzyloxycarbonyl)-L-valyl-N-[1-(3-[5-(3,5-diphenylbenzyl)-1,2,4-oxadiazolyl]carbonyl)-2-(S)-methylpropyl]-L-prolinamide Prepared similar to Example 1 of WO 96/16080. FAB MS [M+H] m/z; Calcd: 742, Found 742.

Example 20

(CE-2115)

(Benzyloxycarbonyl)-L-valyl-N-[1-(3-[5-(4-dimethylaminobenzyl)-1,2,4-oxadiazolyl]carbonyl)-2-(S)-methylpropyl]-L-prolinamide Prepared similar to Example 1 of WO 96/16080. FAB MS [M+H] m/z; Calcd: 633, Found 633.

Example 21

(CE-2089)

2-[5-[(Benzyloxycarbonyl)amino]-6-oxo-2-(4-fluorophenyl)-1,6-dihydro-1-pyrimidinyl]-N-[1-(3-[5-(3-trifluoromethylbenzyl)-1,2,4-oxadiazolyl]carbonyl)-(S)-2-methylpropyl]acetamide To a mixture containing 1.15 g (8.60 mmol) of N-chlorosuccinimide in 43 mL of anhydrous toluene at 0° C. under a nitrogen atmosphere was added 0.95 mL (12.9 mmol) of dimethyl sulfide. The reaction was cooled to −25° C. using a carbon tetrachloride/dry ice bath, followed by the dropwise addition of a solution containing 2-[5-[(benzyloxycarbonyl)amino]-6-oxo-2-(4-fluorophenyl)-1,6-dihydro-1-pyrimidinyl]-N-[1-(3-[5-(3-trifluoromethylbenzyl)-1,2,4-oxadiazolyl]hydroxymethyl)-(S)-2-methylpropyl]acetamide (1.52 g, 2.15 mmol) in 15 mL of anhydrous toluene. The reaction was allowed to stir for 2 hours at −25° C. followed by the addition of 1.2 mL (8.60 mmol) of triethylamine. The cold bath was removed and the mixture allowed to warm to room temperature over 20 minutes. The reaction mixture was diluted with ethyl acetate and washed with water. The organic phase was dried over magnesium sulfate, filtered and evaporated under reduced pressure. The residue was purified by column chromatography on silica gel using a gradient elution of 2 to 10% methanol/dichloromethane to afford 1.19 g of material which was further purified via preparative HPLC to afford 629 mg (41%) of the title compound as a white solid. FAB MS [M+H] m/z; Calcd: 707, Found: 707.

The intermediate 2-[5-[(benzyloxycarbonyl)amino]-6-oxo-2-(4-fluorophenyl)-1,6-dihydro-1-pyrimidinyl]-N-[1-(3-[5-(3-trifluoromethylbenzyl)-1,2,4oxadiazolyl]hydroxymethyl)-(S)-2-methylpropyl]acetamide was prepared as follows: to a solution containing 1.35 g (3.7 mmol) of 1-[3-[5-(3-methylbenzyl)-1,2,4-oxadiazolyl]-2-(S)-amino-3-methylbutan-1-ol hydrochloride and [5-[(benzyloxycarbonyl)amino]-6-oxo-2-(4-fluorophenyl)-1,6-dihydro-1-pyrimidinyl]acetic acid (J. Med. Chem. 1995, 38, 98–108) in 10 mL of anhydrous DMF was added 1.0 mL (7.44 mmol) of TEA and 0.76 g (4.94 mmol) of HOBT. The mixture was cooled to 0° C. and 0.95 g (4.94 mmol) of EDC was added and the reaction mixture was allowed to stir overnight. An additional 1.0 mL (7.44 mmol) of TEA was added and the reaction again allowed to stir overnight. The reaction was diluted with dichlormethane and washed with a saturated ammonium chloride solution (2x) and water. The organic phase was dried over magnesium sulfate, filtered and evaporated under reduced pressure. The residue was purified by column chromatography on silica gel with 2% methanol/dichloromethane to afford 1.52 g (87%) of the title compound. FAB MS [M+H] m/z; Calcd: 709, Found: 709.

Example 22

(CE-2090)

2-[5-Amino-6-oxo-2-(4-fluorophenyl)-1,6-dihydro-1-pyrimidinyl]-N-[1-(3-[5-(3-trifluoromethylbenzyl)-1,2,4-oxadiazolyl]carbonyl)-2-(S)-methylpropyl]acetamide To a mixture containing 0.41 g (0.58 mmol) of 2-[5-[(benzyloxycarbonyl)amino]-6-oxo-2-(4-fluorophenyl)-1,6-dihydro-1-pyrimidinyl]-N-[1-(3-[5-(3-trifluormethylbenzyl)-1,2,4-oxadiazolyl]carbonyl)-(S)-2-methylpropyl]acetamide in 4 mL of trifluoroacetic acid at room temperature under a nitrogen atmosphere was added 87 mg (0.70 mmol) of thioanisole. The reaction mixture was allowed to stir for 3 days and concentrated in vacuo. The residue was purified via preparative HPLC to afford 269 mg (47%) of the title compound as a white solid. FAB MS [M+H] m/z; Calcd: 573, Found: 573.

Example 23

(CE-2095)

2-[5-[(Benzyloxycarbonyl)amino]-6-oxo-2-(4-fluorophenyl)-1,6-dihydro-1-pyrimidinyl]-N-[1-(2-[5-(3-methylbenzyl)-1,3,4-oxadiazolyl]carbonyl)-(S)-2-methylpropyl]acetamide To a mixture containing 0.83 g (6.23 mmol) of N-chlorosuccinimide in 32 mL of anhydrous toluene at 0° C. under a nitrogen atmosphere was added 0.7 mL (9.35 mmol) of dimethyl sulfide. The reaction was cooled to −25° C. using a carbon tetrachloride/dry ice bath, followed by the dropwise addition of a solution containing 2-[5-[(benzyloxycarbonyl)amino]-6-oxo-2-(4-fluorophenyl)-1,6-dihydro-1-pyrimidinyl]-N-[1-(2-[5-(3-methylbenzyl)-1,3,4-oxadiazolyl]hydroxymethyl)-(S)-2-methylpropyl]acetamide (1.02 g, 1.56 mmol) in 12 mL of anhydrous toluene. The reaction was allowed to stir for 2 hours at −25° C. followed by the addition of 0.9 mL (6.23 mmol) of triethylamine. The cold bath was removed and the mixture allowed to warm to room temperature over 20 minutes. The reaction mixture was diluted with ethyl acetate and washed with water. The organic phase was dried over magnesium sulfate, filtered and evaporated. The residue was purified by column chromatography on silica gel using 1% methanol/dichloromethane to afford 1.37 g of material which was further purified via preparative HPLC to give 368 mg (36%) of the title compound as a white solid. FAB MS [M+H] m/z; Calcd: 653, Found: 653.

The intermediate 2-[5-[(benzyloxycarbonyl)amino]-6-oxo-2-(4-fluorophenyl)-1,6-dihydro-1-pyrimidinyl]-N-[1-(2-[5-(3-methylbenzyl)-1,3,4-oxadiazolyl]hydroxymethyl)-(S)-2-methylpropyl]acetamide was prepared as follows: to a solution containing 1.35 g (3.7 mmol) of 1-[2-[5-(3-methylbenzyl)-1,3,4-oxadiazolyl]-2-(S)-amino-3-methyl butane hydrochloride and [5-[(benzyloxycarbonyl)amino]-6-oxo-2-(4-fluorophenyl)-1,6-dihydro-1-pyrimidinyl]acetic acid (J. Med. Chem. 1995, 38, 98–108) in 10 mL of anhydrous DMF was added 0.73 mL (6.6 mmol) of NMM and 0.46 g (3.0 mmol) of HOBT. The mixture was cooled to 0° C. and 0.50 g (2.6 mmol) of EDCI was added and the reaction mixture was allowed to stir for 2 days. The reaction was diluted with dichloromethane and washed with a saturated ammonium chloride solution (2x) and water. The organic phase was dried over magnesium sulfate, filtered and evaporated under reduced pressure. The residue was purified by column chromatography on silica gel using a gradient elution of 2 to 5% methanol/dichloromethane to afford 1.02 g (77%) of the title compound. FAB MS [M+H] m/z; Calcd: 655, Found: 655.

Example 24

(CE-2101)

2-[5-Amino-6-oxo-2-(4-fluorophenyl)-1,6-dihydro-1-pyrimidinyl]-N-[1-(2-[5-(3-methylbenzyl)-1,3,4-oxadiazolyl]carbonyl)-2-(S)-methylpropyl]acetamide To a mixture containing 0.219 g (0.335 mmol) of 2-[5-[(benzyloxycarbonyl)amino]-6-oxo-2-(4-fluorophenyl)-1,6- dihydro-1-pyrimidinyl]-N-[1-(2-[5-(3-methylbenzyl)-1,3,4-oxadiazolyl]carbonyl)-(S)-2-methylpropyl]acetamide in 3 mL of trifluoroacetic acid at room temperature under a nitrogen atmosphere was added 0.05 mL (0.402 mmol) of thioanisole. The reaction mixture was allowed to stir for 3 days and concentrated in vacuo. The residue was purified via preparative HPLC to afford 187 mg (88%) of the title compound as a white solid. FAB MS [M+H] m/z; Calcd: 519, Found: 519.

Example 25

(CE-2164)

(Pyrrole-2-carbonyl)-N-(benzyl)glycyl-N-[1-(2-[5-(3-methylbenzyl)-1,3,4-oxadiazolyl]carbonyl)-2-(S)-methylpropyl]amide To a mixture containing 1.97 g (14.7 mmol) of N-chlorosuccinimide on 60 mL of anhydrous toluene at 0° C. under a nitrogen atmosphere was added 1.54 mL (21.0 mmol) of dimethyl sulfide. The mixture was allowed to stir for 1 hr. The reaction was cooled to −25° C. using a carbon tetrachloride/dry ice bath, followed by the dropwise addition of a solution containing (0.90 g, 1.49 mmol) of (pyrrole-2-carbonyl)-N-(benzyl)glycyl-N-[1-(2-[5-(3-methylbenzyl)-1,3,4-oxadiazolyl]hydroxymethyl)]-2-(S)-methylpropyl]amide in 30 mL of anhydrous toluene. The reaction was allowed to stir for 1 hour at −25° C. followed by the addition of 2.16 mL (15.5 mmL) of triethylamine. The cold bath was removed and the mixture allowed to warm to room temperature over 20 minutes. The reaction mixture was diluted with ethyl acetate and washed with water. The organic phase was dried over magnesium sulfate, filtered and evaporated under reduced pressure. The residue was purified by column chromatography on silica gel with ethyl acetate/hexane (4:1). The material was further purified via preparative HPLC to afford 1.20 g (63.4%) of the title compound as a white solid. FAB MS [M+H] m/z; Calcd: 514, Found: 514.

The intermediate (pyrrole-2-carbonyl)-N-(benzyl)glycyl-N-[1-(2-[5-(3-methylbenzyl)-1,3,4-oxadiazolyl]hydroxymethyl)]-2-(S)-methylpropyl]amide was prepared by the following method:

a. (Pyrrole-2-carbonyl)-N-(benzyl)glycine-t-butyl ester

To a suspension containing 3.00 g (27.0 mmol) of pyrrole-2-carboxylic acid in 75 mL of anhydrous dichloromethane under a nitrogen atmosphere at 0° C. was added 6.96 g (27.0 mmol of BOPCl and 14.1 mL (81.0 mmol) of DIEA. After stirring for 30 minutes, 5.97 g (27.0 mmol) of N-(benzyl) glycine-t-butyl ester was added and the reaction allowed to warm to room temperature overnight. The reaction was diluted with ethyl acetate and washed with a 5% potassium hydrogensulfate, saturated sodium bicarbonate solution and brine. The organic phase was dried over magnesium sulfate, filtered and evaporated under reduced pressure. The residue was purified by column chromatography on silica gel using a gradient of 100% hexane to 60% hexane/ethyl acetate to afford 2.92 g (34.4%) of the title compound is a white solid. FAB MS [M+H] m/z Calcd: 315, Found: 315.

b. (Pyrrole-2-carbonyl)-N-(benzyl)glycine

To a solution containing 2.85 (9.01 mmol) of (Pyrrole-2-carbonyl)-N-(benzyl)glycine-t-butyl ester in 50 mL of anhydrous dichloromethane cooled to 0° C. was added 25 mL of TFA dropwise. After 90 minutes an additional 25 mL of TFA was added and allowed to stir for 30 minutes. The mixture was evaporated in vacuo to afford 2.19 g of (Pyrole-2-carbonyl)-N-(benzyl)glycine as a tan solid. FAB MS [M+H] m/z; Calcd. 259, Found 259.

c. (Pyrrole-2-carbonyl)-N-(benzyl)glycyl-N-[1-(2-[5-(3-methylbenzyl)-1,3,4-oxadiazolyl]hydroxymethyl)-(S)-2-methylpropyl]amide To a solution containing 1.90 g (7.35 mmol) of (Pyrrole-2-carbonyl)-N-(benzyl)glycine in 75 mL of anhydrous DMF was added 2.4 mL (22.1 mmol) of NMM and 1.29 g (9.56 mmol) of HOBT. The mixture was cooled to 0° C. and 1.69 g (8.82 mmol) of EDCI was added and the reaction mixture was allowed to stir. After 30 minutes 2.17 g (6.99 mmol) of 1-[2-(5-[3-methylbenzyl])-1,3,4-oxadiazolyl]-2-(S)-amino-3-methyl butan-1-ol hydrochloride in 25 mL of anhydrous DMF was added and the mixture was allowed to warm to room temperature overnight. The reaction was diluted with ethyl acetate and washed with 5% potassium hydrogen sulfate and water. The organic phase was dried over magnesium sulfate, filtered and evaporated under reduced pressure. The residue was purified by column chromatography on silica gel using a gradient elution of 20 to 80% ethyl acetate/hexane to afford 2.02 g (56%) of the title compound. FAB MS [M+H] m/z Calcd: 516, Found: 516.

Example 26

(CE-2097)

(Pyrrole-2-carbonyl)-N-(benzyl)glycyl-N-[1-(3-[5-(3-trifluoromethylbenzyl)]-1,2,4-oxadiazolyl)-(S)-methylpropyl]amide was prepared in a similar manner to Example 25. FAB MS [M+H] m/z; Calcd: 568, Found: 568.

Example 27

(CE-2130)

(2S,5S)-5-Amino-1,2,4,5,6,7-hexahydroazepino-[3,2,1]-indole-4-one-carbonyl-N-[1-(2-[5-(3-methylbenzyl)-1,3,4-oxadiazolyl]carbonyl)-(R,S)-2-methylpropyl]amide To a solution containing 0.93 g (1.28 mmol) of (2S, 5S)-Fmoc-5-amino-1,2,4,5,6,7-hexahydroazepino [3,2,1] indole-4-one-carbonyl-N-[1-(2-[5-(3-methylbenzyl)-1,3,4-oxadiazolyl]carbonyl)-(S)-2-methylpropyl]amide in 4.5 mL of anhydrous DMF under an atmosphere of nitrogen was added 0.45 mL of diethylamine. After stirring at room temperature for 15 min the mixture was concentrated under high vacuum. The residue was purified via preparative HPLC to afford 0.57 g (72%) of the title compound as a white solid. FAB MS [M+H] m/z; Calcd: 502, Found 502.

The intermediate (2S, 5S)-Fmoc-5-amino-1,2,4,5,6,7-hexahydroazepino-[3,2,1]-indole-4-one-carbonyl-N-[1-(2-[5-(3-methylbenzyl)-1,3,4-oxadiazolyl]carbonyl)-(S)-2-methylpropyl]amide was prepared as follows:

a. (2S, 5S)-Fmoc-5-amino-1,2,4,5,6,7-hexahydroazepino-[3,2,1]-indole-4-one-carbonyl-N-[1-(2-[5-(3-methylbenzyl)-1,3,4-oxadiazolyl]hydroxymethyl)-(S)-2-methylpropyl]amide To a solution containing 1.25 g (2.67 mmol) of (2S, 5S)-Fmoc-5-amino -1,2,4,5,6,7-hexahydroazepino [3,2,1] indole-4-one-carboxylic acid in 200 mL of anhydrous dichloromethane and 1 mL of anhydrous DMF under a nitrogen atmosphere at 0° C. was added 0.71 g (2.80 mmol) of BOPCl and 0.6 mL (3.45 mmol) of DIEA. After stirring for 1 hr 1.14 g (3.66 mmol) of 1-[2-(5-[3-methylbenzyl])-1,3,4-oxadiazolyl]-2-(S)-amino-3-methylbutan-1-ol hydrochloride in 10 mL of anhydrous dichloromethane was added and the reaction mixture allowed to stir at 4° C. overnight. The reaction was diluted with dichloromethane and washed with water. The organic phase was dried over magnesium sulfate, filtered and evaporated under reduced pressure. The residue was purified by column chromatography on silica gel using 3% methanol/dichloromethane to afford 1.30 g (67%) of the title compound as tan solid.

b. (2S, 5S)-Fmoc-5-amino-1,2,4,5,6,7-hexahydroazepino-[3,2,1]-indole-4-one-carbonyl-N-[1-(2-[5-(3-methylbenzyl)-1,3,4-oxadiazole]carbonyl)]-(S)-2-methylpropyl]amide To a mixture containing 0.95 g (7.16 mmol) of N-chlorosuccinimide in 150 mL of anhydrous toluene at 0° C. under a nitrogen atmosphere was added 0.79 mL (10.7 mmol) of dimethyl sulfide. The mixture was allowed to stir for 30 minutes. The reaction was cooled to −25 ° C. using a carbon tetrachloride/dry ice bath, followed by the dropwise addition of a solution containing 1.30 g (1.79 mmol) of (2S, 5S)-Fmoc-5-amino-1,2,4,5,6,7-hexahydroazepino-[3,2,1]-indole-4-one-carbonyl-N-[1-(2-[5-(3-methylbenzyl)-1,3,4-oxadiazolyl]hydroxymethyl)]-(S)-2-methylpropyl]amide in 10 mL of anhydrous toluene. The reaction was allowed to stir for 2 hours at −25 ° C. followed by the addition of 1.17 mL (8.4 mmol) of triethylamine. The cold bath was removed and the mixture was allowed to warm to room temperature over 30 minutes. The reaction mixture was diluted with ethyl acetate and washed with water. The organic phase was dried over magnesium sulfate. The residue was filtered, concentrated under reduced pressure and purified by column chromatography on silica gel with 10% ethyl acetate/hexane to give 0.93 g (72%) as a tan foam.

Example 28

(CE-2126)

BTD-[1-(2-[5-(3-methylbenzyl)-1,3,4-oxadiazolyl]carbonyl-2-(S)-methylpropyl]amide To a solution containing 0.41 g (0.59 mmol) of FMOC-BTD-[1-(2-[5-(3-methylbenzyl)-1,3,4-oxadiazole]carbonyl)-2-(S)-methylpropyl]amide in 4.5 mL of anhydrous DMF under an atmosphere of nitrogen was added 0.5 mL of diethylamine. After stirring at room temperature for 30 min the mixture concentrated under high vacuum. The residue was purified via preparative HPLC to afford 0.23 g (66%) of the title compound as a white solid. FAB MS [M+H] m/z; Calcd: 472, Found 472.

The intermediate Fmoc-BTD-[1-(2-[5-(3-methylbenzyl)-1,3,4-oxadiazolyl]carbonyl)-2-(S)-methylpropyl]amide was prepared as follows:

a. (2S, 5S)-Fmoc-BTD-[1-(2-[5-(3-methylbenzyl)-1,3,4-oxadiazolyl]hydroxymethyl)-2-(S)-methylpropyl]amide To a solution containing 1.25 g (2.85 mmol) of FMOC-BTD in 80 mL of anhydrous dichloromethane and 2.5 mL of anhydrous DMF under a nitrogen atmosphere at 0° C. was added 0.76 g (2.99 mmol) of BOPCl and 0.6 mL (3.45 mmol) of DIEA. After stirring for 30 minutes and 1.14 g (3.66 mmol) of 1-[2-(5-[3-methylbenzyl])-1,3,4-oxadiazolyl]-2-(S)-amino-3-methylbutan-1-ol hydrochloride and 0.6 mL of DIEA in 10 mL of anhydrous dichloromethane was added and the reaction mixture allowed to stir at 0° C. overnight. The reaction was diluted with dichloromethane and washed with water. The organic phase was dried over magnesium sulfate, filtered and evaporated under reduced pressure. The residue was purified by column chromatography on silica gel using 3% methanol/dichloromethane to afford 1.13 g (55%) of the title compound as a tan foam.

b. Fmoc-BTD-[1-(2-[5-(3-methylbenzyl)-1,3,4-oxadiazolyl]carbonyl)]-2-(S)-methylpropyl]amide To a mixture containing 0.81 g (6.09 mmol) of N-chlorosuccinimide in 110 mL of 1:1 anhydrous dichloromethane/toluene at 0° C. under a nitrogen atmosphere was added 0.67 mL (9.1 mmol) of dimethyl sulfide. The mixture was allowed to stir for 30 minutes. The reaction was cooled to −25 ° C. using a carbon tetrachloride/dry ice bath, followed by the dropwise addition of a solution containing 1.06 g (1.52 mmol) of Fmoc-BTD-[1-(2-[5-(3-methylbenzyl)-1,3,4-oxadiazolyl]hydroxymethyl)-2-(S)-methylpropyl]amide in 10 mL of anhydrous toluene. The reaction was allowed to stir for 2 hours at −25 ° C. followed by the addition of 1.0 mL (7.6 mmol) of triethylamine. The cold bath was removed and the mixture was allowed to warm to room temperature over 40 minutes. The reaction mixture was diluted with ethyl acetate and washed with water. The organic phase was dried over magnesium sulfate. The resulting mixture was filtered, concentrated under reduced pressure and purified by column chromatography on silica gel with 70% ethyl acetate/hexane to give 0.53 g of the product as a yellow oil. The material was further purified by preparative HPLC to afford 0.41 g (38.8%) of the title compound as a white solid.

Example 29

(CE-2134)

(R,S)-3-Amino-2-oxo-5-phenyl-1,4,-benzodiazepine-N-[1-(2-[5-(3-methylbenzyl)-1,3,4-oxadiazolyl]carbonyl)-2-(S)-methylpropyl]acetamide To a solution containing 0.93 g (1.19 mmol) of (R,S)-FMOC-3-amino-2-oxo-5-phenyl-1,4,-benzodiazepine-N-[1-(2-[5-(3-methylbenzyl)-1,3,4-oxadiazolyl]carbonyl)-2-(S)-methylpropyl]acetamide in 5.0 mL of anhydrous DMF under an atmosphere of nitrogen was added 0.45 mL of diethylamine. After stirring at room temperature for 2.5 hr the mixture was concentrated under high vacuum. The residue was purified via preparative HPLC to afford 0.030 g (4.5%) of the title compound as a white solid. FAB MS [M+H] m/z; Calcd: 565, Found 565.

The intermediate (R,S)-FMOC-3-amino-2-oxo-5-phenyl-1,4,-benzodiazepine-N-[1-(2-[5-(3-methylbenzyl)-1,3,4-oxadiazolyl]carbonyl)-2-(S)-methylpropyl]acetamide was prepared as follows:

a. (R,S)-FMOC-3-amino-2-oxo-5-phenyl-1,4,-benzodiazepine-N-[1-(2-[5-(3-methylbenzyl)-1,3,4-oxadiazolyl]hydroxymethyl)-2-(S)-methylpropyl]acetamide To a solution containing 0.75 g (1.41 mmol) of (R,S)-FMOC-3-amino-N-1-carboxymethyl-2-oxo-5-phenyl-1,4,-benzodiazepine in 30 mL of anhydrous dichloromethane under a nitrogen atmosphere at 0° C. was added 0.36 g (1.41 mmol) of BOPCl and 0.25 mL (1.41 mmol) of DIEA. After stirring for 1 hr 0.48 g (1.55 mmol) of 1-[2-[5-(3-methylbenzyl)-1,3,4-oxadiazolyl]-2-(S)-amino-3-methyl butan-1-ol hydrochloride and 0.49 mL (2.82 mmol) of DIEA in 10 mL of anhydrous dichloromethane was added and the reaction mixture allowed to stir at 4° C. overnight. The reaction was diluted with ethyl acetate and washed with water. The organic phase was dried over magnesium sulfate, filtered and evaporated under reduced pressure. The residue was purified by column chromatography on silica gel using a gradient of 2 to 6% methanol/dichloromethane to afford 1.00 g (89%) of the title compound as a yellow solid.

b. (R,S)-FMOC-3-amino-2-oxo-5-phenyl-1,4,-benzodiazepine-N-[1-(2-[5-(3-methylbenzyl)-1,3,4-oxadiazolyl]carbonyl)-2-(S)-methylpropyl]acetamide To a mixture containing 0.71 g (7.6 mmol) of N-chlorosuccinimide in 40 mL of anhydrous toluene at 0° C. under a nitrogen atmosphere was added 0.84 mL (11.4 mmol) of dimethyl sulfide. The reaction was cooled to −25° C. using a carbon tetrachloride/dry ice bath followed by the dropwise addition of a solution containing 1.50 g (1.90 mmol) of (R,S)-FMOC-3-amino-2-oxo-5-phenyl-1,4,-benzodiazepine-N-[1-(2-[5-(3-methylbenzyl)-1,3,4-oxadiazolyl]hydroxymethyl)-2-(S)-methylpropyl]acetamide in 10 mL of anhydrous toluene. The reaction was allowed to stir for 2 hours at −25 ° C. followed by the addition of 1.0 mL (7.6 mmol) of triethylamine. The cold bath was removed and the mixture was allowed to warm to room temperature over 1 hour. The reaction mixture was diluted with ethyl acetate and washed with water. The organic phase was dried over magnesium sulfate. The residue was filtered, concentrated under reduced pressure to afford 0.94 g (62%) of material which was used without further purification. FAB MS [M+H] m/z; Calcd: 787, Found: 787.

Example 30

(CE-2145)

(Benzyloxycarbonyl)-L-valyl-2-L-(2,3-dihydro-1H-indole)-N-[1-(2-[5-(3-methylbenzyl)-1,3,4-oxadiazolyl]carbonyl)-2-(S)-methylpropyl]amide To a mixture containing 0.48 g (3.67 mmol) of N-chlorosuccinimide in 30 mL of anhydrous toluene at 0° C. under a nitrogen atmosphere was added 0.40 mL (5.41 mmol) of dimethyl sulfide. After stirring for 1 hr the reaction mixture was cooled to −25 ° C. using a carbon tetrachloride/ dry ice bath followed by the dropwise addition of a solution containing 0.95 g (1.90 mmol) of (benzyloxycarbonyl)-L-valyl-2-L-(2,3-dihydro-1H-indole)-N-[1-(2-[5-(3-methylbenzyl)-1,3,4-oxadiazolyl]hydroxymethyl)-2-(S)-methylpropyl]amide in 20 mL of anhydrous toluene. The reaction was allowed to stir for 2 hours at −25 ° C. followed by the addition of 0.50 mL (3.6 mmol) of triethylamine. The cold bath was removed and the mixture was allowed to warm to room temperature. The reaction mixture was diluted with dichloromethane and washed with 1N HCl (2×), saturated sodium bicarbonate (2×) and water. The organic phase was dried over magnesium sulfate. The mixture was filtered and concentrated under reduced pressure to afford 0.61 g. The residue was purified by column chromatography on silica gel with 50% ethyl acetate/hexane to afford 0.27 g of material which was further purified via preparative HPLC to afford 196 mg (33.4%) of the title compound as a white solid. FAB MS [M+H] m/z Calcd: 652, Found 652.

The intermediate (benzyloxycarbonyl)-L-valyl-2-L-(2,3-dihydro-1H-indole)-N-[1-(2-[5-(3-methylbenzyl)-1,3,4-oxadiazolyl]hydroxymethyl)-2-(S)-methylpropyl]amide was prepared by the following procedures:

a. 2-L-Methyl (2,3-dihydroindole)carboxylate

To a suspension containing 5.00 g (30.6 mmol) of 2-L-(2,3-dihydroindole)carboxylic acid in 100 mL of anhydrous MeOH cooled to 0° C. was added a slow stream of HCl gas over 20 minutes. The resulting homogeneous solution was allowed to stir overnight warming to room temperature. The mixture was evaporated and the residue was crystallized from methanol/ether to afford, after drying, 5.58 g (85%) of 2-L-methyl (2,3-dihydroindole)carboxylate.

b. 2-Methyl [(S)-1-(N-[benzyloxycarbonyl]-L-valyl)-2,3-dihydro-1H-indole]carboxylate To a solution containing 3.00 g (14.0 mmol) of methyl (2,3-dihydroindole)-L-2-carboxylate in 60 mL of anhydrous dichloromethane, under a nitrogen atmosphere at 0° C., 7.15 g (28.8 mmol) of BOPCl and 7.72 mL (70.2 mmol) of DIEA was added a solution of 7.06 g (28.08 mmol) of Cbz-Val-OH in 40 mL of anhydrous dichloromethane and 3 mL of DMF. After stirring for 3 days at 5° C. the mixture was diluted with ethyl acetate and washed with 1N HCl (2×) and brine. The mixture was filtered and evaporated under reduced pressure. The residue was purified by column chromatography on silica gel using a gradient of 9:1 to 1:1 hexane/ethyl acetate to afford 4.85 g (87%) of the title compound as a white foam.

c. 2-[(S)-1-(N-[Benzyloxycarbonyl]-L-valyl)-2,3-dihydro-]-1H-indole]carboxylic acid.

To a solution containing 4.85 g (12.17 mmol) of 2-methyl [(S)-1-(N-[benzyloxycarbonyl]-L-valyl)-2,3-dihydro-1H-indole]carboxylate in 45 mL of THF and 15 mL of MeOH at 0° C. was added 15.8 mL of 1N LiOH dropwise. After 30 minutes 1N HCl was added to pH 2 and the mixture extracted with ethyl acetate (3×). The combined organic phases were dried over magnesium sulfate, filtered and evaporated under reduced pressure to afford 4.51 g (93%) of the title compound as a white solid.

d. (Benzyloxycarbonyl)-L-valyl-2-L-(2,3-dihydro-1H-indole)-N-[1-(2-[5-(3-methylbenzyl)-1,3,4-oxadiazolyl] hydroxymethyl)-2-(S)-methylpropyl]amide To a solution containing 1.09 g (3.96 mmol) of 1-[2-(5-[3-methylbenzyl])-1,3,4-oxadiazolyl]-2-(S)-amino-3-methylbutan-1-ol and 1.31 g (3.3 mmol) of 2-[(S)-1-(N-[benzyloxycarbonyl]-L-valyl)-2,3-dihydro-1H-indole] carboxylic acid in 30 mL of anhydrous dichloromethane was added 1.21 mL (6.93 mmol) of DIEA and 0.49 g (3.63 mmol) of HOBT. The mixture was cooled to 0° C. and 0.70 g (3.63 mmol) of EDCI was added and the reaction mixture was allowed to stir overnight. An additional 1.0 mL (7.44 mmol) of TEA was added and the reaction again allowed to stir overnight. The reaction was diluted with dichloromethane and washed with 1N HCl (2×), saturated sodium bicarbonate (2×) and water. The organic phase was dried over magnesium sulfate, filtered and evaporated under reduced pressure. The residue was purified by column chromatography on silica gel with 80% ethyl acetate/hexane to afford 0.66 g (30%) of the title compound.

Example 31

(CE-2125)

(Benzyloxycarbonyl)-L-valyl-2-L-(2,3-dihydro-1H-indole)-N-[1-(3-[5-(3-trifluoromethylbenzyl)-1,2,4-oxadiazolyl]carbonyl)-2-(S)-methylpropyl]amide Prepared in a similar manner as in Example 30. FAB MS [M+H] m/z; Calcd: 706, Found: 706.

Example 32

(CE-2143)

Acetyl-2-L-(2,3-dihydro-1H-indole)-N-[1-(3-[5-(3-trifluoromethylbenzyl)-1,2,4-oxadiazolyl]carbonyl)-2-(S)-methylpropyl]amide Prepared in a similar manner as in Example 30. FAB MS [M+H] m/z; Calcd: 515, Found: 515.

Example 33

(CE-2165)

Acetyl-2-L-(2,3-dihydro-1H-indole)-N-[1-(2-[5-(3-methylbenzyl)-1,3,4-oxadiazolyl]carbonyl)-2-(S)-methylpropyl]amide Prepared in a similar manner as in Example 30. FAB MS [M+H] m/z; Calcd: 461; Found: 461.

Example 34

(CE-2104)

(Morpholino-N-carbonyl)-L-valyl-N-[1-(2-[5-(3-methylbenzyl)-1,3,4-oxadiazolyl]carbonyl)-2-(S)-methylpropyl]-L-prolinamide To a mixture containing 0.69 g (5.17 mmol) of N-chlorosuccinimide in 60 mL of anhydrous toluene at 0° C. under a nitrogen atmosphere was added 0.60 mL (8.17 mmol) of dimethyl sulfide. The reaction was cooled to −25° C. using a carbon tetrachloride/ dry ice bath, followed by the addition of a solution containing (morpholino-N-carbonyl)-L-valyl-N-[1-(2-[5-(3-methyl benzyl)-1,3,4-oxadiazolyl]hydroxymethyl)-2-(S-)methyl propyl]-L-prolinamide (0.75 g, 1.28 mmol) in 10 mL of anhydrous toluene. The reaction was allowed to stir for 2 hours at −25° C. followed by the addition of 1.1 mL (0.83 g, 7.89 mmol) of triethylamine. The cold bath was removed and the reaction was allowed to warm to room temperature over 20 minutes. The reaction was diluted with ethyl acetate and washed with water. The organic phase was dried over magnesium sulfate and filtered. The solvents were evaporated in vacuo and the residue purified by column chromatography, 70% ethyl acetate/hexane on silica gel. Final purification was performed by preparative HPLC to afford 405 mg (54.3%) of the title compound as a white solid. FAB MS [M+H] m/z; Calcd: 583, Found: 583.

The intermediate (Morpholino-N-carbonyl)-L-valyl-N-[1-(2-[5-(3-methylbenzyl)-1,3,4-oxadiazolyl]hydroxymethyl)-2-(S)-methylpropyl]-L-prolinamide was prepared as follows:
a. (Morpholino-N-carbonyl)-L-valyl-L-proline-O-t-butyl ester To a solution containing L-valyl-L-proline-O-t-butyl-ester (1.80 g, 5.87 mmol) in 80 mL of anhydrous methylene chloride and 1.5 mL (13.64 mmol) of N-methyl morpholine under a nitrogen atmosphere at 0° C. was added morpholine carbonyl chloride dropwise. The mixture was allowed to warm to room temperature overnight. The reaction was diluted with methylene chloride and washed with water. The organic layer was dried over magnesium sulfate, filtered and evaporated.

The residue was purified by column chromatography on silica gel with 10% methanol/dichloromethane to afford 1.98 g (88%) of the title compound as a white solid. FAB MS [M+H] m/z; Calcd: 384, Found 384.
b. (Morpholino-N-carbonyl)-L-valyl-L-proline To a solution containing (morpholino-N-carbonyl)-L-valyl-L-proline-O-t-butyl ester (2.0 g, 5.22 mmol) in 80 mL of anhydrous methylene chloride under a nitrogen atmosphere at 0° C. was added trifluoroacetic acid (13 mL, 130 mmol). The mixture was allowed to warm to room temperature overnight and the solvents were evaporated in vacuo to give 2.26 g of a viscous oil. The material was used without further purification.
c. (Morpholino-N-carbonyl)-L-valyl-N-[1-(2-[5-(3-methylbenzyl)-1,3,4-oxadiazolyl]hydroxymethyl)-2-(S)-methylpropyl]-L-prolinamide To a solution containing 0.95 g (2.90 mmol) of (morpholino-N-carbonyl)-L-valyl-Proline in 25 mL of anhydrous dichloromethane under a nitrogen atmosphere at 0° C. was added 0.80 g (3.14 mmol) of BOPCl and 1.5 mL (8.61 mmol) of DIEA. After 30 minutes, 0.75 g (2.41 mmol) of 1-[2-(5-[3-methylbenzyl])-1,3,4-oxadiazolyl]-2-(S)-amino-3-methylbutan-1-ol hydrochloride in 10 mL of dichloromethane and 1.1 mL (6.31 mmol) of DIEA were added. The reaction was allowed to stir at 0° C. overnight. The reaction was diluted with dichloromethane and washed with a saturated NaHCO$_3$ solution. The organic phase was dried over magnesium sulfate and filtered. The mixture was concentrated in vacuo and the residue purified by column chromatography on silica gel using 6% methanol/dichloromethane to afford 0.77 g (54.84%) of the title compound as a white solid. FAB MS [M+H] m/z; Calcd: 585, Found: 585.

Example 35

(CE-2079)

3-(S)-(Benzyloxycarbonyl)amino)-ε-lactam-N-[1-(2-[5-(3-methylbenzyl)-1,3,4-oxadiazolyl]carbonyl)-2-(S)-methylpropyl]acetamide To a mixture containing 2.37 g (17.75 mmol) of N-chlorosuccinimide in 100 mL of anhydrous toluene at 0° C. under a nitrogen atmosphere was added 1.94 mL (2.64 mmol) of dimethyl sulfide. The reaction was cooled to −25° C. using a carbon tetrachloride/dry ice bath, followed by the dropwise addition of a solution containing 2.5 g (4.44 mmol) of 3-(S)-[(benzyloxycarbonyl)amino]-ε-lactam-N-[1-(2-[5-(3-methylbenzyl)-1,3,4-oxadiazolyl]hydroxymethyl)-2-(S)-methyl propyl]acetamide in 20 mL of anhydrous toluene. Upon complete addition, the reaction was to stirred at −25° C. for 2 hours, followed by the addition of 3.0 mL (21.52 mmol) of triethylamine. The cold bath was removed and the reaction warmed to room temperature and stirred for 30 minutes. The reaction was diluted with ethyl acetate and washed with water. The organic phase was dried over magnesium sulfate. Filtration, removal of solvent and column chromatography of the residue on silica gel with 5% methanol/dichloromethane afforded 1.8 g of a pale yellow solid. Subsequent preparative HPLC gave 950 mg (38.1%) of the title compound as a white solid. FAB MS [M+H] m/z; Calcd: 562, Found: 562.

The intermediate 3-(S)-[(benzyloxycarbonyl)amino]-ε-lactam-N-[1-(2-[5-(3-methylbenzyl)-1,3,4-oxadiazolyl]hydroxymethyl)-2-(S)-methyl propyl]acetamide was prepared as follows:
a. 3-(S)-[(Benzyloxycarbonyl)amino]-ε-lactam To a mixture containing 9.9 g (37.18 mmol) of Cbz-ornithine in 150 mL of acetonitrile under a nitrogen atmosphere was added 78 mL (369.70 mmol) of hexamethyldisilazane. The reaction was heated at reflux for 48 hours. The reaction mixture was cooled to room temperature and poured into 250 mL of cold methanol. The solvent was removed under reduced pressure. Chloroform was added and the mixture filtered through a plug of celite The filtrate was concentrated under reduced pressure and the residue dissolved in ethyl acetate. Hexane was added until the solution was slightly turbid and then allowed to stand overnight. The resultant solid was filtered and dried to afford 8.37 g (90.7%) of the title compound.
b. N-[3-(S)-(Benzyloxycarbonyl)amino]-ε-lactam-t-butyl acetate To a solution containing 1.0 g (4.03 mmol) of 3-(S)-[(benzyloxylcarbonyl)amino]-ε-lactam in 20 mL of anhydrous DMF under a nitrogen atmosphere was added 1.50 mL (10.16 mmol) of bromo-t-butyl acetate and 5 1.17 g (5.05 mmol) of silver oxide. The reaction was heated to 45° C. for 5 hours, diluted with acetonitrile and filtered through a pad of celite. The filtrate was concentrated under reduced pressure and the residue dissolved in ethyl acetate and washed with water. The organic phase was dried over magnesium sulfate. Filtration, removal of solvent and column chromatography of the residue on silica gel with 60% ethyl acetate/hexane afforded 1.18 g (80.79%) of the title compound. FAB MS [M+H] m/z; Calcd: 363, Found: 363.

c. N-[3-(S)-(Benzyloxycarbonyl)amino)-ε-lactam-carboxymethane

To a solution containing 0.55 g (1.52 mmol) of N-[3-(S)-(Benzyloxy carbonyl) amino]-ε-lactam-t-butyl acetate in 20 mL of dichloromethane under a nitrogen atmosphere at 0° C. was added 1.20 mL (15.58 mmol) of trifluoroacetic acid. The reaction was allowed to warm to room temperature overnight. The solvent was removed under reduced pressure. The residue was dissolved in ether acetate and washed with water. The organic phase was dried over magnesium sulfate. Filtration and removal of solvent afforded 0.50 of the title compound. FAB MS [M+H] m/z; Calcd: 307, Found: 307.

d. 3-(S)-[Benzyloxycarbonyl)amino)-ε-lactam-N-[1-(2-[5-(3-methylbenzyl)-1,3,4-oxadiazolyl]hydroxymethyl)-2-(S)-methylpropyl]acetamide To a solution containing 2.72 g (8.88 mmol) of N-[3-(S)-(Benzyloxycarbonyl)amino)-ε-lactam-carboxymethane in 80 mL of dichloromethane under a nitrogen atmosphere at 0° C. was added 2.37 g (9.31 mmol) of BOPCl and 1.60 mL (9.91 mmol) of DIEA. The reaction was allowed to stir at 0° C. for 30 minutes followed by the addition of 2.37 g (7.60 mmol) of 1-[3-[5-(3-methyl benzyl)-1,3,4-oxadiazolyl]-2-(S)-amino-3-methyl butan-1-ol hydrochloride in 20 mL of dichloromethane and 1.60 mL (9.19 mmol) of DIEA. The reaction was allowed to stir at 0° C. overnight. The reaction was diluted with dichloromethane and washed with water. The organic phase was dried over magnesium sulfate. Filtration, removal of solvent and column chromatography of the residue on silica gel with 10% methanol/dichloromethane afforded 2.58 g (50.23%) of the title compound. FAB MS [M+H] m/z; Calcd: 564, Found: 564.

Example 36

(CE-2080)

3-(S)-(Amino)-ε-lactam-N-[1-(2-[5-(3-methylbenzyl)-1,3,4-oxadiazolyl]carbonyl)-2-(S)-methylpropyl]acetamide trifluoroacetic acid salt This compound was prepared via deprotection of 3-(S)-[benzyloxycarbonyl]amino-ε-lactam-N-[1-(2-[5-(3-methylbenzyl)-1,3,4-oxadiazolyl]carbonyl)-2-(S)-methyl propyl]acetamide under standard conditions to one skilled in the art to afford the title compound. FAB MS [M+H] m/z; Calcd: 428, Found: 428.

Example 37

(CE-2091)

3-(S)-[(4-morpholino carbonyl-butanoyl)amino]-ε-lactam-N-[1-(2-[5-(3-methylbenzyl)-1,3,4-oxadiazolyl]carbonyl)-2-(R,S)-methylpropyl]acetamide To a solution containing 0.089 g (0.475 mmol) of 4-morpholino carbonyl butanoic acid in 10 mL of dichloromethane under a nitrogen atmosphere at 0° C. was added 0.127 g (0.498 mmol) of BOPCl and 0.09 mL (0.492 mmol) of DIEA. The reaction was allowed to stir for 30 minutes followed by the addition of 0.22 g (0.406 mmol) of 3-(S)-amino-ε-lactam-N-[1-(2-[5-(3-methyl benzyl)-1,3,4-oxadiazolyl]carbonyl)-2-(R,S)-methyl propyl]acetamide trifluoroacetic acid salt. The reaction was allowed to stir at 0° C. overnight. The reaction was diluted with dichloromethane and washed with water. The organic phase was dried over magnesium sulfate. Filtration, removal of solvent and purification via preparative HPLC afforded 0.044 g (18%) of the title compound. FAB MS [M+H] m/z; Calcd: 597, Found: 597.

Example 38

(CE-2087)

6-[4-Fluorophenyl]-ε-lactam-N-[1-(2-[5-(3-methylbenzyl)-1,3,4-oxadiazolyl]carbonyl)-2-(S)-methylpropyl]acetamide To a mixture containing 0.70 g (5.24 mmol) and N-chlorosuccinimide in 30 mL of anhydrous toluene at 0° C. under a nitrogen atmosphere was added 0.60 mL (8.17 mmol) of dimethyl sulfide. The reaction was cooled to −25° C. using a carbon tetrachloride/dry ice bath, followed by the dropwise addition of a solution containing 0.67 g (1.32 mmol) of 6-[4-fluorophenyl]-ε-lactam-N-[1-(2-[5-(3-methyl benzyl)-1,3,4-oxadiazolyl]hydroxymethyl)-2-(S)-methylpropyl]acetamide in 15 mL of anhydrous toluene. Upon complete addition, the reaction was allowed to stir at −25° C. for 2 hours followed by the addition of 0.90 mL (6.46 mmol) of triethylamine. The cold bath was removed and the reaction allowed to warm to room temperature and maintained for 20 min. The reaction was diluted with ethyl acetate and washed with water. The organic phase was dried over magnesium sulfate. Filtration, removal of solvent under reduced pressure and column chromatography of the residue on silica gel with 10% methanol/dichloromethane afforded 0.61 g of a pale yellow solid. Subsequent preparative HPLC gave 338 mg (50.5%) of the title compound. FAB MS [M+H] m/z; Calcd: 507, Found: 507.

The intermediate 6-[4-fluorophenyl]-ε-lactam-N-[1-(2-[5-(3-methylbenzyl)-1,3,4-oxadiazolyl]hydroxymethyl)-2-(S)-methylpropyl]acetamide was prepared as follows:

a. 6-[4-Fluorophenyl]-6-carboxymethylene-2-piperidinone

To a solution containing 2.15 g (8.11 mmol) of 6-[4-fluorophenyl]-1-carbomethoxymethylene-2-piperidinone, prepared in a similar fashion to that reported by Compernolle (*Tetrahedron*, 1993, 49, 3193) in 70 mL of methanol and 20 mL of water under a nitrogen atmosphere was added 0.55 g (13.11 mmol) of lithium hydroxide. The reaction was allowed to stir at room temperature for 2 hours. The solvent was removed under reduced pressure. The residue was diluted with water and washed with ethyl acetate. The aqueous phase was acidified with 1N hydrochloric acid and extracted with ethyl acetate. The organic phase was dried over magnesium sulfate. Filtration and removal of solvent afforded 2.0 g (98.2%) of the title compound. FAB MS [M+H] m/z; Calcd: 252, Found: 252.

b. 6-[4-Fluorophenyl]-ε-lactam-N-[1-(2-[5-(3-methylbenzyl)-1,3,4oxadiazolyl]hydroxymethyl)-2-(S)-methylpropyl]acetamide To a solution containing 1.04 g (4.14 mmol) of 6-[4-fluorophenyl]-6-carboxymethylene-2-piperidinone in 25 mL of anhydrous dichloromethane under a nitrogen atmosphere at 0° C. was added 1.10 g (4.32 mmol) of BOPCl and 0.80 mL (4.59 mmol) of DIEA. After stirring for 30 minutes, a solution containing 1.1 g (3.53 mmol) of 1-[2-(5-[3-methylbenzyl])-1,3,4-oxadiazolyl]-2-(S)-amino-3-methylbutan-1-ol hydrochloride in 10 mL of dichloromethane and 1.10 mL (6.31 mmol) of DIEA. The reaction was allowed to stir at 0° C. overnight. The reaction was diluted with dichloromethane and washed with a saturated sodium bicarbonate solution. The organic phase was dried over magnesium sulfate. Filtration, removal of solvent under reduced pressure and column chromatography of the residue on silica gel with 10% methanol/dichloromethane afforded 736 mg (41.0%) of the title compound. FAB MS [M+H] m/z; Calcd: 509, Found: 509.

Example 39

(CE-2121)

2-[2-(R,S)-Phenyl-4-oxothiazolidin-3-yl]-N-[1-(2-[5-(3-methylbenzyl)-1,3,4-oxadiazolyl]carbonyl)-2-(S)-methylpropyl]acetamide To a mixture containing 2.05 g (15.38 mmol) of N-chlorosuccinimide in 250 mL of anhydrous toluene at 0C under a nitrogen atmosphere was added 1.70 mL (23.06 mmol) of dimethyl sulfide. The reaction was cooled to −25° C. using a carbon tetrachloride/dry ice bath, followed by the addition of 1.90 g (3.84 mmol) of 2-[2-(R,S)-phenyl-4-oxothiazolidin-3-yl]-N-[1-(2-[5-(3-methylbenzyl)-1,3,4-oxadiazolyl]hydroxymethyl)-2-(S)-methylpropyl]acetamide in 20 mL of anhydrous toluene dropwise. The reaction was allowed to stir at −25° C. for 2 hours, followed by the addition of 2.52 mL (18.07 mmol) of triethylamine. The cold bath was removed and the reaction allowed to warm to room temperature over 40 minutes. The reaction was diluted with ethyl acetate and washed with water. The organic phase was dried over magnesium sulfate. Filtration, removal of solvent and column chromatography of the residue on silica gel with 60% ethyl acetate/hexane afforded 1.10 g of a yellow oil. Which was further purified via preparative HPLC to give 0.45 g (24%) of the title compound as an off-white solid. FAB MS [M+H] m/z; Calcd: 493, Found: 493.

The intermediate 2-[2-(R,S)-phenyl-4-oxothiazolidin-3-yl]-N-[1-(2-[5-(3-methylbenzyl)-1,3,4-oxadiazolyl]hydroxymethyl)-2-(S)-methylpropyl]acetamide was prepared as follows: to a solution containing 1.78 g (7.51 mmol) of 2-(2-phenyl-4-oxothiazolidin-3-yl) acetic acid, prepared according to Holmes (*J. Org. Chem*, 1995, 60, 7328), in 80 mL of dichloromethane under a Nitrogen atmosphere at 0° C. was added 2.04 g (8.02 mmol) of BOPCl and 1.35 mL (7.76 mmol) of DIEA. After stirring for 30 minutes, 2.0 g (6.41 mmol) of 1-[3-[5-(3-methylbenzyl)]-1,3,4-oxadiazolyl]-2-(S)-amino-3-methyl-butan-1-ol hydrochloride in 50 mL of dichloromethane and 1.35 mL (7.76 mmol) of DIEA was added. The reaction was allowed to stir at 0° C. overnight. The reaction mixture was diluted with dichloromethane and washed with water. The organic phase wad dried over magnesium sulfate, filtered and concentrated under reduced pressure. Column chromatography of the residue on silica gel with 4% methanol/dichloromethane afforded 2.30 g of a yellow foam. Subsequent preparative HPLC gave 1.9 g of the title compound. FAB MS [M+H] m/z; Calcd: 495, Found: 495.

Example 40

(CE-2122)

2-[2-(R,S)-Benzyl-4-oxothiazolidin-3-yl]-N-[1-(2-[5-(3-methylbenzyl)-1,3,4-oxadiazolyl]carbonyl)-2-(S)-methylpropyl]-acetamide was prepared in a similar manner as in Example 39. FAB MS [M+H] m/z; Calcd: 507, Found: 507.

Example 41

(CE-2136)

2-[(2-(R,S)-Benzyl-4-oxothiazolidin-3-yl oxide]-N-[1-(2-[5-(3-methyl benzyl)-1,3,4-oxadiazolyl]carbonyl)-2-(R,S)-methylpropyl]acetamide To a solution containing 1.31 g (2.59 mmol) of 2-[2-(R,S)-benzyl-4-oxothiazolidin-3-yl)-N-[1-(2-[5-(3-methylbenzyl)-1,3,4-oxadiazolyl]carbonyl)-2-(S)-methyl propyl]-acetamide in 15 mL of methanol under a nitrogen atmosphere was added 0.51 mL (5.17 mmol) of 30% hydrogen peroxide. The reaction was allowed to stir at room temperature overnight and then partitioned between brine and dichloromethane. The organic phase was dried over magnesium sulfate. Filtration, removal of solvent under reduced pressure and column chromatography of the residue on silica gel with 85% ethyl acetate/hexane afforded 0.73 g of a tan oil. Subsequent preparative HPLC gave 0.54 g (48%) of the title compound. FAB MS [M+H] m/z; Calcd: 523, Found 523.

Example 42

(CE-2137)

2-[2-(R,S)-Benzyl-4-oxothiazolidin-3-yl oxide]-N-[1-(3-[5-(3-trifluoromethylbenzyl)-1,2,4-oxadiazolyl]carbonyl)-2-(R,S)-methylpropyl] acetamide Prepared in a similar manner as in Example 41. FAB MS [M+H] m/z; Calcd: 577, Found 577.

Example 43

(CE-2118)

2-[2-(R,S)-Phenyl-4-oxometathiazan-3-yl]-N-[1-(2-[5(3-methylbenzyl)-1,3,4-oxadiazolyl]carbonyl)-2-(S)-methylpropyl]acetamide Prepared in a similar manner as in Example 39. FAB MS [M+H] m/z; Calcd: 507, Found: 507.

Example 44

(CE-2140)

(1-Benzoyl-3,8-quinazolinedione)-N-[1-(2-[5-(3-methylbenzyl)-1,3,4-oxadiazolyl]carbonyl)-2-(S)-methylpropyl]acetamide To a mixture containing 1.70 g (2.74 mmol) of N-chlorosuccinimide in 75 mL of anhydrous toluene at 0° C. under a nitrogen atmosphere was added 1.70 mL (23.15 mmol) of dimethyl sulfide. The reaction was cooled to −25° C. using a carbon tetrachloride/dry ice bath, followed by the addition of 1.90 g (3.27 mmol) of (1-Benzoyl-3,8-quinazolinedione)-N-[1-(2-[5-(3-methylbenzyl)-1,3,4-oxadiazolyl]hydroxymethyl)-2-(S)-methyl propyl] acetamide in 10 mL of toluene dropwise. The reaction was allowed to stir at −25 ° C. for 2 hours, followed by the addition of 3.20 mL (22.96 mmol) of triethylamine. The cold bath was removed and the reaction allowed to warm to room temperature and maintained for 15 minutes. The reaction was diluted with ethyl acetate and washed with water. The organic phase was dried over magnesium sulfate, filtered, and the solvent removed under reduced pressure. The residue was chromatographed on silica gel with 5% methanol/dichloromethane to afford 1.37 g of a brown oil. This was further purified via preparative HPLC to give 450 mg (40.10%) of the title compound. FAB MS [M+H] m/z; Calcd: 580, Found: 580.

The intermediate (1-benzoyl-3,8-quinazolinedione)-N-[1-(2-[5-(3-methylbenzyl)-1,3,4-oxadiazolyl]hydroxymethyl)-2-(S)-methylpropyl]acetamide was prepared as follows:

a. 1-Benzoyl-3,8-quinazolinedione-2-t-butyl acetate

To a solution containing 5.0 g (18.78 mmol) of 1-Benzoyl-3,8-quinazolinidione prepared in a similar manner to that reported by Melnyk et al. (*Tetrahedron Lett.,* 1996, 37, 4145), in 100 mL of DMF under a nitrogen atmosphere was added 4.30 mL (29.12 mmol) of bromo t-butylacetate and 5.4 (23.30 mmol) of silver oxide. The reaction was heated to 50° C. overnight, diluted with ethyl acetate and washed with water. The organic phase was dried over magnesium sulfate. Filtration, removal of solvent under reduced pressure and column chromatography of the residue on silica gel with 40% ethyl acetate/hexane gave 5.25 g (73.49%) of product. FAB MS [M+H] m/z; Calcd: 381, Found: 381.

b. 1-Benzoyl-2-carboxymethylene-3, 8-quinazolinedione

To a solution containing 5.20 g (13.67 mmol) of 1-benzoyl-3,8-quinazolinedione-2-t-butyl acetate in 300 mL of dichloromethane under a nitrogen atmosphere at 0° C. was added 21.0 mL (211.44 mmol) of trifluoroacetic acid. The reaction was allowed to warm to room temperature overnight. The solvent was removed under reduced pressure and the residue dissolved in ethyl acetate and washed with water. The organic phase was dried over magnesium sulfate. Filtration and removal of solvent afforded 4.32 g (97.45%) of the title compound. FAB MS [M+H] m/z; Calcd: 325, Found: 325.

c. (1-Benzoyl-3,8-quinazolinedione)-N-[1-(2-[5-(3-methylbenzyl)-)-3,4-oxadiazolyl]hydroxymethyl)-2-(S)-methylpropyl]acetamide To a solution containing 1.80 g (5.55 mmol) of 1-benzoyl-2-carboxymethylene-3,8-quinazolinedione in 100 mL of anhydrous dichloromethane and 5 mL of DMF under a nitrogen atmosphere at 0° C. was added 1.90 g (7.46 mmol) of BOPCl and 1.40 mL (8.05 mmol) of DIEA. After stirring for 30 minutes, a solution containing 1.70 g (5.45 mmol) of 1-[2-(5-[3-methylbenzyl])-1,3,4-oxadiazolyl]-2-(S)-amino-3-methylbutan-1-ol hydrochloride in 20 mL of dichloromethane and 3.80 mL (21.84 mmol) of DIEA was added. The reaction was allowed to stir at 0° C. overnight, diluted with dichloromethane and washed with water. The organic phase was dried over magnesium sulfate. Filtration, removal of solvent under reduced pressure and column chromatography of the residue on silica gel with 10% methanol/dichloromethane afforded 1.93 (60.9%) of the title compound. FAB MS [M+H] m/z; Calcd: 582, Found: 582.

Example 45

(CE-2138)

(1-Benzoyl-3,6-piperazinedione)-N-[1-(2-[5-(3-methylbenzyl)-1,3,4-oxadiazolyl]carbonyl)-2-(S)-methylpropyl]acetamide Prepared in a similar manner as in Example 44. FAB MS [M+H] m/z; Calcd: 532, Found: 532.

Example 46

(CE-2147)

(1-Phenyl-3,6-piperazinedione)-N-[1-(2-[5-(3-methylbenzyl)-1,3,4-oxadiazolyl]carbonyl)-2-(S)-methylpropyl]acetamide Prepared in a similar manner as in Example 44. FAB MS [M+H] m/z; Calcd: 504, Found: 504.

Example 47

(CE-2148)

[(1-Phenyl-3,6-piperazinedione)-N-[1-(3-[5-(3-trifluoromethylbenzyl)-1,2,4-oxadiazolyl]carbonyl)-2-(S)-methylpropyl]acetamide Prepared in a similar manner as in Example 44. FAB MS [M+H] m/z; Calcd: 558, Found: 558.

Example 48

(CE-2108)

3-[(Benzyloxycarbonyl)amino]-quinolin-2-one-N-[1-(2-[5-(3-methybenzyl)-1,3,4-oxadiazolyl]carbonyl)-2-(S)-methylpropyl]acetamide To a mixture containing 0.16 g (1.18 mmol) of N-chlorosuccinimide in 20 mL of anhydrous toluene at 0° C. under a nitrogen atmosphere was added 0.13 mL (1.77 mmol) of dimethyl sulfide. The reaction was cooled to −25° C. using a carbon tetrachloride/dry ice bath followed by the addition of a solution containing 0.18 g (0.30 mmol) of 3-[(benzyloxycarbonyl)amino]-quinolin-2-one-N-[1-(2-[5-(3-methylbenzyl)-1,3,4-oxadiazolyl]hydroxymethyl)-2-(S)-methylpropyl]acetamide in 20 mL of methylene chloride dropwise. The reaction was allowed to stir at −25 ° C. for 2 hours, followed by the addition of 0.19 mL (1.38 mmol) of triethylamine. The cold bath was removed and the reaction was allowed to warm to room temperature and maintained for 30 minutes. The reaction was diluted with ethyl acetate and washed with water. The organic phase was dried over magnesium sulfate. Filtration, removal of solvent under reduced pressure and column chromatography of the residue on silica gel with 3% methanol/dichloromethane afforded 0.23 g of an oil. Further purification via preparative HPLC gave 100 mg of the title compound.

FAB MS [M+H] m/z; Calcd: 608, Found: 608

The intermediate 3-[(benzyloxycarbonyl)amino]-quinolin-2-one-N-[1-(2-[5-(3-methylbenzyl)-1,3,4-oxadiazolyl]hydroxymethyl)-2-(S)-methylpropyl]acetamide was prepared as follows:

a. 3-[(Benzyloxycarbonyl)amino]-quinoline-2-one

To a solution containing 0.5 g (3.10 mmol) of 3-amino-quinolin-2-(1H)-one described by Anderson, et. al. (*J Heterocyclic Chem.,* 1993, 30, 1533) in 40 mL of dioxane under a nitrogen atmosphere was added 0.14 g (3.4 mmol) of sodium hydroxide in 14 mL of water. The reaction mixture was cooled to 0° C., followed by the addition of 0.50 mL (3.4 mmol) of benzylchloroformate. The pH of the reaction was maintained above 8.0 with additional I N sodium hydroxide. The reaction was allowed to warm to room temperature and stirred for 2 hours. The reaction was diluted with methylene chloride and washed with water. The organic phase was dried over magnesium sulfate. Filtration, removal of solvent under reduced pressure and column chromatography of the residue on silica gel with 2% methanol/dichloromethane afforded 0.32 g (35%) of product as a white solid. FAB MS [M+H] m/z; Calcd: 295, Found: 295 b. 3-[(Benzylcarbonyl)amino]-quinolin-2-one-N-t-butyl-acetate

To a solution containing 0.30 g (1.02 mmol) of 3-[(benzyloxycarbonyl)amino]-quinolin-2-one in 20 mL of DMF under a nitrogen atmosphere was added 0.15 mL (1.02 mmol) of t-butyl bromoacetate and 0.24 g (1.02 mmol) of silver oxide. The reaction was heated to 70° C. and maintained overnight. The reaction mixture was diluted with acetonitrile and filtered through a pad of celite. The filtrate was concentrated under reduced pressure and the residue partitioned between ethyl acetate and water. The organic phase was dried over magnesium sulfate. Filtration, removal of solvent under reduced pressure and column chromatography of the residue on silica gel with dichloromethane afforded 0.20 g (48%) of product as a white solid. FAB MS [M+H] m/z; Calcd: 409, Found: 409.

c. 3-[(Benzyloxycarbonyl)amino]-1-carboxymethylene-quinolin-2-one

To a solution containing 1.30 g (3.18 mmol) of 3-[(benzyloxycarbonyl)amino]-quinolin-2-one-N-t-butyl-acetate in 35 mL of dichloromethane under a nitrogen atmosphere at 0° C. was added 2.45 mL (31.84 mmol) of trifluoroacetic acid. The reaction was allowed to warm to room temperature overnight. The solvent was removed under reduced pressure to afford 1.09 g (97%) of the title compound. FAB MS [M+H] m/z; Calcd: 353, Found: 353
d. 3-[(Benzyloxycarbonyl)amino]-quinolin-2-one-N-[1-(2-[5-(3-methylbenzyl)-1,3,4-oxadiazolyl]hydroxymethyl)-2-(S)-methylpropyl]acetamide To a solution containing 1.09 g (3.09 mmol) of 3-[(benzyloxycarbonyl)amino]-1-carboxymethylene-quinolin-2-one in 50 mL of anhydrous dichloromethane and 3 mL of DMF under a nitrogen atmosphere at 0° C. was added 0.84 (3.31 mmol) of BOPCl and 1.10 mL (6.31 mmol) of DIEA. After stirring for 30 minutes, 0.82 g (2.65 mmol) of 1-[2-(5-[3-methylbenzyl])-1,3,4-oxadiazolyl]-2-(S)-amino-3-methylbutan-1-ol hydrochloride in 8 mL of dichloromethane and 0.56 mL (3.20 mmol) of DIEA was added. The reaction was allowed to stir at 0° C. overnight, diluted with dichloromethane and washed with water. The organic phase was dried over magnesium sulfate. Filtration, removal of solvent under reduced pressure and column chromatography of the residue on silica gel with 5% methanol/dichloromethane afforded 0.37 g (30.3%) of product. FAB MS [M+H] m/z; Calcd: 610; Found: 610

Example 49

(CE-2107)

3-[(Benzyloxycarbonyl)amino]-7-piperidinyl-quinolin-2-one-N-[1-(2-[5-(3-methybenzyl)-1,3,4-oxadiazolyl]carbonyl)-2-(S)-methylpropyl]acetamide Prepared in a similar manner as shown in Example 48. FAB MS [M+H] m/z; Calcd: 691, Found: 691

Example 50

(CE-2117)

3-Carbomethoxy-quinolin-2-one-N-[1-(2-[5-(3-methybenzyl)-1,3,4-oxadiazolyl]carbonyl)-2-(S)-methylpropyl]acetamide Prepared in a similar manner as shown in Example 48. FAB MS [M+H]m/z; Calcd: 535, Found: 535

Example 51

(CE-2113)

3-(Amino-quinolin-2-one)-N-[1-(2-[5-(3-methylbenzyl)-1,3,4-oxadiazolyl]carbonyl)-2-(S)-methylpropyl]acetamide To a solution containing 2.30 g (3.79 mmol) of 3-[(benzyloxycarbonyl)amino]-quinolin-2-one-N-[1-(2-[5-(3-methyl benzyl)-1,3,4-oxadiazolyl]-carbonyl)-2-(S)-methyl propyl[acetamide in 60 mL of trifluoroacetic acid under a nitrogen atmosphere at 0° C. was added 0.53 mL (4.54 mmol) of thioanisole. The reaction was allowed to warm to room temperature overnight. The solvent was removed under reduced pressure. Subsequent preparative HPLC afforded 0.61 g (27%) of the title compound. FAB MS [M+H] m/z; Calcd: 474, Found: 474

Example 52

(CE-2116)

3-[(4-Morpholino)aceto]amino-quinolin-2-one-N-[1-(2-[5-(3-methylbenzyl)-1,3,4-oxadiazolyl]carbonyl)-2-(S)-methylpropyl]acetamide To a solution containing 0.32 g (1.22 mmol) of 4-morpholino acetic acid in 18 mL of dichloromethane under a nitrogen atmosphere at 0° C. was added 0.33 g (1.30 mmol) of BOPCl and 0.22 mL (1.26 mmol) of DIEA. After stirring for 1.5 hours, a solution containing 0.61 g (1.04 mmol) of 3-(amino-quinolin-2-one)-N-[1-(2-[5-(3-methylbenzyl)-1,3,4-oxadiazolyl]carbonyl)-2-(S)-methylpropyl]acetamide in 20 mL of dichloromethane was added followed by 0.22 mL (1.26 mmol) of DIEA. The reaction was allowed to stir at 0° C. overnight, diluted with dichloromethane and washed with water. The organic phase was dried over magnesium sulfate. Filtration, removal of solvent under reduced pressure and preparative HPLC afforded 0.20 g (27%) of the title compound. FAB MS [M+H] m/z; Calcd: 602, Found: 602

Example 53

(CE-2088)

3,4-Dihydro-quinolin-2-one-N-[1-(2-[5-(3-methylbenzyl)-1,3,4-oxadiazolyl]carbonyl)-2-(S)-methylpropyl]acetamide from commercially available 3,4-Dihydro-2(1 H)-quinolin-2-one Prepared in a similar manner as shown in Example 52. FAB MS [M+H] m/z; Calcd: 461, Found: 461

Example 54

(CE-2099)

1-Acetyl-3-benzylidene piperazine-2,5-dione-N-[1-(2-[5-(3-methylbenzyl)-1,3,4-oxadiazolyl]carbonyl)-2-(S)-methylpropyl]acetamide To a solution containing 0.55 g (4.15 mmol) of N-chlorosuccinimide in 35 mL of anhydrous toluene at 0° C. under a nitrogen atmosphere was added 0.46 mL (6.22 mmol) of dimethyl sulfide. The reaction was cooled to −25° C. using a carbon tetrachloride/dry ice bath, followed by the addition of a solution containing 0.58 g (1.04 mmol) of 1-acetyl-3-benzylidene piperazine-2,5-dione-N-[ 1-(2-[5-(3-methylbenzyl)-1,3,4-oxadiazolyl]hydroxymethyl)-2-(S)-methylpropyl]acetamide in 8 mL of toluene. The reaction was allowed to stir at −25° C. for 2 h, followed by the addition of 0.68 mL (4.87 mmol) of triethylamine. The cold bath was removed and the reaction allowed to warm to room temperature and maintained for 40 minutes. The reaction was partitioned between ethyl acetate and water. The organic phase was dried over magnesium sulfate. Filtration, removal of solvent under reduced pressure and column chromatography of the residue on silica gel 60% ethyl acetate/hexane gave 0.54 g of a brown oil which was further purified via preparative HPLC to give 146 mg (25%) of the title compound. FAB MS [M+H] m/z; Calcd: 558, Found: 558

The intermediate 1-acetyl-3-benzylidene piperazine-2,5-dione-N-[1-(2-[5-(3 -methylbenzyl)-1,3,4-oxadiazolyl] hydroxymethyl)-2-(S)-methylpropyl]acetamide was prepared as follows:
a. 1-Acetyl-3-benzylidene piperazine-2,5-dione-N-t-butyl acetate To a solution containing 6.36 g (26.00 mmol) of 1-Acetyl-3-benzylidene piperazine-2,5-dione described by D. Villemn, et. al. (*Synthetic Communications*, 1990, 20, 3325), in 100 mL of DMF under a nitrogen atmosphere was added 9.62 mL (65.10 mmol) of t-butyl bromoacetate and 7.55 g (32.60 mmol) of silver oxide. The reaction was heated to 45° C. overnight. The reaction was filtered through a plug of celite and the filtrate concentrated under reduced pressure. The residue was diluted with ethyl acetate and washed with water. The organic phase was dried over magnesium sulfate. Filtration, removal of solvent under reduced pressure and column chromatography of the residue on silica gel with 1% methanol/dichloromethane gave 5.37 g of a tan solid. Further purification via preparative HPLC gave 2.5 g (27%) of the title compound. FAB MS [M+H] m/z; Calcd: 359, Found: 359 b. 1-Acetyl-3-benzylidene-4-carboxymethylene-piperazine-2,5-dione

To a solution containing 2.50 g (6.98 mmol) of 1-acetyl-3-benzylidene piperazine-2,5-dione-N-t-butyl acetate in 100 mL of dichloromethane under a nitrogen atmosphere at 0° C. was added 5.40 mL (69.80 mmol) of trifluoroacetic acid. The reaction was allowed to warm to room temperature overnight. The solvent was removed under reduced pressure and the residue diluted with ethyl acetate and washed with a saturated sodium bicarbonate solution. The aqueous phase was acidified with 1N hydrochloric acid and extracted with ethyl acetate. The organic phase was dried over magnesium sulfate. Filtration and removal of solvent under reduced pressure gave 1.96 g (96%) of product as a tan solid. FAB MS [M+H] m/z; Calcd: 303, Found: 303 c. 1-Acetyl-3-benzylidene piperazine-2,5-dione-N-[1-(2-[5-(3-methylbenzyl)-1,3,4-oxadiazolyl]hydroxymethyl)-2-(S)-methylpropyl]acetamide To a solution containing 0.65 g (2.14 mmol) of 1-acetyl-3-benzylidene-4-carboxymethylene-piperazine-2,5-dione in 40 mL of anhydrous dichloromethane and 3 mL of DMF under a nitrogen atmosphere at 0° C. was added 0.57 g (2.24 mmol) of BOPCl and 0.39 mL (2.21 mmol) of DIEA. After stirring for 30 minutes, a solution containing 0.57 g (1.83 mmol) of 1-[2-(5-[3-methylbenzyl])-1,3,4-oxadiazolyl]-2-(S)-amino-3-methylbutan-1-ol hydrochloride in 10 mL of dichloromethane and 0.39 mL (2.21 mmol) of DIEA. The reaction was allowed to stir at 0° C. overnight, diluted with dichloromethane and washed with water. The organic phase was dried over magnesium sulfate. Filtration, removal of solvent under reduced pressure and column chromatography of the residue on silica gel with 5% methanol/dichloromethane gave 0.13 g (58%) of product. FAB MS [M+H] m/z; Calcd: 560, Found: 560

Example 55

(CE-2105)

1-Acetyl-3-(4-fluorobenzylidene) piperazine-2,5-dione-N-[1-(2-[5-(3-methylbenzyl)-1,3,4-oxadiazolyl]carbonyl)-2-(S)-methylpropyl]acetamide Prepared in a similar manner as shown in Example 54. FAB MS [M+H] m/z; Calcd: 576, Found: 576

Example 56

(CE-21 11)

1-Acetyl-3-(4-dimethylamino benzylidene) piperazine-2,5-dione-N-[1-(2-[5-(3-methylbenzyl)-1,3,4-oxadiazolyl]carbonyl)-2-(S)-methylpropyl]acetamide Prepared in a similar manner as shown in Example 54. FAB MS [M+H] m/z; Calcd: 601, Found: 601.

Example 57

(CE-2112)

1-Acetyl-3-(4-carbomethoxy benzylidene) piperazine-2,5-dione-N-[1-(2-[5-(3-methylbenzyl)-1,3,4-oxadiazolyl]carbonyl)-2-(S)-methylpropyl]acetamide Prepared in a similar manner as shown in Example 54. FAB MS [M+H] m/z; Calcd: 616, Found: 616.

Example 58

(CE-2114)

1-Acetyl-3-[(4-pyridyl)methylene]piperazine-2,5-dione-N-[1-(2-[5-(3-methylbenzyl)-1,3,4-oxadiazolyl]carbonyl)-2-(S)-methylpropyl]acetamide Prepared in a similar manner as shown in Example 54. FAB MS [M+H]m/z; Calcd: 559, Found: 559.

Example 59

(CE-2144)

4-[1-Benzyl-3-(R)-benzyl-piperazine-2,5,-dione]-N-[1-(2-[5-(3-methylbenzyl)-1,3,4-oxadiazolyl]carbonyl)-2-(S)-methylpropyl]acetamide To a mixture containing 2.20 g (16.48 mmol) of N-chlorosuccinimide in 100 mL of anhydrous toluene under a nitrogen atmosphere at 0° C. was added 2.1 mL (28.59 mmol) of dimethyl sulfide. The reaction was cooled to −25° C. using a carbon tetrachloride/dry ice bath, followed by the addition of a solution containing 2.50 g (4.10 mmol) of 4-[1-benzyl-3-(R)-benzyl piperazine-2,5,-dione]-N-[1-(2-[5-(3-methylbenzyl)-1,3,4-oxadiazolyl]hydroxymethyl)-2-(S)-methylpropyl]acetamide in 15 mL of toluene. The reaction was allowed to stir at −25° C. for 2 hours, followed by the addition of 4.0 mL (28.70 mmol) of triethylamine. The cold bath was removed and the reaction allowed to warm to room temperature and maintained for 30 minutes. The reaction was diluted with ethyl acetate and washed with water. The organic phase was dried over magnesium sulfate. Filtration, removal of solvent under reduced pressure, and column chromatography of the residue on silica gel with 5% methanol/dichloromethane afforded 2.27 g of a light brown solid which was further purified via preparative HPLC to give 350 mg (14.4%) of the title compound. FAB MS [M+H] m/z; Calcd: 608, Found: 608

The intermediate 4-[1-benzyl-3-(R)-benzyl piperazine-2,5,-dione]-N-[1-(2-[5-(3-methylbenzyl)-1,3,4-oxadiazolyl]hydroxymethyl)-2-(S)-methylpropyl]acetamide was prepared as follows:

a. 1-Benzyl-3-(R)-benzyl piperazine-2,5-dione-4-t-butyl acetate

To a solution containing 7.0 g (23.78 mmol) of 1-benzyl-3-(R)-benzyl piperazine-2,5-dione described by Steele, et. al. (J. Biorg. Med. Chem. Lett., 1995, 5, 47) in 125 mL of DMF under a nitrogen atmosphere was added 5.30 mL (35.89 mmol) of t-butyl bromoacetate and 6.80 g (29.34 mmol) of silver oxide. The reaction was heated to 50° C. overnight, diluted with ethyl acetate and washed with water. The organic phase was dried over magnesium sulfate. Filtration, removal of solvent under reduced pressure and column chromatography of the residue on silica gel with 50% ethyl acetate/hexane afforded 7.74 g (79.7%) of the title compound as a white solid. FAB MS [M+H] m/z; Calcd: 409, Found: 409 b. 1-Benzyl-3-(R)-benzyl-4-carboxymethylene-piperazine-2,5-dione

To a solution containing 7.70 g (18.85 mmol) of 1-Benzyl-3-(R)-benzyl piperazine-2,5-dione-4-t-butyl acetate in 300 mL of dichoromethane under a nitrogen atmosphere at 0° C. was added 19.0 mL (191.30 mmol) of trifluoroacetic acid. The reaction was allowed to warm to room temperature overnight. The solvent was removed under reduced pressure and the residue dissolved in ethyl acetate and washed with water. The organic phase was dried over magnesium sulfate. Filtration and removal of solvent under reduced pressure afforded 6.69 g of product. FAB MS [M+H] m/z; Calcd: 353, Found: 353.

c. 4-[1-Benzyl-3(R)-benzylpiperazine-2,5,-dione]-N-[1-(2-[5-(3-methylbenzyl)-1,3,4-oxadiazolyl]hydroxymethyl)-2-(S)-methylpropyl]acetamide To a solution containing 2.0 g (5.68 mmol) of 1-Benzyl-3-(R)-benzyl-4-carboxymethylene-piperazine-2,5-dione in 100 mL of dichloromethane and 2 mL of DMF under a nitrogen atmosphere at 0° C. was added 2.0 g (7.86 mmol) of BOPCl and 1.50 mL (8.62 mmol) of DIEA. After stirring for 30 minutes, a solution containing 1.80 g (5.77 mmol) of 1-[2-(5-[3-methylbenzyl])-1,3,4-oxadiazolyl]-2-(S)-amino-3-methylbutan-1-ol hydrochloride in 10 mL of dichloromethane and 4.0 mL (22.99 mmol) of DIEA. The reaction was allowed to stir at 0° C. overnight, diluted with dichloromethane and washed with water. The organic phase was dried over magnesium sulfate. Filtration, removal of solvent under reduced pressure and column chromatography of the residue on silica gel with 7% methanol/dichloromethane afforded 2.69 g (77.7%) of product. FAB MS [M+H] m/z; Calcd: 610, Found: 610.

Example 60

(CE-2128)

4-[1-Benzyl-3-(S)-benzyl piperazine-2,5,-dione]-N-[1-(2-[5-(3-methylbenzyl)-1,3,4-oxadiazolyl] carbonyl)-2-(S)-methylpropyl]acetamide Prepared in a similar manner as shown in Example 59. FAB MS [M+H] m/z; Calcd: 608, Found: 608.

Example 61

(CE-2146)

4-[1-Benzyl-3(R)-benzylpiperazine-2,5,-dione]-N-[1-(3-[5-(3-trifluoromethylbenzyl)-1,2,4-oxadiazolyl]carbonyl)-2-(S)-methylpropyl]acetamide Prepared in a similar manner as shown in Example 59. FAB MS [M+H] m/z; Calcd: 662, Found: 662.

Example 62

(CE-2129)

4-[1-Benzyl-3-(S)-benzylpiperazine-2,5,-dione]-N-[1-(3-[5-(3-trifluoromethylbenzyl)-1,2,4-oxadiazolyl]carbonyl)-2-(S)-methylpropyl]acetamide Prepared in a similar manner as shown in Example 59. FAB MS [M+H] m/z; Calcd: 662, Found: 662.

Example 63

(CE-2133)

4-[1-Benzyl-3-(S)-benzyl piperazine-2,5,-dione]-N-[1-(3-[5-(2-dimethylaminoethyl)-1,2,4-oxadiazolyl] carbonyl)-2-(S)-methylpropyl]acetamide Prepared in a similar manner as shown in Example 59. FAB MS [M+H] m/z; Calcd: 575, Found: 575.

Example 64

(CE-2084)

4-[1-Methyl-3-(R,S)-phenylpiperazine-2,5,-dione]-N-[1-(3-[5-(3-trifluoromethylbenzyl)-1,2,4-oxadiazolyl]carbonyl)-2-(S)-methylpropyl]acetamide Prepared in a similar manner as shown in Example 59. FAB MS [M+H] m/z; Calcd: 572, Found: 572.

Example 65

(CE-2106)

4-[1-Methyl-3-(R,S)-phenyl piperazine-2,5,-dione]-N-[1-(2-[5-(3-methylbenzyl)-1,3,4-oxadiazolyl] carbonyl)-2-(S)-methylpropyl]acetamide Prepared in a similar manner as shown in Example 59. FAB MS [M+H] m/z; Calcd: 518, Found: 518.

Example 66

(CE-2162)

4-[1-(4-Morpholino ethyl)3-(R)-benzyl piperazine-2,5,-dione]-N-[1-(2-[5-(3-methylbenzyl)-1,3,4-oxadiazolyl]carbonyl)-2-(S)-methylpropyl]acetamide Prepared in a similar manner as shown in Example 59. FAB MS [M+H] m/z; Calcd: 631, Found: 631.

Example 67

(CE-2149)

5-(R,S)-Phenyl-2,4-imidazolidinedione-N-[1-(2-[5-(3-methylbenzyl)-1,3,4-oxadiazolyl]carbonyl)-2-(S)-methylpropyl]acetamide To a mixture containing 0.28 g (2.10 mmol) of N-chlorosuccinimide in 50 mL of anhydrous toluene under a nitrogen atmosphere at 0° C. was added 0.23 mL (3.13 mmol) of dimethyl sulfide. The reaction was cooled to −25° C. using a carbon tetrachloride/dry ice bath, followed by the addition of a solution containing 0.26 g (0.52 mmol) of 5-(R,S)-phenyl-2,4-imidazolidinedione-N-[1-(2-[5-(3-methylbenzyl)-1,3,4-oxadiazolyl]hydroxymethyl)-2-(S)-methylpropyl]acetamide in 10 mL of toluene. The reaction was allowed to stir at −25° C. for 2 hours, followed by the addition of 0.30 mL (2.15 mmol) of triethylamine. The cold bath was removed and the reaction allowed to warm to room temperature and maintained for 30 minutes. The reaction was diluted with ethyl acetate and washed with water. The organic phase was dried over magnesium sulfate. Filtration, removal of solvent under reduced pressure and column chromatography of the residue on silica gel with 10% methanol/dichloromethane, followed by preparative HPLC gave 120 mg (47.19%) of the title compound. FAB MS [M+H] m/z; Calcd: 490, Found: 490

The intermediate 5-(R,S)-phenyl-2,4-imidazolidinedione-N-[1-(2-[5-(3-methylbenzyl)-1,3,4-oxadiazolyl] hydroxymethyl)-2-(S)-methylpropyl]acetamide was prepared as follows:

a. (R)-N-(Ethoxy carbonylmethyl)-N'-(]-methoxy carbonyl-2-phenyl)urea

To a solution containing 18.45 g (91.49 mmol) of (R)-2-phenylglycine methylester in 250 mL of ethyl acetate and 13.4 mL (96.13 mmol) of triethylamine under a nitrogen atmosphere at 0° C. was added 10 mL (91.49 mmol) of ethyl isocyanatoacetate. After stirring for 1 h, the reaction was diluted with ethyl acetate and washed with water. The organic phase was dried over magnesium sulfate. Filtration and removal of solvent under reduced pressure afforded 29.28 g (97.60%) of product as a white solid. FAB MS [M+H] m/z; Calcd: 235, Found: 235.

b. (R)-5-Phenyl-3-carboxymethyl hydantoin

A mixture containing 29.28 g (99.49 mmol) of (R)-N-(ethoxy carbonylmethyl)-N'-(1-methoxy carbonyl-2- phenyl)urea in 500 mL of concentrated hydrochloric acid was heated to reflux overnight. The reaction mixture was cooled to room temperature and extracted with ethyl acetate. The organic phase was dried over magnesium sulfate. Filtration and removal of solvent under reduced pressure afforded 14.01 g (60%) of the title compound. FAB MS [M+H] m/z; Calcd: 295, Found: 295.

c. 5-(R,S)-Phenyl-2,4-imidazolidinedione-N-[1-(2-[5-(3-methylbenzyl)-1,3,4-oxadiazolyl]hydroxymethyl)-2-(S)-methylpropyl]acetamide To a solution containing 2.55 g (10.89 mmol) of (R)-5-phenyl-3-carboxymethyl hydantoin in 100 mL of dichloromethane and 10 mL of DMF under a nitrogen atmosphere at 0° C. was added 2.30 g (12.00 mmol) of EDCI and 1.62 g (11.99 mmol) of HOBT. After stirring for 30 minutes, a solution containing 4.43 g (14.21 mmol) of I-[2-(5-[3-methylbenzyl])-1,3,4-oxadiazolyl]-2-(S)-amino-3-methylbutan-1-ol hydrochloride in 20 mL of dichloromethane and 4.78 mL (43.50 mmol) of NMM. The reaction was allowed to warm to room temperature overnight, diluted with dichloromethane and washed with water. The organic phase was dried over magnesium sulfate. Filtration, removal of solvent under reduced pressure and column chromatography of the residue on silica gel with 50% acetone/dichloromethane afforded 1.90 g (35.5%) of the title compound. FAB MS [M+H] m/z; Calcd: 490, Found: 490.

Example 68

(CE-2154)

5-(R)-Benzyl-2,4-imidazolidinedione-N-[1-(2-[5-(3-methylbenzyl)-1,3,4-oxadiazolyl]carbonyl)-2-(S)-methylpropyl]acetamide Prepared in a similar manner as shown in Example 67. FAB MS [M+H] m/z; Calcd: 504, Found: 504.

Example 69

(CE-2142)

5-(S)-Benzyl-2,4-imidazolidinedione-N-[1-(2-[5-(3-methylbenzyl)-1,3,4-oxadiazolyl]carbonyl)-2-(S)-methylpropyl]acetamide Prepared in a similar manner as shown in Example 67. FAB MS [M+H] m/z; Calcd: 504, Found: 504.

Example 70

(CE-2141)

5-(S)-Benzyl-2,4-imidazolidinedione-N-[1-(3-[5-(3-trifluoromethylbenzyl)-1,2,4-oxadiazolyl]carbonyl)-2-(S)-methylpropyl]acetamide Prepared in a similar manner as shown in Example 67. FAB MS [M+H] m/z; Calcd: 558, Found: 558.

Example 71

(CE-2155)

5-(R)-Benzyl-2,4-imidazolidinedione-N-[1-(3-[5-(3-trifluoromethylbenzyl)-1,2,4-oxadiazolyl]carbonyl)-2-(S)-methylpropyl]acetamide Prepared in a similar manner as shown in Example 67. FAB MS [M+H] m/z; Calcd: 558, Found: 558.

Example 72

(CE-2151)

1-Benzyl-4-(R)-benzyl-2,5-imidazolidinedione-N-[1-(2-[5-(3-methylbenzyl)-1,3,4-oxadiazolyl]carbonyl)-2-(S)-methylpropyl]acetamide Prepared in a similar manner as shown in Example 67. FAB MS [M+H] m/z; Calcd: 594, Found: 594.

Example 73

(CE-2150)

1-Benzyl-4-(R)-benzyl-2,5-imidazolidinedione-N-[1-(3-[5-(3-trifluoromethylbenzyl)-1,2,4-oxadiazolyl]carbonyl)-2-(S)-methylpropyl]acetamide Prepared in a similar manner as shown in Example 67. FAB MS [M+H] m/z; Calcd: 648, Found: 648.

We claim:

1. A compound of the formula

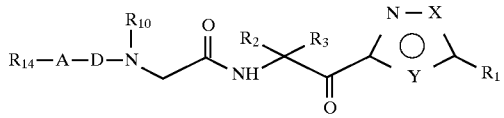

wherein

X and Y are O, N or S where at least one of X or Y is N;

$R_1$ is alkyl or alkenyl, optionally substituted with halo or hydroxy; alkynyl, alkyl-C(O)OCH$_3$, dialkylamino, or alkyldialkylamino; or cycloalkyl, alkylcycloalkyl, alkenylcycloalkyl, (C$_5$–C$_{12}$)aryl, (C$_5$–C$_{12}$)arylalkyl or (C$_5$–C$_{12}$)arylalkenyl optionally comprising one or more heteroatoms selected from N, S, or non-peroxide O, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamido, (C$_5$–C$_6$)aryl, —O—(C$_5$–C$_6$)aryl, arylcarboxamido, alkylthio or haloalkylthio;

$R_2$ and $R_3$ are independently or together H, alkyl, alkylthio, alkylthioalkyl or cycloalkyl, alkylcycloalkyl, phenyl or phenyl alkyl optionally substituted with guanidine, carboalkoxy, hydroxy, haloalkyl, alkylthio, alkylguanidine, dialkylguanidine or amidine;

$R_{10}$ is (C$_5$–C$_6$)aryl, (C$_5$–C$_6$)arylalkyl, (C$_5$–C$_6$)arylalkenyl, cycloalkyl, or arylcycloalkyl optionally comprising one or more heteroatoms selected from N, S, or non-peroxide O, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamido, alkylthio or haloalkylthio;

D is a direct bond, —C(O) or an amino acid selected from proline, isoleucine, cyclohexylalanine, cysteine optionally substituted at the sulfur with alkyl, alkenyl or phenyl optionally substituted with halogen, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio, or haloalkyl thio; phenylalanine, indoline-2-carboxylic acid, tetrahydroisoquinoline-2-carboxylic acid optionally substituted with alkyl, alkenyl, haloalkenyl, alkynyl, halogen, cyano, nitro, haloalkyl, amino, aminoalkyl, dialkylamino, alkoxy, haloalkoxy, carbonyl, carboalkoxy, alkylcarboxamide, arylcarboxamide, alkylthio or haloalkylthio; tryptophan, valine, norvaline, norleucine, octahydroindole-2-carboxylic acid or lysine optionally substituted at the side chain nitrogen with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused aryl-cycloalkyl alkyl optionally comprising 1 or more heteroatoms selected from N, O and S;

A is a direct bond, —C(O)—, —NH—C(O)—, —S(O)$_2$—, —OC(O)— or —CH$_2$—; and $R_{14}$ is H, alkyl, alkenyl or cycloalkyl, aryl, arylalkyl or fused aryl-cycloalkyl optionally comprising 1 or more heteroatoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamido, aryl, arylcarboxamido, alkylthio or haloalkylthio.

2. The compound of claim 1 wherein X is N and Y is O.

3. The compound of claim 1 wherein X is O and Y is N.

4. The compound of claim 2 or 3 wherein D is Val, A is —OC(O)— and $R_{14}$ is benzyl.

5. The compound of claim 4 wherein $R_2$ is isopropyl and $R_3$ is H.

6. The compound of claim 5 wherein $R_1$ is optionally substituted benzyl.

7. The compound of claim 6 wherein $R_1$ is methylbenzyl.

8. The compound of claim 6 wherein $R_1$ is trifluoromethylbenzyl.

9. The compound of claim 9 wherein benzyl is substituted with dialkylamino.

10. The compound of claim 9 wherein the dialkylamino is dimethylamino.

11. The compound of claim 5 wherein $R_1$ is methylenenaphthyl.

12. The compound of claim 5 wherein $R_1$ is methyl.

13. The compound of claim 5 wherein $R_1$ is 3,4-methylenedioxybenzyl.

14. The compound of claim 1 wherein $R_{10}$ is $(C_5-C_6)$aryl or $(C_5-C_6)$arylalkyl.

15. The compound of claim 14 wherein $R_{10}$ is benzyl.

16. The compound of claim 2 or 3 wherein D is —C(O) and $R_{14}$—A is pyrrole.

17. A method of inhibiting at least one serine protease comprising administering to a host in need of such inhibition an effective amount of a compound of claim 1.

18. The method of claim 17 wherein the serine protease is elastase.

19. The method of claim 18 wherein the elastase is human neutrophil elastase.

* * * * *